(12) United States Patent
Mulugeta et al.

(10) Patent No.: US 10,166,271 B2
(45) Date of Patent: Jan. 1, 2019

(54) METHODS FOR PROMOTING HAIR GROWTH

(75) Inventors: Million Mulugeta, Culver City, CA (US); Lixin Wang, Los Angeles, CA (US); Yvette Taché, Los Angeles, CA (US); Jean Rivier, La Jolla, CA (US)

(73) Assignees: THE REGENTS OF THE UNIVERSITY OF CALIFORNIA, Oakland, CA (US); SALK INSTITUTE FOR BIOLOGICAL STUDIES, La Jolla, CA (US)

( * ) Notice: Subject to any disclaimer, the term of this patent is extended or adjusted under 35 U.S.C. 154(b) by 1690 days.

(21) Appl. No.: 11/766,012

(22) Filed: Jun. 20, 2007

(65) Prior Publication Data
US 2008/0280819 A1 Nov. 13, 2008

Related U.S. Application Data

(60) Provisional application No. 60/805,389, filed on Jun. 21, 2006.

(51) Int. Cl.
*A61K 38/17* (2006.01)

(52) U.S. Cl.
CPC .................................. *A61K 38/17* (2013.01)

(58) Field of Classification Search
None
See application file for complete search history.

(56) References Cited

U.S. PATENT DOCUMENTS

| | | | |
|---|---|---|---|
| 5,109,111 A | 4/1992 | Rivier et al. | |
| 5,245,009 A | 9/1993 | Kornreich et al. | |
| 5,493,006 A | 2/1996 | de Miranda et al. | |
| 5,510,458 A | 4/1996 | Kornreich et al. | |
| 5,663,292 A | 9/1997 | Rivier | |
| 5,767,152 A | 6/1998 | Nielsen et al. | |
| 5,777,073 A | 7/1998 | Rivier | |
| 5,874,227 A | 2/1999 | Rivier | |
| 6,323,312 B1 | 11/2001 | Rivier | |
| 6,849,600 B2 | 2/2005 | Wei et al. | |
| 6,927,221 B2* | 8/2005 | Hibi et al. | 514/267 |
| 7,071,161 B2 | 7/2006 | Pisarchik et al. | |
| 2003/0086903 A1 | 5/2003 | Rasmussen et al. | |
| 2003/0113799 A1* | 6/2003 | Pisarchik et al. | 435/7.1 |
| 2003/0186853 A1 | 10/2003 | Wei et al. | |
| 2003/0232100 A1 | 12/2003 | Theoharides | |
| 2004/0034882 A1 | 2/2004 | Vale et al. | |
| 2005/0143403 A1* | 6/2005 | Fu et al. | 514/269 |

FOREIGN PATENT DOCUMENTS

| | | |
|---|---|---|
| WO | WO 99/38868 A1 | 8/1999 |
| WO | WO 99/40089 A1 | 8/1999 |
| WO | WO 99/45007 A1 | 9/1999 |
| WO | WO 99/51599 A1 | 10/1999 |
| WO | WO 99/51608 A1 | 10/1999 |
| WO | WO 00/01697 A1 | 1/2000 |
| WO | WO 00/11003 A1 | 3/2000 |
| WO | WO 02/19975 A1 | 3/2002 |

OTHER PUBLICATIONS

Rohl et al Protein Science 'Helix propagation and N-cap propensities of the amino acids measured in alanine-based peptides in 40 volume percent trifluoroethanol' (1996) 5:2623-2637.*
Paus et al (New England Journal of Medicine 'Mechanisms of Disease—The biology of Hair Follicles' v341 1999 pp. 491-497).*
Brannon ('The Biology of Hair' accessed from http://dermatology.about.com/cs/hairanatomy/a/hairbiology.htm on Aug. 18, 2010, 2 pages).*
Nutrica web site ('Hair Loss Myths Explained' accessed from http://www.retane.com/hair-loss-treatment/hair-loss-myth.htm on Aug. 18, 2010 4 pages).*
Martinez et al (J Pharmacol Exp Ther 2002 v301 pp. 611-617).*
Shirai et al (J Dermatol Sci 2001 v25 pp. 213-218).*
Pharmaceutical information—Rogaine (retrieved from http://www.rxmed.com/b.main/b2.pharmaceutical/b2.1.monographs/CPS-%20Monographs/CPS-%20(General%20Monographs-%20R)/Rogaine.html on Jul. 1, 2014, 7 pages).*
ToxLearn Toxicology Fundamentals (retrieved from http://toxlearn.nlm.nih.gov/htmlversion/module1.html on Jun. 15, 2015, 24 pages).*
Minoxidil—a Hair Growth Stimulant (retrieved from http://www.hairloss-reversible.com/articles/hn17.htm on Jun. 15, 2015, 5 pages).*
Arck et al., "Stress Inhibits Hair Growth in Mice by Induction of Premature Catagen Development and Deleterious Perifollicular Inflammatory Events via Neuropeptide Substance P-Dependent Pathways," *Am. J. Pathol.* 162:803-814, 2003.
Arck et al., "Topical Minoxidil Counteracts Stress-Induced Hair Growth Inhibition in Mice," *Exp. Dermatol.* 12:580-590, 2003.
Botchkarev et al., "p53 is Essential for Chemotherapy-Induced Hair Loss," *Cancer Res.* 60:5002-5006, 2000.
Botchkarev, "Stress and the Hair Follicle: Exploring the Connections," *Am. J. Pathol.* 162:709-712, 2003.
Botchkarev and Paus, "Molecular Biology of Hair Morphogenesis: Development and Cycling," *J. Exp. Zool.* 298B:164-180, 2003.
Cotsarelis and Millar, "Towards a Molecular Understanding of Hair Loss and Its Treatment," *TRENDS in Mol. Med.* 7:293-301, 2001.
Grigoriadis, "Corticotropin-Releasing Factor Receptor Antagonists: Potential Novel Therapies for Human Disease," Sigma-aldrich.com/cellsignaling, *Celltransmissions* 19:3-10, 2003.

(Continued)

*Primary Examiner* — Karlheinz R. Skowronek
*Assistant Examiner* — Ronald T Niebauer
(74) *Attorney, Agent, or Firm* — Riverside Law LLP

(57) ABSTRACT

This disclosure reveals that cyclic corticotrophin releasing factor (CRF) antagonist peptides (such as astressin B, its functional fragments, and their derivatives) induce hair growth and prevent hair loss in vivo. This important discovery enables, for instance, methods of promoting hair growth, and methods of treating hair loss (such as the hair loss that occurs normally in some individuals or that is the result of a health disorder or therapeutic treatment). Exemplary cyclic CRF antagonist peptides useful in the disclosed methods are provided throughout the disclosure.

19 Claims, 8 Drawing Sheets
Specification includes a Sequence Listing.

(56) References Cited

OTHER PUBLICATIONS

Gulyas et al., "Potent, Structurally Constrained Agonists and Competitive Antagonists of Corticotropin-Releasing Factor," *Proc. Natl. Sci. USA* 92:10575-10579, 1995.

Harada and Okajima, "Effect of Topical Application of Capsaicin and Its Related Compounds on Dermal Insulin-Like Growth Factor-I Levels in Mice and on Facial Skin Elasticity in Humans," *Growth Horm. IGF Res.* 17:171-176, 2007.

Hernandez et al., "Synthesis and Relative Potencies of New Constrained CRF Antagonists," *J. Med. Chem.* 36:2860-2867 (1993).

Ito et al., "The Human Hair Bulb is a Source and Target of CRH," *J. Invest. Dermatol.* 122:235-237, 2004.

Ito et al., "Human Hair Follicles Display a Functional Equivalent of the Hypothalamic-Pituitary-Adrenal (HPA) Axis and Synthesize Cortisol," *FASEB J.* 19:1332-1334, 2005.

Kalia et al., "Iontophoretic Drug Delivery," *Adv. Drug Deliv. Rev.* 56:619-658, 2004.

Kawana et al., "Corticotropin-Releasing Factor Receptor Type is Involved in the Stress-Induced Exacerbation of Chronic Contact Dermatitis in Rats," *Exp. Dermatol.* 12:47-52, 2003.

Leitner et al., "Thiomers in Noninvasive Polypeptide Delivery: In Vitro and In Vivo Characterization of a Polycarbophil-Cysteine/Glutathione Gel Formulation for Human Growth Hormone," *J. Pharm. Sci.* 93:1682-1691, 2004.

Martanto et al., "Transdermal Delivery of Insulin Using Microneedles in Vivo," *Pharm. Res.* 21:947-952, 2004.

Martanto et al., "Fluid Dynamics in Conically Tapered Microneedles," *AIChE J.* 51:1599-1607, 2005.

Miranda et al., "Conformationally Restricted Competitive Antagonists of Human/Rat Corticotropin-Releasing Factor," *J. Med. Chem.* 37:1450-1459, 1994.

Mourtas et al., "Liposomal Drugs Dispersed in Hydrogels—Effect of Liposome, Drug and Gel Properties on Drug Release Kinetics," *Colloids Surf. B Biointerfaces*, 55:212-221, 2007.

Omidian et al., "Recent Developments in Superporous Hydrogels," *J. Pharm. Pharmacol.* 59:317-327, 2007.

Park et al., "Biodegradable Polymer Microneedles: Fabrication, Mechanics and Transdermal Drug Delivery," *J. Control. Rel.* 104:51-66, 2005.

Paus and Cotsarelis, "The Biology of Hair Follicles," *New Engl. J. Med.* 341:491-497, 1999.

Paus et al., "The Skin POMC System (SPS) Leads and Lessons from the Hair Follicle," *Ann. NY Acad. Sci.* 885:350-363, 1999.

Peters et al., "Stress Exposure Modulates Peptidergic Innervation and Degranulates Mast Cells in Murine Skin," *Brain Behav. Immun.* 19:252-262, 2005.

Peters et al., "Hair Growth Inhibition by Psychoemotional Stress: a Mouse Model for Neural Mechanisms in Hair Growth Control," *Exp. Dermatol.* 15:1-13, 2006.

Porter, "Mouse Models for Human Hair Loss Disorders," *J. Anat.* 202:125-131, 2003.

Reisch, "Ushering Cosmetics to the Right Spots," *C&EN Northeast News Bureau*, www.cen-online.org, 15-20, May 14, 2007.

Rijkers et al., "Structure-Activity Studies on the Corticotropin Releasing Factor Antagonist Astressin, Leading to a Minimal Sequence Necessary for Antagonistic Activity," *ChemBioChem* 5:340-348, 2004.

Rivier et al., "Constrained Corticotropin Releasing Factor Antagonists (Astressin Analogues) with Long Duration of Action in the Rat," *J. Med. Chem.* 42:3175-3182, 1999.

Rivier et al., "Potent and Long-Acting Corticotropin Releasing Factor (CRF) Receptor 2 Selective Peptide Competitive Antagonists," *J. Med. Chem.* 45:4737-4747, 2002.

Rogers, "Hair Follicle Differentiation and Regulation," *Int. J. Dev. Biol.* 48:163-170, 2004.

Roloff et al., "Hair Cycle-Dependent Expression of Corticotropin-Releasing Factor (CRF) and CRF Receptors in Murine Skin," *FASEB J.* 12:287-297, 1998.

Safer et al., "A Topical Parathyroid Hormone/Parathyroid Hormone-Related Peptide Receptor Antagonist Stimulates Hair Growth in Mice," *Endocrinol.* 148:1167-1170, 2007.

Sintov and Wormser, "Topical Iodine Facilitates Transdermal Delivery of Insulin," *J. Control. Rel.* 118:185-188, 2007.

Slominski et al., "Corticotropin Releasing Hormone and Proopiomelanocortin Involvement in the Cutaneous Response to Stress," *Physiol. Rev.* 80:979-1020, 2000.

Slominski et al., "Hair Follicle Pigmentation," *J. Invest. Dermatol.* 124:13-21, 2005.

Stenn and Paus, "Controls of Hair Follicle Cycling," *Physiol. Rev.* 81:449-494, 2001.

Yamada et al., "New Class of Corticotropin-Releasing Factor (CRF) Antagonists: Small Peptides Having High Binding Affinity for CRF Receptor," *J. Med. Chem.* 47:1075-1078, 2004.

Zbytek and Slominski, "CRH Mediates Inflammation Induced by Lipopolysaccharide in Human Adult Epidermal Keratinocytes," *J. Invest. Dermatol.* 127:730-732, 2007.

Zouboulis et al., "Corticotropin-Releasing Hormone: An Autocrine Hormone that Promotes Lipogenesis in Human Sebocytes," *Proc. Natl. Acad. Sci. USA* 99:7148-7153, 2002.

IBC's 4th Annual Delivery Strategies for Proteins and Peptides, Case Studies and Practical Tactics to Address Current Protein and Peptide Delivery Challenges, Hilton Boston Logan Airport, Boston, MA, Oct. 4-6, 2004, pp. 1-8.

Bergfeld and Mulinari-Brenner, "Hair Disorders," *The Cleveland Clinic*, http://www.clevelandclinicmeded.com, 2003, pp. 1-4.

* cited by examiner

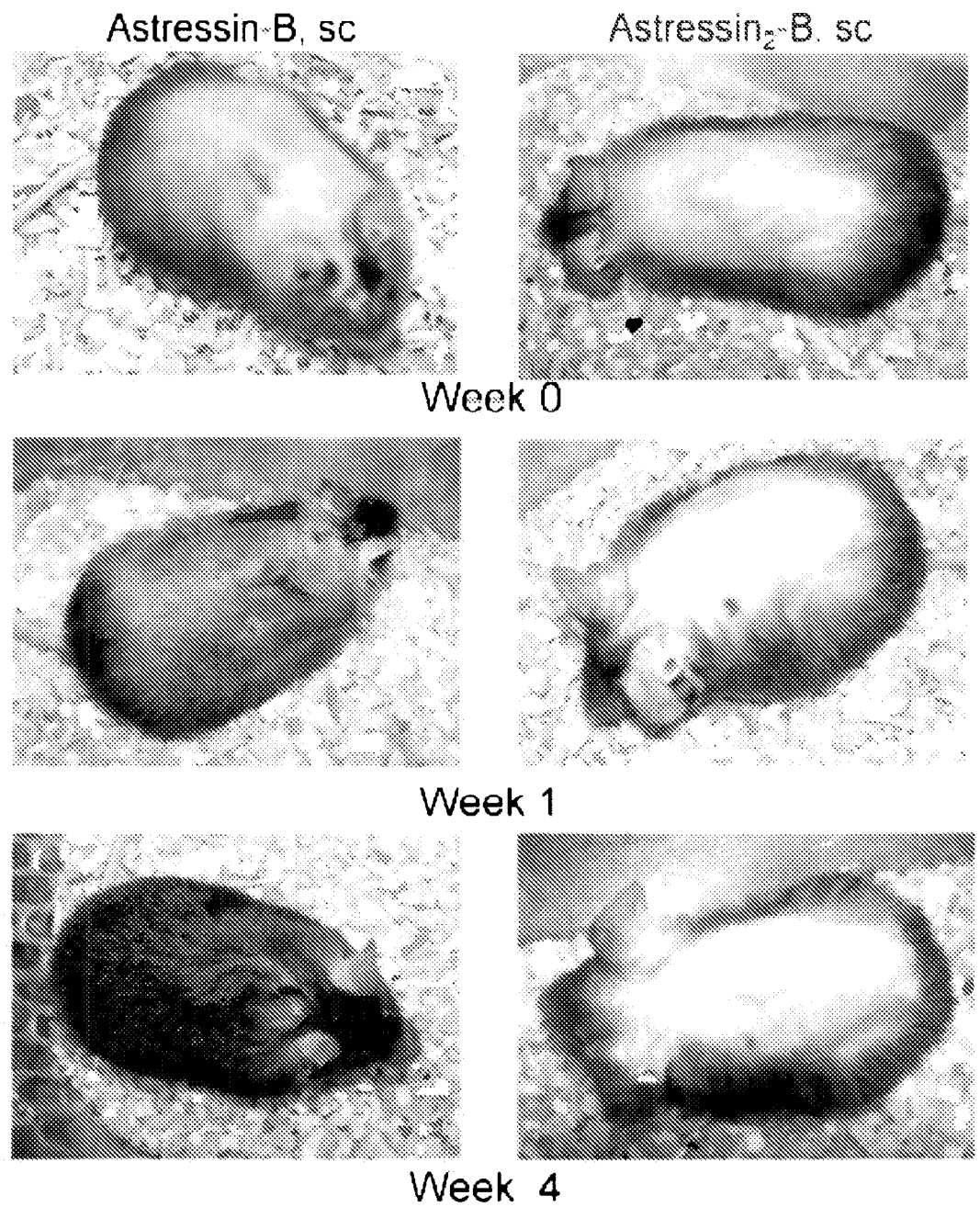

Saline, ip

Astressin-B, ip

FIG. 3A
WT
FIG. 3B
CRF-OE
Astressin-B, sc
FIG. 3C
CRF-OE
Astressin2-B, sc
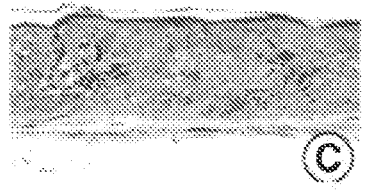
FIG. 3D
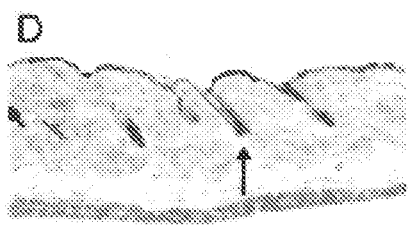
WT
FIG. 3E
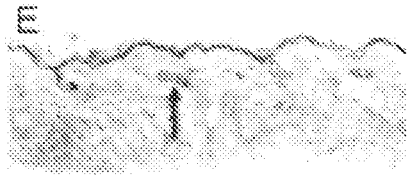
CRF-OE
Saline, ip
FIG. 3F
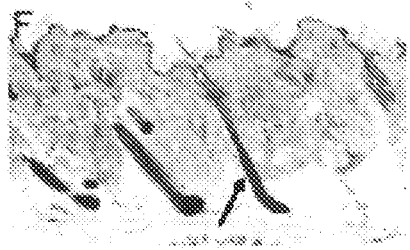
CRF-OE
Astressin-B, ip

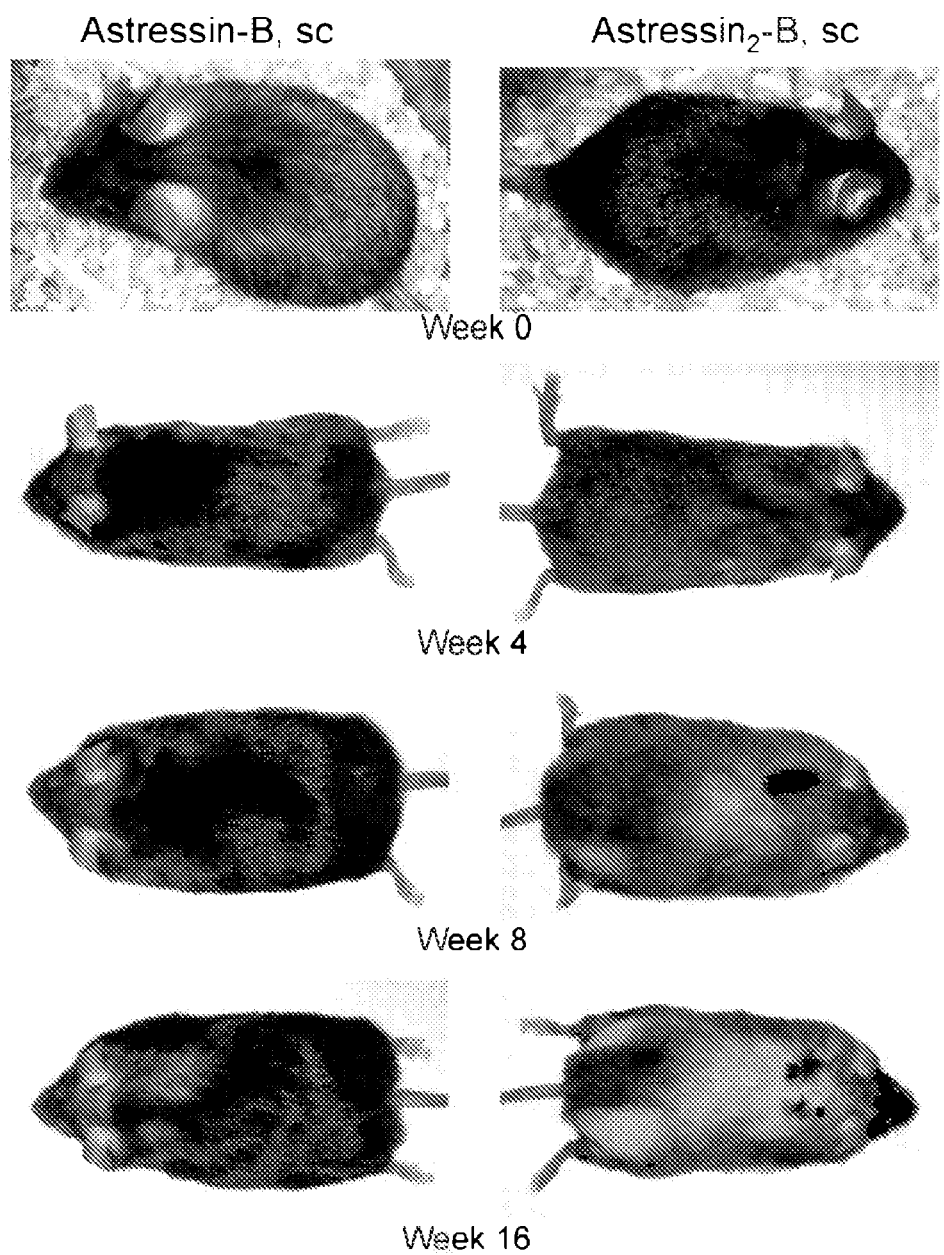

METHODS FOR PROMOTING HAIR GROWTH

CROSS-REFERENCE TO RELATED APPLICATION

This application claims the benefit of U.S. Provisional Application No. 60/805,389 filed Jun. 21, 2006, herein incorporated by reference.

STATEMENT REGARDING FEDERALLY SPONSORED RESEARCH OR DEVELOPMENT

This invention was made with Government support under DK033061 and DK057237 awarded by the National Institutes of Health. This government has certain rights in the invention.

This work was supported by the U.S. Department of Veterans Affairs, and the Federal Government has certain rights in the invention.

FIELD OF THE DISCLOSURE

This disclosure concerns the use of cyclic corticotropin releasing factor (CRF) antagonist peptides to promote hair growth, for example, in the treatment of hair loss.

BACKGROUND

Hair loss is of concern to a large number of men and women. In many individuals, hair loss (i.e., alopecia) causes embarrassment, and/or psychological problems such as depression. Although alopecia is more common in men (e.g., male pattern baldness or androgenic alopecia) than women (e.g., female pattern baldness), it is a significant concern to both men and women. Indeed, millions of dollars and countless hours of research have been dedicated to solving this problem.

The mature hair follicle is a complex mini-organ that has a tightly regulated growth cycle. During postnatal development, the follicle undergoes successive phases of active hair shaft production (anagen), apoptosis-driven regression (catagen), and a quiescent phase (telogen) (Paus et al., *New Engl. J. Med.*, 341:491-497, 1999). During the anagen phase, active hair growth involves cell proliferation in the proximal follicular epithelium, followed by invasion of the elongating follicle into the subcutaneous tissue, differentiation of the epithelium at the base of the follicle, and formation of hair matrix cells, which proliferate and generate a new hair shaft. When the proliferation capacity of the matrix cells is exhausted, a regression phase (catagen) of the hair growth cycle ensues, through which the lower part of the follicle undergoes programmed cell death and involution (Costsarelis et al., *Am. J. Pathol.*, 151:1505-1509, 1997). At this point the follicle enters telogen, the resting period. The cycle is then repeated.

Scalp hair follicles cycle independently of each other. On average, of 100,000 scalp hairs, approximately 90% are in the anagenic (i.e., growth) phase, while the remaining 10% are in the telogenic (i.e., resting) phase, at any given point in time (Whiting, "Disorders of Hair," In: *Scientific American Medicine*, ed. by Dale and Federman, New York:Web MD Scientific American Medicine, 1999, pages 2:XIII:1-7). The anagen phase lasts an average of about three years, with a range of one to seven years, while the telogen phase lasts an average of about three months, after which the resting hairs are shed and new hairs grow in. The average rate of scalp hair growth is approximately 0.35 mm/day (i.e., approximately 1 inch every 2-3 months). In the anagenic phase, the cells surrounding the dermal papilla actively divide approximately every 12 hours, in order to produce cells which line up, grow longer, and begin to keratinize. During a transition stage (i.e., the catagenic or regression phase) that occurs between the anagen and telogen phases, mitosis no longer occurs and the bulb detaches itself from the papilla and rises towards the surface. In the telogenic phase, the hair is fully keratinized and is ready to be expelled. After three to four months, another mitotic cycle begins in the germination zone of the hair and another hair follicle is formed.

An average loss of 100 scalp hairs/day is considered to be normal, with a higher number being shed on days when the hair is washed. In diagnosing hair disorders, it is important to determine whether the shedding is abnormal and whether shed hairs break off or come out by the roots. Hair normally comes out by the roots. However, trauma or excessive fragility of the hair may cause it to break. In examination of patients, hair pull tests may indicate abnormal shedding. In this test, groups of 10-20 hairs are grasped between the index finger and thumb and pulled steadily. Extraction of more than 20% of the grasped hairs potentially indicates abnormal shedding, usually involving telogen hairs. Telogen hairs ("club hairs") are easily recognized, due to their whitish club-shaped bulbs and lack of root sheaths. Normally, anagen hairs are difficult to detach and have blackish, indented roots with intact root sheaths (Whiting, "Disorders of Hair," In: *Scientific American Medicine*, ed. by Dale and Federman, New York:Web MD Scientific American Medicine, 1999, pages 2:XIII:1-7).

There are various forms of alopecia observed in humans. The most common is androgenetic alopecia, although diffuse alopecia, telogen effluvium, anagen effluvium (i.e., anagen arrest), alopecia areata, traumatic alopecia, trichotillomania, cicatricial alopecia, and other types of hair loss are also observed. In addition, hair loss associated with cancer treatment is quite common and of great concern to a large number of patients. Indeed, treatment with various drugs (e.g., alpha blockers, angiotensin converting enzyme inhibitors, anticoagulants, anticonvulsants, antithyroids, beta blockers, calcium channel blockers, cholesterol reducers, $H_2$ receptor blockers, non-steroidal anti-inflammatories, retinoids, retinol, tricyclic antidepressants, and others) can result in hair loss for a significant number of patients. Nutritional deficiencies or excesses also can cause hair loss.

Depending upon the severity, treatment and management of alopecia ranges from continuing observation to medical and surgical treatment, to use of a hairpiece or wig. Minoxidil has been approved by the U.S. Food and Drug Administration for topical use in both men and women. The therapeutic effect of minoxidil is variable: Two percent topical minoxidil produces visible hair growth in approximately ⅓ of male and female androgenetic patients, fine hair growth in approximately ⅓ of patients, and no hair growth in approximately ⅓ of patients. In addition, if the drug is effective, use of the medication must be continued indefinitely; otherwise, loss of hairs that were gained during therapy may occur (Scow et al., *Am. Fam. Physician*, 59:21892194, 1999). Side effects of minoxidil administration include scalp irritation and increased facial hair. The mechanism of action by which minoxidil produces hair growth is not fully understood.

Other compounds that have found use in treatment of alopecia include orally administered finasteride. At a dosage of 1 mg/day given for 2 years to male patients between 18 and 41 years of age, visible hair growth was observed in 66% of cases and further hair loss was prevented in 83% (Whiting, "Disorders of Hair," In: *Scientific American Medicine*, ed. by Dale and Federman, New York:Web MD Scientific American Medicine, 1999, pages 2:XIII:1-7). However, a similar treatment regimen in post-menopausal women was found to be ineffective. Side effects of finasteride include lack of libido, lack of potency, and mild reduction in semen. Because of potential severe teratogenic problems for male fetuses, the drug is contraindicated for use by pre-menopausal women.

Additional drugs for treating androgenetic alopecia in women include oral contraceptives (e.g., ethinyl estradiol-ethynodiol diacetate, desogesterl-ethynyl estradiol, and ethinyl estradiol-norgesterimate), which can reduce hair loss and sometimes lead to slight hair growth (Whiting, "Disorders of Hair," In: *Scientific American Medicine*, ed. by Dale and Federman, New York:Web MD Scientific American Medicine, 1999, pages 2:XIII:1-7). Oral spironlactone and dexamethasone have also found use in treatment of female patients.

For other types of alopecia, various approaches include anthralin, psoralen and ultraviolet A, steroids, topical immunotherapy, immunosuppressives, long-term antimicrobial treatment, etc. However, these treatment regimes present various risks and associated side effects, some of which may be severe. Thus, there remains a need for additional compositions and methods to promote hair growth.

SUMMARY OF THE DISCLOSURE

This disclosure concerns the discovery that cyclic corticotrophin releasing factor (CRF) antagonist peptides (such as astressin B, its functional fragments, and their derivatives) induce hair growth in vivo. This important discovery enables, for instance, methods of promoting hair growth, and methods of treating hair loss (such as the hair loss that occurs normally in some individuals or that is the result of a health disorder or therapeutic treatment).

Exemplary cyclic CRF antagonist peptides useful in the disclosed methods are provided throughout the disclosure and, by way of example, include the following consensus sequence:
(cyclo 30-33)$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$ (SEQ ID NO: 5);
wherein $R_{30}$ is cGlu or cAsp; $R_{31}$ is Aib, DAla or any L-alpha-amino acid other than Cys; $R_{32}$ is His, Glu, DHis, Leu, Lys, Aib, or Ala; $R_{33}$ is cLys, cOrn, cDbu, or cHly; $R_{34}$ is Asn, Aib, or Ala; $R_{35}$ is Arg, Ala, or Lys; $R_{36}$ is Lys, Orn, Arg, Har, Cml, Leu, or Ala; $R_{37}$ is Leu, Cml, Tyr, or Ala; $R_{38}$ is Nle, Cha, Met, Cml, or Phe; $R_{39}$ is Glu, Asp, Aib, or Ala; $R_{40}$ is Ile, Cml, or Ala; and $R_{41}$ is Ile, Ala, Leu, Val, Aib, Gly, Cml, Nle, Nva, Gln, Phe, or Asn;
wherein $R_{41}$ is amidated; and wherein the N-terminal residue of the exemplary cyclic CRF antagonist peptide is N-capped (for example, acylated, pegylated or cabamoylated).

The foregoing and other features and advantages will become more apparent from the following detailed description of several embodiments, which proceeds with reference to the accompanying figures.

BRIEF DESCRIPTION OF THE FIGURES

FIG. 3 shows images of H/E-stained skin sections from (A) wild type mice, (B) adult CRF-OE mice 4 weeks after last astressin B-sc treatment, (C) adult CRF-OE mice, 4 weeks after last astressin 2B-sc treatment (D) wild type mice, (E) adult CRF-OE mice, 2 weeks after last saline-ip treatment (F) adult CRF-OE mice, 2 weeks after last astressin B-ip treatment. Arrows in (D)-(F) indicate hair follicle. The section shown in panel (B) included a subdermal layer of adipocytes, which is a phenotype observed in some CRF-OE mice. Bar scale=100 µm.

SEQUENCE LISTING

Figure 1A:
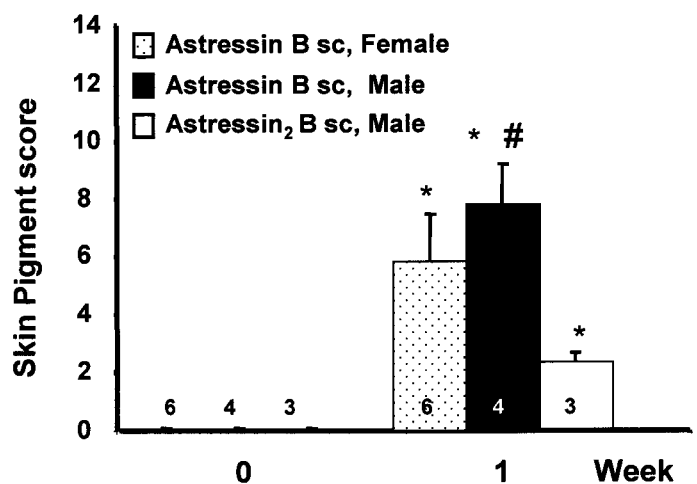
FIG. 1 includes several panels showing the effect of 5 consecutive daily subcutaneous injections (5 µg/mouse/day) of astressin B or astressin 2B on hair growth and skin pigmentation in adult, CRF-OE mice over a period of approximately four weeks. Week 0 corresponds to results prior to injection of the respective peptides. Week 1 and 4 correspond to results 1 week or 4 weeks after the last injection, respectively. The bar graph in panel (A) shows the mean±SEM skin pigmentation score (measured one week after cessation of treatment) for male or female astressin B- or astressin 2B-treated mice as indicated. The number of mice represented is indicated at the base of each bar. Panel (B) shows a time course of the hair growth score (mean±SEM) for the number of male or female astressin B- or astressin 2B-treated mice as indicated. *$p<0.05$ versus week 0, paired t-test; # $p<0.05$ versus astressin 2B at the corresponding week, t-test (panel A) and One Way ANOVA (panel B). The left-most series of digital images in panel (C) shows representative astressin B-treated mouse at the indicated time periods. The right-most series of digital images show a representative astressin 2B-treated mouse at the indicated time periods.

The amino acid sequences listed in the accompanying sequence listing are shown using standard three letter code for amino acids as defined in 37 C.F.R. 1.822. In the accompanying sequence listing:

SEQ ID NO: 1 shows an amino acid sequence of human/rat corticotropin releasing factor (CRF).

SEQ ID NOS: 2-5 show four consensus sequences for exemplary cyclic CRF antagonist peptides.

SEQ ID NOS: 6-15 show exemplary cyclic CRF peptide antagonists.

DETAILED DESCRIPTION

I. Introduction

Disclosed here are methods for promoting hair growth in a subject (such as, a human or a non-human animal, e.g., an animal grown for harvest of its fur or pelt) including the step of administering to the subject an effective amount of a cyclic corticotropin-releasing factor (CRF) antagonist peptide (such as, a non-selective CRF antagonist peptide). In some methods, a useful cyclic CRF antagonist peptide includes the sequence:

(cyclo 30-33)$R_{30}$-$R_{31}$-$R_{32}$-$R_{33}$-$R_{34}$-$R_{35}$-$R_{36}$-$R_{37}$-$R_{38}$-$R_{39}$-$R_{40}$-$R_{41}$ (SEQ ID NO: 5);
wherein $R_{30}$ is cGlu or cAsp; $R_{31}$ is Aib, DAla or any L-alpha-amino acid other than Cys; $R_{32}$ is His, Glu, DHis, Leu, Lys, Aib, or Ala; $R_{33}$ is cLys, cOrn, cDbu, or cHly; $R_{34}$ is Asn, Aib, or Ala; $R_{35}$ is Arg, Ala, or Lys; $R_{36}$ is Lys, Orn, Arg, Har, Cml, Leu, or Ala; $R_{37}$ is Leu, Cml, Tyr, or Ala; $R_{38}$ is Nle, Cha, Met, Cml, or Phe; $R_{39}$ is Glu, Asp, Aib, or Ala; $R_{40}$ is Ile, Cml, or Ala; $R_{41}$ is Ile, Ala, Leu, Val, Aib, Gly, Cml, Nle, Nva, Gln, Phe, or Asn; wherein $R_{41}$ is amidated; and wherein the N-terminal residue of the cyclic CRF antagonist peptide is N-capped (such as, acylated, carbamoylated or pegylated). In the foregoing or other methods, a cyclic CRF antagonist peptide includes a single alpha helix (e.g., consists of a single alpha helix and, optionally, includes other non-helical residues).

A cyclic corticotropin-releasing factor (CRF) antagonist peptide useful in some disclosed methods is astressin B and/or a functional fragment thereof. In other examples, astressin, astressin B, destressin, (cyclo 30-33)[cGlu30, Aib31, Glu32, cLys33, Cha38, Asp39]Ac-hCRF(30-41)) and/or (cyclo 30-33)[cGlu30, Aib31, Glu32, cLys33, Cha38, Asp39, Cml40] Ac-h/rCRF(30-41) are used.

Any mode of administering a cyclic CRF antagonist peptide is contemplated in the disclosed methods. In exemplary methods, a cyclic CRF antagonist peptide is administered by injection (such as intraperitoneal injection, intravenous injection, subcutaneous injection, and/or intramuscular injection) or by topical administration (for example via transdermal delivery). Particular examples involve subcutaneous or intramuscular injection to administer a cyclic CRF antagonist peptide.

A cyclic CRF antagonist peptide can be administered to an area of alopecia-affected skin. For example, a cyclic CRF antagonist peptide can be administered to the scalp of the human. In other examples, a cyclic CRF antagonist peptide is administered systemically via the blood circulation by injection in a site remote from an area of alopecia-affected skin, such as intraperitoneal injection.

Effective amounts of a cyclic CRF antagonist peptide for use in a disclosed method can be determined by routine methods. In exemplary methods, an effective amount of a cyclic CRF antagonist peptide is from about 1 μg/kg body weight to about 500 μg/kg body weight. In specific examples, an effective amount of a cyclic CRF antagonist peptide is from about 0.05 mg/dose to 500 mg/dose (for example 0.5 to 50 mg/dose, such as 5 mg/dose) when administered topically, or 0.025 μg/dose to 500 μg/dose (for example 0.5 to 50 μg/dose, such as 5 μg/dose) when administered by injection (such as i.p. or i.v.).

Also disclosed herein are methods of treating hair loss in a subject including the step of administering to a subject having hair loss cyclic CRF antagonist peptide in a therapeutically effective amount (such as, from about 0.1 μg to about 14 μg per injection site, or from about 1 μg/kg body weight to about 1000 μg/kg body weight, or from about 0.1 mg to about 14 mg per dose for topical administration).

In some methods, hair loss in the subject results from a health disorder or a therapeutic treatment. In more particular methods, the health disorder is alopecia areata, traction alopecia, folliculitis alopecia, telogen effluvium, loose-anagen syndrome, toxic alopecia, acquired immune deficiency (AID), hypothyroidism, hyperthyroidism, lupus erythematosus, diabetes, iron deficiency, syphilis, zinc deficiency, trichotillomania, Cushing syndrome, or stress-related disorder. In other particular methods, a therapeutic treatment is chemotherapy or radiation therapy. In some examples, a therapeutic treatment (such as chemotherapy) includes administration of one or more of cyclophosphamide, daunorubicin, doxorubicin, etoposide, ifosamide, paclitaxel, docetaxel, trimethadione, tacrolimus, lithium, atenolol, metoprolol, nadolol, propranolol, timolol, warfarin, heparin, allopurinol, amphetamines, levodopa, bromocriptine and pergolide, pramipexole, ropinerole, vitamin A, isotretinoin, etretinate, tricyclic antidepressants, amphetamines, bupropion, selegeline, clofibrate, gemfibrozil, cimetidine, ranitidine, famotidine, auranofin, indomethacin, naproxen, sulindac, methotrexate, lisinopril, carbimazole, iodine, thiocyanate, and thiouracil. In other methods, hair loss results from radiation therapy, such as a dose less than about 6,000 cGy (for example 500 6000 cGy).

II. Abbreviations and Terms

Bt butyryl
CRF corticotropin-releasing factor (also known as corticotropin-releasing hormone or "CRH")
Flu fluorenoyl
ip intraperitoneal or intraperitoneally
ipn isopropionyl
Nph naphthoyl
OE overexpressing
Pn propionyl
sc subcutaneous or subcutaneously
Vac vinylacetyl
vl valeryl Unless otherwise noted, technical terms are used according to conventional usage. Definitions of common terms in peptide chemistry may be found in Stewart et al., "Solid Phase Peptide Synthesis," In: *Solid Phase Peptide Synthesis*, 2nd Edition, Rockford, Ill.:Pierce Chemical Company, 1984; Greenstein and Winitz, *Chemistry of the Amino Acids*, New York:J. Wiley and Sons, Chapter 10, 1961; Greenstein and Winitz, *Chemistry of the Amino Acids*, Malbar, Fla.: Robert E. Krieger Publishing Company, 1984; Goodman et al., "Synthesis of Peptides and Peptidomimetics," In: *Methods of Organic Chemistry*, Stuttgart, Germany:Houben-Weyl, 2001-2004.

In order to facilitate review of the various embodiments of the disclosure, the following explanations of specific terms are provided:

Acyl: An organic moeity (or functional group) obtained from an organic acid by the removal of the carboxylic hydroxyl group. Acyl groups have the general formula R—CO— where R can be, e.g., aliphatic, alkyd, or aromatic.

Administration: To provide or give a subject an agent, such as a composition that includes one or more cyclic CRF antagonist peptides. Exemplary routes of administration include, but are not limited to, parenteral and/or enteral routes, such as intrathecal, subcutaneous (sc), intramuscular (im), intradermal, intraperitoneal (ip), and intravenous (iv), transdermal, intranasal, epidural, intrarectal, intravaginal, buccal absorption, topical, and/or oral routes.

Aliphatic: A straight-chain, branched-chain, or cyclic alkane, alkene, or alkyne. In some examples, an aliphatic group contains from 1 to 25 carbon atoms; for example, from 1 to 15, from 1 to 10, or from 1 to 6 carbon atoms. An aliphatic group having 15 or fewer carbon atoms (such as from 1 to 10 or from 1 to 6 carbon atoms) may be referred to as a "lower aliphatic" group. Unless expressly referred to as an "unsubstituted aliphatic," aliphatic groups can either be unsubstituted or substituted. An aliphatic group can be substituted with one or more substituents (for instance, up to two substituents for each methylene carbon in an aliphatic chain, or up to one substituent for each carbon of a —C=C— double bond in an aliphatic chain, or up to one substituent for a carbon of a terminal methine group). Exemplary aliphatic substituents include, for instance, amine, amide, sulfonamide, halogen, cyano, carboxy, hydroxy, mercapto, trifluoromethyl, alkyl, alkoxy, alkylthio, thioalkoxy, arylalkyl, heteroaryl, alkylamino, dialkylamino, or other functionality, or combinations thereof.

Alkyl: A straight-chain, branched-chain, or cyclic hydrocarbon that is saturated. Alkyl groups include, for example, methyl, ethyl, n-propyl, isopropyl, isobutyl, t-butyl, pentyl, pivalyl, heptyl, adamantyl, or cyclopentyl groups, or combinations thereof. Alkyl groups can either be unsubstituted or substituted with one or more substituents, e.g., halogen, alkyl, alkoxy, alkylthio, hydroxy, carboxy, aryl, arylalkyl, amide, amino, alkylamino, dialkylamino, or other functionality, or combinations thereof. "Lower alkyl" is an alkyl group having 15 or fewer carbon atoms (such as from 1 to 10 or from 1 to 6 carbon atoms).

Alopecia: Hair loss (e.g., baldness or hair thinning) from one or more areas where hair is normally present. It is intended that the term encompass hair loss that results from any cause. In some examples, the term refers to the loss of scalp hair, although it is not intended to be so limited. Indeed, it is intended that the term encompass full or partial hair loss, shedding or any decrease in the number of follicles or follicles in the anagen phase at any body site where hair is normally present.

Alpha helix: A particular helical folding of amino acids in a polypeptide backbone, in which the carbonyl oxygens are hydrogen bonded to amide nitrogen atoms three residues along the chain. In a typical alpha helix, the translation of amino acid residues along the long axis of the helix is 0.15 nm and the rotation per residue is 100°; accordingly, there are 3.6 residues per turn. Side chains of helix-resident amino acids are arranged at the outside of the helix. Alpha helices are destabilized, for example, by (i) the substitution of Pro for any helix-resident amino acid, (ii) Asp adjacent to Glu in a helix, or (iii) a cluster of Ile residues (such as, 3 or more contiguous Ile residues) in a helix. In particular examples, helix destabilizing amino acids preferably are not present in an alpha helix.

Amidation: A condensation reaction between a carboxylic acid group (such as the carboxy-terminus of a peptide) and an amine group (—N($R_1$)($R_2$)) to form a substituted or unsubstituted amide (—C(O)N($R_1$)($R_2$)) group, where $R_1$ and $R_2$ independently can be hydrogen, alkyl (such as substituted or unsubstituted lower alkyl), aliphatic (such as substituted or unsubstituted lower aliphatic), aryl (such as substituted or unsubstituted aryl), or heteroatom-containing moieties (such as nitrogen-, sulfur-, or oxygen-containing moieties). A polypeptide can be synthetically amidated, for instance, by activating a C-terminal carboxy group using a coupling reagent in the presence of an amine. Alternatively, peptide amides can be synthesized using a C-terminal amino acid amide. For example, certain solid phase supports used for peptide synthesis yield C-terminal peptide amides upon cleavage of the peptide from the support. Polypeptide amidation also can be catalyzed by enzymes (e.g., peptidylglycine alpha-amidating monooxygenase or PAM) in vivo or in vitro.

Analog: A molecule that is similar to another molecule in its effect(s) (e.g., ability to promote hair growth) but differs in its chemical structure. Typically, the chemical structures of analogs are related and differ in ways that do not affect the common function of the analogs. For example, analogs may differ in the composition of one or more substituents (such as, the length of an alkyl chain, and/or substitution of one functional group for another functional group, for instance, where the functional groups have similar chemical properties), and/or in ionization state, or one analog may be a molecular fragment (or substructure) of the other. Structural analogs can be found using quantitative structure activity relationships (QSAR), with techniques such as those disclosed in Remington (*The Science and Practice of Pharmacology*, 19th Edition, Chapter 28, 1995). A derivative is an analog that is derived from a base (or parent) chemical structure. A derivative compound is or could be formed from a similar compound or can be imagined to arise from another compound by chemical syntheses, for example, if one or more atoms or functional groups is replaced with another atom or group of atoms. A "mimetic" is a molecule that mimics the activity of another molecule, but which may not have a recognizably similar chemical structure.

Carbamoylation: Carbamoylation refers to the addition of an —C(O)N($R_2$)($R_3$) group. For example, carbamoylation of an amino group provides a carbamate moiety (—$NR_1$C(O)N($R_2$)($R_3$)) where $R_1$, $R_2$, and $R_3$ independently can be hydrogen, alkyl (such as substituted or unsubstituted lower alkyl), aliphatic (such as substituted or unsubstituted lower aliphatic), or aryl (such as substituted or unsubstituted aryl). Typically, $R_1$, $R_2$, and $R_3$ independently are hydrogen or substituted or unsubstituted lower alkyl. One example of a carbamoyl group is —C(O)$NH_2$ or "Cbm" group. By way of example, an alpha-amino group of an amino acid, a terminal amino group of a peptide, or an epsilon amino group of a lysine residue can be modified by carbamoylation. In particular examples, carbamoylation of a peptide involves a terminal amino group of a peptide. An amino group in a peptide can be carbamoylated by any method known in the art; for example, reaction of a peptide with isocyanates (e.g., Jiang et al., *J. Med. Chem.*, 44:453-467, 2001) or using 1-(2-chloroethyl)-3-cyclohexyl-1-nitrosourea or cyclohexyl isocyanate (Wheeler et al., *Cancer Res.*, 35(11):2974-84, 1975). Additional examples of carbamoylating agents are well known to those of skill in the art and are commercially available, for instance, from Advanced Chemtech (Louisville, Ky.), Sigma-Aldrich (USA), Lancaster (USA), and Bachem (Switzerland).

Hair: The specialized keratinized structures derived or protruding from invaginations of the epidermis that are observed on animals, including mammals. Thus, the term is also intended to encompass hair coats (e.g. fur) of various non-human animals.

Hair loss: A net decrease in the amount of hair present on a particular region (e.g. on the scalp or over the entire body) of a subject as compared to another (e.g., control) time point for the same subject or as compared to a second subject or to a population that serves as a control (i.e., a substantially unchanged standard). Hair loss need not have any particular cause, but may arise, for example, when lost hairs (e.g., shedding and/or breaking hairs) exceed the growth of new hairs. Hair loss may occur prior to any observable symptoms (e.g., baldness, bald patches or visible hair thinning). Hair loss can be quantified as at least 2%, at least 5%, at least 10%, at least 25%, at least 50%, at least 75% or up to 100% fewer hairs present on a particular region of a subject as compared to control.

Health disorder: A condition which deviates from or disrupts normal bodily functions or body tissues in an abnormal way, and is manifested by a set of signs or symptoms. Health disorders include, without limitation, nutritional imbalances (e.g., nutritional deficiencies or nutritional excesses) and other illnesses.

Pegylation: The process of attaching a polyethylene glycol molecule to a polypeptide (such as to the N-terminus of a polypeptide). Polyethylene glycol is a condensation polymer (HO—(CH$_2$—CH$_2$—O)$_n$—H) made from ethylene glycol units. In some examples, a PEG polymer has no more than 30 carbon atoms (such as, no more than 20, 10, or 5 carbon atoms). Pegylation optionally can be used to confer advantageous properties on a peptide intended for administration to a subject, including increased biological stability, solubility and diffusion (see, e.g., Na, et al., *Pharm. Res.*, 22:743-749, 2005; Greenwald, et al., *Adv. Drug Deliv. Rev.*, 55:217-250, 2003; Felix et al., *Int. J. Pep. Prot. Res.*, 46:253-264, 1995; Esposito et al., *Adv. Drug Deliv. Rev.*, 55:1279-1291, 2003; D'Antonio et al., *Growth Horm. IGF Res.*, 14:226-234, 2004; Campbell et al., *J. Pept. Res.*, 49:527-537, 1997; Samant et al., *J. Med. Chem.*, 49(12): 3536-3543, 2006).

Subject: A living multicellular, vertebrate organism, such as a mammal. Preferably, a subject bears hair over some portion of its body during some point in its life cycle. Representative subjects include human and non-human (e.g., animal) subjects, such as rodents (including mice or rats), dogs, cats, sheep, cows, goats (e.g., angora goats and others), horses, milk, llama, alpaca, fox, rabbit chinchillas, beaver, sable, non-human primates (including lemurs, monkeys orangutans, gorillas, bonobos, or chimpanzees), domestic fowl, any animal from which fur (e.g., wool or pelt) is harvested for human or other use, or combinations thereof. The disclosed methods have equal application in medical and veterinary settings. Therefore, a general term such as "subject being treated" should be understood to include all animals (e.g., humans, apes, dogs, cats, horses, and cows) that may benefit from the desired biological effect, such as promoting hair growth, including slowing, stopping or reversing hair loss.

Therapeutically Effective Amount: An amount sufficient to achieve a desired biological effect, for example an amount that is effective to promote hair growth, including slowing, stopping or reversing hair loss. In particular examples, it is an amount (e.g., concentration or weight) of cyclic CRF peptide antagonist effective to promote hair growth (e.g., slow, stop or reverse hair loss) in a subject to whom it is administered or in any other living or non-living sample containing hair follicles. Therapeutically effective amounts of cyclic CRF peptide antagonists and methods of administration are described in detail below.

Treating or treatment: With respect to a condition, such as hair loss, either term includes (i) preventing the condition, e.g., causing the clinical symptoms of the condition not to develop in a subject that may be exposed to or predisposed to the condition but does not yet experience or display symptoms of the condition, (ii) inhibiting the condition, e.g., arresting or slowing the development of the condition or its clinical symptoms, or (iii) relieving the condition, e.g., causing regression of the condition or its clinical symptoms.

Unless otherwise explained, all technical and scientific terms used herein have the same meaning as commonly understood by one of ordinary skill in the art to which the invention belongs. The singular terms "a," "an," and "the" include plural referents unless context clearly indicates otherwise. Similarly, the word "or" is intended to include "and" unless the context clearly indicates otherwise. "Comprising" means "including." Hence "comprising A or B" means including A, including B, or including both A and B. It is further to be understood that any molecular weight or molecular mass values are approximate. Although methods and materials similar or equivalent to those described herein can be used in the practice or testing of the present invention, suitable methods and materials are described below. Such materials, methods, and examples are illustrative only and not intended to be limiting. All publications, patent applications, patents, and other references mentioned herein are incorporated by reference in their entirety to the extent permitted by applicable laws and rules. In case of conflict, the present specification, including explanations of terms, will control.

III. Cyclic CRF Antagonist Peptides

A new function of cyclic CRF antagonist peptides has now been discovered: Promoting hair growth. Numerous cyclic CRF antagonist peptides are known in the art (see, e.g., U.S. Pat. Nos. 6,323,312; 5,874,227; 5,777,073; 5,510,458; PCT Publication No. WO 96/19499; Miranda et al., *J. Med. Chem.*, 37(10):1450-1459, 1994; Gulyas et al., *Proc. Natl. Acad. Sci. USA*, 92(23):10575-9, 1995; Rivier et al., *J. Med. Chem.*, 42(16):3175-3182, 1999; Yamada et al., *J. Med. Chem.*, 47(5):1075-1078, 2004; Rijkers et al., *ChemBioChem*, 5:340-348, 2004).

Non-peptide CRF receptor antagonists also are known (see, e.g., Chen, *Curr. Med. Chem.*, 13:1261-1282, 2006). With regard to the present disclosure, cyclic CRF antagonist peptides may offer advantages over non-peptide antagonists. When administered systemically, non-peptide CRF receptor antagonists likely will have at least some undesirable side effects that will be avoided by the use of cyclic CRF peptide antagonists. Peptides (such as cyclic CRF peptide antagonists) generally will not cross the blood-brain barrier while small molecule, non-peptide CRF receptor antagonists likely will be transported to the brain. CRF receptors are known to have important functions in the brain, which may be disrupted by delivery of non-peptide CRF receptor antagonists to this organ. More generally, at least one non-peptide CRF receptor antagonist was found to alter reversibly liver enzyme levels to the point that the studies were discontinued (Chen and Grigoriadis, *Drug Develop. Res.*, 65:216-226, 2005). To the contrary, cyclic CRF antagonist peptides have been administered in vivo with no measurable adverse effects (see Examples and Broadbear et al., *Neuropsychopharm.*, 29:1112-1121, 2004; Rivier et al., *J. Med. Chem.*, 42:3175-3182, 1999, Martinez et al., *Am. J. Physiol.*, 290: 629-634, 1999; and Wang et al., *Am. J. Physiol. Regul. Integr. Comp. Physiol.*, 281:R1401-R1410, 2001).

There are two known CRF receptor subtypes, CRF-R1 and CRF-R2 (Chen et al., *Proc. Natl. Acad. Sci. USA*, 90:8967-8971, 1993; Lovenberg et al., *Proc. Natl. Acad. Sci. USA*, 92:836-840, 1995), which are expressed in a variety of species. CRF-R2 has at least three known isoforms (Hauger et al., *Pharmacol. Rev.*, 55:21-26, 2003) and several CRF-R1 isoforms have been characterized in human and rodent skins (Pisarchick et al., *FASEB J.*, 15:2754-56, 2001; Pisarchick et al., *Eur. J. Pharmacol.*, 271:2821-30, 2004). In some examples, a cyclic CRF antagonist peptide useful in a disclosed method is a non-selective antagonist of any known CRF receptor (including, for instance, CRF-R1 and/or CRF-2 (such as, CRF-R2a, CRF-R2b)) from any species in which it is desirable to promote hair growth (such as, humans or animals grown commercially for fur harvest). An exemplary non-selective cyclic CRF peptide antagonist antagonizes one or more functions of CRF-R1 (or one or more isoform-s thereof) and CRF-R2 (or one or more isoforms thereof). Other method embodiments involve the use of a cyclic CRF antagonist peptide that non-selectively binds one or more CRF receptors (such as CRF-R1 and/or CRF-R2 (e.g., CRF-R2a and/or CRF-R2b)) without significantly activating same. For example, cyclic CRF antagonist peptide binding affinities ($EC_{50}$) for CRF-R1 may be in the range of 50 nM or less (e.g., from about 50 nM to about 0.3 nM, from about 50 nM to about 5 nM, or from about 50 nM to about 10 nM), or may equal or exceed the binding affinity of known agonists (such as, oCRF or hCRF) for their cognate CRF-R1. In some method embodiments, a cyclic CRF antagonist peptide that non-selectively binds to a CRF-R1 has an intrinsic activity with respect to such receptor of about 10% or less (such as about 5% or less, or about 2% or less) as compared to native CRF. In other examples, cyclic CRF antagonist peptide binding affinities ($EC_{50}$) for CRF-R2 may be in the range of 50 nM or less (e.g., from about 50 nM to about 0.3 nM, from about 50 nM to about 5 nM, or from about 50 nM to about 10 nM), or may equal or exceed the binding affinity of known agonists for their cognate CRF-R2. In other method embodiments, a cyclic CRF antagonist peptide that non-selectively binds to a CRF-R2 has an intrinsic activity with respect to such receptor of about 10% or less (such as about 5% or less, or about 2% or less) as compared to native CRF.

In other examples, cyclic CRF antagonist peptides useful in a disclosed method significantly reduce or inhibit at least one function of any known CRF receptor (such as, CRF-R1 and/or CRF-R2 (e.g., CRF-R2a and/or CRF-R2b)), including inhibition of CRF-stimulated ACTH release or CRF-stimulated cAMP production in cells natively or recombinantly expressing CRF-R1. Inhibition of CRF-R1 or CRF-R2 function by some cyclic CRF antagonist peptides may be at least about 30% at least about 50%, at least about 70%, at least about 80%, at least about 90% or even higher. Therefore, 100% inhibition is not required.

A family of CRF-like peptides is considered to encompass those peptides which bind to the CRF receptors and have at least about 45% amino acid structural homology with ovine CRF, the first mammalian CRF isolated and characterized. The CRF-like family of peptides includes, without limitation, ovine CRF, rat/human CRF (SEQ ID NO: 1), porcine CRF, bovine CRF, fish CRFs, β-helical CRF(AHC), carp urotensin, sucker urotensin, maggy sole urotensin, flounder urotensin, sauvagine and urocortin I. Cyclic CRF antagonist peptides useful in a disclosed method can significantly reduce or inhibit a CRF-R1- and/or CRF-R2 mediated function induced by any one of the foregoing CRF-like family peptides.

The nomenclature used to describe cyclic CRF antagonist peptides is that specified by Schroder and Lubke, *The Peptides*, New York:Academic Press, 1965. In conformance with conventional representation, the amino-terminal residue appears as the left-most residue in a peptide chain and the carboxy-terminal residue appears as the right-most residue. The standard 3-letter abbreviations are used to identify the alpha-amino acid residues, and where the amino acid residue has isomeric forms, it is the L-form of the amino acid that is represented unless otherwise expressly indicated. Modified amino acids described herein have the following three-letter abbreviations:

| | |
|---|---|
| Agl | aminoglycine |
| Aib | $C^{\alpha}CH_3$-alanine or 2-aminoisobutyric acid |
| Amp | (2-, 3- or 4-aminomethyl)phenylalanine |
| Aph | L-(2-,3-or 4-amino)phenylalanine |
| Cha | cyclohexylalanine |
| Cml | $C^{\alpha}CH_3$-L-leucine |
| Cpa | L-(2-, 3-, or 4-chloro)phenylalanine |
| Dbu | L-2,4-diaminobutyric acid |
| Dpr | L-2,3-diaminopropionic acid |
| Hly | L-homolysine |
| Har | L-homoarginine |
| Nal | L-β-(1- or 2-naphthyl)alanine |
| Nic | 3-carboxypyridine (or nicotinic acid) |
| Nle | L-norleucine |
| Nva | L-norvaline |
| Orn | L-ornithine |
| Pal | L-β-(2-, 3- or 4-pyridyl)alanine |
| pGlu | pyroglutamic acid |

The structure-function relationships of CRF antagonist peptides (such as cyclic CRF antagonist peptides) are very well known (see, e.g., Eckart et al., *Proc. Natl. Acad. Sci. USA*, 98(20): 11142-7, 2001; Rivier et al., *J. Med. Chem.*, 41(14):2614-20, 1998; Rivier et al., *J. Med. Chem.*, 42(16): 3175-3182, 1999; Yamada et al., *J. Med. Chem.*, 47(5):1075-1078, 2004; Rijkers et al., *ChemBioChem*, 5:340-348, 2004; Brauns et al., *Peptides*, 23:1817-1827, 2002; Brauns et al., *Peptides*, 23:881-888, 2002).

N-terminal deletion of CRF gives rise to CRF competitive antagonists (Rivier et al., *Science*, 224:889-891, 1984; Gulyas et al., *Proc. Natl. Acad. Sci. USA*, 92(23):10575-9, 1995). Some of the first such CRF competitive antagonists were the non-cyclic peptides alpha-helical CRF9-41 and [DPhe12, Nle21,38]h/rCRF12-41. CRF was believed to assume an alpha-helical structure upon binding to a CRF receptor (Hernandez et al., *J. Med. Chem.*, 36:2860, 1993); thus, a family of conformationally restricted CRF antagonists was synthesized by introducing (among other modifications) cyclizing bonds between two residues of a CRF antagonist peptide (see, e.g., Miranda et al., *J. Med. Chem.*, 37(10):1450-1459, 1994, Gulyas et al., *Proc. Natl. Acad. Sci. USA*, 92(23):10575-9, 1995). One of the earliest, potent cyclic CRF antagonist peptides of CRF-R1 and CRF-R2 was named astressin and has the formula: [(cyclo 30-33) [DPhe12, Nle21,38, Glu30, Lys33]h/rCRF12-41 (Gulyas et al., *Proc. Natl. Acad. Sci. USA*, 92(23):10575-9, 1995). Numerous analogs of astressin have been produced, including, for example, a longer-acting analog named astressin B, which has the formula: (cyclo 30-33)[DPhe12, Nle21,38, Cml27,40, Glu30, Lys33]Ac-h/rCRF9-41 (Rivier et al., *J. Med. Chem.*, 42(16):3175-3182, 1999).

Cyclic CRF antagonist peptides useful in the disclosed methods include at least one cyclizing bond (e.g., a lactam bridge, a disulfide bridge, a lanthionine bridge, a carba bridge (where an amide bond is replace by two $CH_2$ groups) and the like) between the side chains of two residues of the peptide. Amino acid residues involved in a cyclizing bond may be indicated by "c" preceding the three-letter code for such amino acid; thus for instance cGlu, cLys, cOrn, or cHly. Amino acid residues involved in a cyclizing bond also (or alternatively) may be indicated by the applicable residue numbers preceded by "cyclo"; thus, for instance, "cyclo 30-33" indicates a cyclizing bond between the side chains of residues 30 and 33. In some exemplary cyclic CRF antagonist peptides a cyclizing bond (e.g., a lactam bridge) is between residues 30 and 33, or between residues 20 and 23, or between residues 32 and 36.

Further studies demonstrated that advantageous properties (e.g., increase potency duration of action and/or bioavailability) were gained by specific modifications of residues of a cyclic CRF antagonist peptide (see, e.g., Rivier et al., *J. Med. Chem.*, 42(16):3174-3182, 1999). Some exemplary modifications include N-capping of the peptide N-terminus to form, for example, acyl-, carbamate- or urea-capped peptides. In some disclosed methods, the N-terminal residue of a cyclic CRF antagonist peptide is acylated, carbamoylated or pegylated, and/or a C-terminal residue is amidated.

Particular examples of suitable acyl groups are aryl or aliphatic, such as lower alkyl, and particularly including lower alkyl acyl groups. Typically a PEG group of some pegylated residues can include no more than 20 carbon atoms, no more than 16 carbon atoms, or no more than 10 carbon atoms. Examples of such groups and reagents and methods for pegylating peptides are known to those of ordinary skill in the art. For example, preparation of pegylated peptide conjugates is described in U.S. Pat. Nos. 6,528,485 and 6,962,954. Additional examples of suitable methods for pegylating peptides can be found in *Polyethylene Glycol Chemistry: Biotechnical and Biomedical Applications*, ed. by Harris, New York:Plenum Press, Chapter 21, 1992, or Samant et al., *J. Med. Chem.*, 49(12):3536-3543, 2006.

More recent studies have demonstrated that as few as twelve C-terminal residues of a cyclic CRF antagonist peptide, such as astressin or astressin B, are needed to retain the activity of such antagonist peptide (Yamada et al., *J. Med. Chem.*, 47(5):1075-1078, 2004; Rijkers et al., *ChemBioChem*, 5:340-348, 2004). In conformance with the previously described Schroder and Lubke nomenclature (*The Peptides*, NY:Academic Press, 1965), a representation for such small cyclic CRF peptide antagonists is (cyclo$R_a$-$R_b$) [$M_n$]h/r$M_x$-CRF $R_y$-$R_z$, where $R_a$ and $R_b$ are the residues forming the cyclizing bond, $M_n$ is one or more residues (such as Glu30, Lys33, Nle38, and/or Cml40) that differ from the native h/rCRF sequence, $M_x$ is an optional N-terminal modification (also referred to as "Y"), such as carbamoylation pegylation, or acylation and $R_y$ and $R_z$ indicate the residues of CRF (substituted or modified as otherwise indicated) contained in the small peptide (e.g. CRF 30-41 for a twelve residue peptide). C-terminal amidation is represented by "—$NH_2$."

A. Representative Structures

Given the vast amount of structure-function information available for cyclic CRF antagonist peptides, a large genus of such peptides having hair-growth-promoting activity (such as, CRF-R non-selective antagonist peptides) has been and is herein described.

Table 1 provides four consensus sequences (SEQ ID NOS: 2-5) for exemplary cyclic CRF antagonist peptides. The position of each residue in each consensus sequence is given across the top of the table from residue 9, 15, 26, or 30, as applicable, through residue 41 of h/rCRF with suitable amino acids indicated at each position and cyclized residues preceded by "c" (see positions 30 and 33). It is intended that each amino acid at each position where there are two or more amino acids indicated is independently selected. Generally, the four consensus sequences are referred to as (cyclo30-33)[$M_{13-15}$, $M_{17-41}$]h/rCRF 9-41 (SEQ ID NO:2); (cyclo30-33)[$M_{15}$, $M_{17-41}$]h/rCRF 15-41 (SEQ ID NO:3); (cyclo30-33)[$M_{26-41}$]h/rCRF 26-41 (SEQ ID NO:4); or (cyclo30-33)[$M_{30-41}$]h/rCRF 30-41 (SEQ ID NO:5), respectively, with residues ("M") as set forth in Table 1 at the indicated positions.

In any methods involving an exemplary cyclic CRF antagonist peptide or consensus cyclic CRF antagonist peptide sequence as described herein, it should be understood that the N-terminus of such peptide optionally can be modified, e.g., by carbamoylation, acylation, or pegylation (as discussed in more detail elsewhere), and that the C-terminal residue of such peptide typically is amidated. Similarly, aromatic side chains of amino acid residues (such as Trp or Phe) present in any described cyclic CRF antagonist peptide or consensus cyclic CRF antagonist peptide sequence, optionally, can be singly or multiply (as many substitutions as permitted by valence requirements) halogenated, methylated, and/or methoxylated.

TABLE 1

Exemplary Cyclic CRF Antagonist Peptides

SEQ ID NO:2

| Pos | Residue (alternatives) |
|---|---|
| 9 | Asp |
| 10 | Xaa / Leu / Cml |
| 11 | Xaa / Thr / Ser |
| 12 | Xaa / DPhe / DLeu / DTyr / DTrp / DCpa / DNal / DPal / Phe / Tyr |
| 13 | Xaa / His / Tyr / Glu |
| 14 | Xaa / Leu / Cml / Ile |
| 15 | Xaa / Leu / Cml |
| 16 | Arg |
| 17 | Xaa / Glu / Arg |
| 18 | Xaa / Val / Cml / Asn / Lys |
| 19 | Xaa / Leu / Nle / Cml / Met |
| 20 | Xaa / Glu / DGlu / His |
| 21 | Xaa / Nle / Met |
| 22 | Xaa / Ala / DAla / Aib / Asp / Thr / DThr / Glu / DGlu |
| 23 | Xaa / Arg / Lys |
| 24 | Xaa / Ala / Aib / Cml / Val |
| 25 | Xaa / Glu / Asp |
| 26 | Xaa / Gln / Asn |
| 27 | Xaa / Leu / Cml / Ala |
| 28 | Xaa / Ala / Aib / Lys / Arg |
| 29 | Xaa / Gln / Aib / Glu / Ala |
| 30 | Xaa / cGlu / cAsp |
| 31 | Xaa / *** / Aib / DAla |
| 32 | Xaa / His / Glu / DHis / Leu / Lys / Ala / Aib |
| 33 | Xaa / cLys / cOrn / cDbu / cHly |
| 34 | Xaa / Asn / Aib / Ala |
| 35 | Xaa / Arg / Ala / Lys |
| 36 | Xaa / Lys / Orn / Arg / Har / Cml / Leu / Ala |
| 37 | Xaa / Leu / Cml / Tyr / Ala |
| 38 | Xaa / Nle / Cha / Met / Cml / Phe |
| 39 | Xaa / Glu / Asp / Aib / Ala |
| 40 | Xaa / Ile / Cml / Ala |
| 41 | Xaa / Ile / Ala / Leu / Val / Aib / Gly / Cml / Nle / Nva / Gln / Asn / Phe |

SEQ ID NO:3

| Pos | Residue (alternatives) |
|---|---|
| 15 | Xaa / Leu / Cml / Ile |
| 16 | Arg |
| 17 | Xaa / Glu / Arg |
| 18 | Xaa / Val / Cml / Asn / Lys |
| 19 | Xaa / Leu / Nle / Cml / Met |
| 20 | Xaa / Glu / DGlu / His |
| 21 | Xaa / Nle / Met |
| 22 | Xaa / Ala / DAla / Aib / Asp / Thr / DThr / Glu / DGlu |
| 23 | Xaa / Arg / Lys |
| 24 | Xaa / Ala / Aib / Cml / Val |
| 25 | Xaa / Glu / Asp |
| 26 | Xaa / Gln / Asn |
| 27 | Xaa / Leu / Cml / Ala |
| 28 | Xaa / Ala / Aib / Lys / Arg |
| 29 | Xaa / Gln / Aib / Glu / Ala |
| 30 | Xaa / cGlu / cAsp |
| 31 | Xaa / *** / Aib / DAla |
| 32 | Xaa / His / Glu / DHis / Leu / Lys / Ala / Aib |
| 33 | Xaa / cLys / cOrn / cDbu / cHly |
| 34 | Xaa / Asn / Aib / Ala |
| 35 | Xaa / Arg / Ala / Lys |
| 36 | Xaa / Lys / Orn / Arg / Har / Cml / Leu / Ala |
| 37 | Xaa / Leu / Cml / Tyr / Ala |
| 38 | Xaa / Nle / Cha / Met / Cml / Phe |
| 39 | Xaa / Glu / Asp / Aib / Ala |
| 40 | Xaa / Ile / Cml / Ala |
| 41 | Xaa / Ile / Ala / Leu / Val / Aib / Gly / Cml / Nle / Nva / Gln / Asn / Phe |

SEQ ID NO:4

| Pos | Residue (alternatives) |
|---|---|
| 25 | Xaa / Gln / Asn / Lys |
| 26 | Xaa / Cml / Leu / Ala |
| 27 | Xaa / Leu / Aib / Lys / Arg |
| 28 | Xaa / Ala / Aib / Lys / Arg |
| 29 | Xaa / Aib / Gln / Gln / Ala |
| 30 | Xaa / cGlu / cAsp |
| 31 | Xaa / *** / Aib / DAla |
| 32 | Xaa / His / Glu / DHis / Leu / Lys / Ala / Aib |
| 33 | Xaa / cLys / cOrn / cDbu / cHly |
| 34 | Xaa / Asn / Aib / Ala |
| 35 | Xaa / Arg / Ala / Lys |
| 36 | Xaa / Lys / Orn / Arg / Har / Cml / Leu / Ala |
| 37 | Xaa / Leu / Cml / Tyr / Ala |
| 38 | Xaa / Nle / Cha / Met / Cml / Phe |
| 39 | Xaa / Glu / Asp / Aib / Ala |
| 40 | Xaa / Ile / Cml / Ala |
| 41 | Xaa / Ile / Ala / Leu / Val / Aib / Gly / Cml / Nle / Nva / Gln / Asn / Phe |

TABLE 1-continued

Exemplary Cyclic CRF Antagonist Peptides

SEQ ID NO:5

| 30 | 31 | 32 | 33 | 34 | 35 | 36 | 37 | 38 | 39 | 40 | 41 |
|---|---|---|---|---|---|---|---|---|---|---|---|
| Xaa | Xaa | Xaa | Xaa | Xaa | Xaa | Xaa | Xaa | Xaa | Xaa | Xaa | Xaa |
| cGlu | *** | His | cLys | Asn | Arg | Lys | Leu | Nle | Glu | Ile | Ile |
| cAsp | Aib | Glu | cOrn | Aib | Ala | Orn | Cml | Cha | Asp | Cml | Ala |
|  | DAla | DHis | cDbu | Ala | Lys | Arg | Tyr | Met | Aib | Ala | Leu |
|  |  | Leu | cHly |  |  | Har | Ala | Cml | Ala |  | Val |
|  |  | Lys |  |  |  | Cml | Phe |  |  |  | Aib |
|  |  | Ala |  |  |  | Leu |  |  |  |  | Gly |
|  |  | Aib |  |  |  | Ala |  |  |  |  | Cml |
|  |  |  |  |  |  |  |  |  |  |  | Nle |
|  |  |  |  |  |  |  |  |  |  |  | Nva |
|  |  |  |  |  |  |  |  |  |  |  | Gln |
|  |  |  |  |  |  |  |  |  |  |  | Asn |
|  |  |  |  |  |  |  |  |  |  |  | Phe |

*** = Any L-alpha-amino acid with the exception of Cys. Residue 41 is amidated.

In some method embodiments, a cyclic CRF antagonist peptide includes (or consists of) a consensus sequence set forth in Table 1 (such as (cyclo30-33)[$M_{13-15}$, $M_{17-41}$]h/rCRF 9-41 (SEQ ID NO: 2); (cyclo30-33)[$M_{15}$, $M_{17-41}$]h/rCRF 15-41 (SEQ ID NO: 3); (cyclo30-33)[$M_{26-41}$]h/rCRF 26-41 (SEQ ID NO: 4); or (cyclo30-33)[$M_{30-41}$]h/rCRF 30-41) (SEQ ID NO: 5), and $R_9$-$R_{29}$, if or as applicable, are as provided in Table 1, $R_{30}$ is Glu or Asp; $R_{31}$ is Ala, Aib, or DAla; $R_{32}$ is His, Glu, DHis, Leu, Lys, or Ala; $R_{33}$ is Lys, Orn, Dbu, Hly; $R_{34}$ is Asn or Ala; $R_{35}$ is Arg, Ala, or Lys; $R_{36}$ is Lys, Orn, Arg, Har, Cml, or Leu; $R_{37}$ is Leu, Cml, or Tyr; $R_{38}$ is Nle, Cha, Cml, or Phe; $R_{39}$ is Glu, Asp, Aib, or Ala; $R_{40}$ is Ile, Cml, or Ala; and $R_{41}$ is Ile, Ala, Leu, Val, Aib, Gly, Cml, Nle, Nva, Gln, or Asn.

In other method embodiments, a cyclic CRF antagonist peptide includes (or consists of) a consensus sequence set forth in Table 1, wherein $R_9$-$R_{29}$, if or as applicable, are as provided in Table 1, $R_{30}$ is Glu; $R_{31}$ is Aib, or DAla; $R_{32}$ is His or Ala; $R_{33}$ is Lys; $R_{34}$ is Asn or Ala; $R_{35}$ is Arg; $R_{36}$ is Lys; $R_{37}$ is Leu or Cml; $R_{38}$ is Nle or Cha; $R_{39}$ is Glu or Asp; $R_{40}$ is Ile, Cml, or Ala; and $R_{41}$ is Ile or Ala. In other instances, $R_9$-$R_{29}$, if or as applicable, are as provided in Table 1, $R_{30}$ is Glu; $R_{31}$ is Ala; $R_{32}$ is His or Ala; $R_{33}$ is Lys or Orn; $R_{34}$ is Asn; $R_{35}$ is Arg; $R_{36}$ is Lys or Cml; $R_{37}$ is Leu or Cml; $R_{38}$ is Met, Nle or Cml; $R_{39}$ is Glu; $R_{40}$ is Ile or Cml; and $R_{41}$ is Ile or Cml, and at least one of $R_{14}$ (if or as applicable), $R_{18}$ (if or as applicable), $R_{36}$, $R_{37}$, $R_{40}$ or $R_{41}$ is Cml.

In still other method embodiments, a cyclic CRF antagonist peptide includes (or consists of) a consensus sequence set forth in Table 1, wherein (if or as applicable) $R_{14}$ is Leu or Cml; $R_{18}$ is Val, Cml or Nle; $R_{20}$ is Glu or DGlu; $R_{22}$ is Ala or Aib; $R_{24}$ is Ala or Aib; $R_{25}$ is Asp or Glu; $R_{28}$ is Ala or Aib; $R_{29}$ is Gln; $R_{30}$ is Glu; $R_{31}$ is Ala or Aib; $R_{32}$ is His, Aib, or DHis; $R_{33}$ is Lys or Orn; $R_{34}$ is Asn or Aib; $R_{35}$ is Arg; $R_{36}$ is Lys or Cml; $R_{37}$ is Leu or Cml; $R_{38}$ is Nle, $R_{39}$ is Glu or Asp; $R_{40}$ is Ile or Cml; $R_{41}$ is Ile, Aib, Cml or Ala; and any other applicable residues are as shown in Table 1.

In yet other method embodiments, a cyclic CRF antagonist peptide includes (or consists of) a consensus sequence set forth in Table 1, wherein (if or as applicable) $R_{11}$ is Thr; $R_{13}$ is H is; $R_{14}$ is Leu or Cml; $R_{15}$ is Leu or Cml, $R_{17}$ is Glu or Cml; $R_{18}$ is Val or Cml; $R_{19}$ is Leu; $R_{20}$ is Glu; $R_{22}$ is Ala; $R_{23}$ is Arg; $R_{24}$ is Ala or Cml; $R_{25}$-$R_{31}$ are, in order (and as applicable) Glu, Gln, Cml, Ala, Gln, Glu, Ala; $R_{32}$ is His, Aib, or DHis; $R_{33}$ is Lys or Orn; $R_{36}$ is Lys or Cml; $R_{37}$ is Leu or Cml; $R_{38}$ is Met, Nle or Cml; $R_{40}$ and $R_{41}$ are independently Ile or Cml; any other applicable residues are is shown in Table 1; and at least one of $R_{10}$ (AS applicable), $R_{14}$ (is applicable), $R_{15}$ (as applicable), $R_{17}$ (as applicable), $R_{18}$ (as applicable), $R_{19}$ (as applicable), $R_{37}$, $R_{40}$ and $R_{41}$ Cml.

In some method embodiments, a cyclic CRF antagonist peptide has Formula I:

(SEQ ID NO: 6)
(cyclo 30-33)Y-Asp-$R_{10}$-$R_{11}$-DPhe-$R_{13}$-$R_{14}$-$R_{15}$-Arg- $R_{17}$-$R_{18}$-$R_{19}$-$R_{20}$-$R_{21}$-$R_{22}$-$R_{23}$-$R_{24}$-$R_{25}$-$R_{26}$-Cml-$R_{28}$-

$R_{29}$-Glu-$R_{31}$-$R_{32}$-$R_{33}$-$R_{34}$-Arg-$R_{36}$-$R_{37}$-$R_{38}$-$R_{39}$-$R_{40}$-

$R_{41}$-$NH_2$ wherein Y is an acyl group having up to 15 carbon atoms; $R_{10}$ is Leu or Cml; $R_{11}$ is Thr or Ser; $R_{13}$ is His, Tyr or Glu; $R_{14}$ is Cml or Leu; $R_{15}$ is Leu or Cml; $R_{17}$ is Glu, Cml, Asn or Lys; $R_{18}$ is Val, Nle, Cml or Met; $R_{19}$ is Leu or Ile; $R_{20}$ is Glu, DGlu, or His; $R_{21}$ is Nle or Met; $R_{22}$ is Ala, DAla, Aib, Asp, Thr, DThr, Glu or DGlu; $R_{23}$ is Arg or Lys; $R_{24}$ is Ala, Aib or Cml; $R_{25}$ is Glu or Asp; $R_{26}$ is Gln, Asn or Lys; $R_{28}$ is Ala, Lys, Aib or Arg; $R_{29}$ is Gln, Aib or Glu; $R_{31}$ is Aib or an L-isomer of an α-amino acid other than Cys; $R_{32}$ is Aib or a D- or L-isomer of an α-amino acid other than Cys; $R_{33}$ is Lys or Orn; $R_{34}$ is Asn or Aib; $R_{36}$ is Lys, Orn, Arg, Har, Cml or Leu; $R_{37}$ is Cml, Leu or Tyr; $R_{38}$ is Nle, Met or Cml; $R_{39}$ is Glu, Aib or Asp; $R_{40}$ is Cml, Ile, Aib, Thr, Asn, Glu, Ala, Val, Leu, Nle, Phe, Nva, Gly or Gln; and $R_{41}$ is Ala, Aib, Ile, Gly, Val, Leu, Cml, Nle, Phe, Nva or Gln; wherein DPhe12 may be substituted by another D-amino acid, such as DLeu, DTyr, DTrp, DCpa, DTrp, DNal or DPal, or by Phe or Tyr. In some method embodiments, DPhe12 as described in this paragraph or elsewhere in the specification may be substituted by another D-amino acid, such as DLeu, DTyr, DTrp, DCpa, DTrp, DNal or DPal, or by Phe or Tyr and the like, including halogenated, methylated, and/or methoxylated aromatic rings.

In particular method embodiments, a cyclic CRF antagonist peptide is as previously described for Formula I, except $R_{32}$ is Aib and $R_{40}$ is Cml. In other embodiments, a cyclic CRF antagonist peptide is as previously described for Formula I, except $R_{18}$ is Val, $R_{22}$ is Ala, $R_{23}$ is Arg, $R_{24}$ is Ala, $R_{25}$ is Glu, $R_{28}$ is Ala, $R_{32}$ is Aib, $R_{39}$ is Glu, $R_{40}$ is Cml, and $R_{41}$ is Ile. Still other methods involve particular cyclic CRF peptide antagonists of Formula I as follows: (cyclo 30-33) Y-Asp-Leu-Thr-DPhe-His-Leu-Leu-Arg-Glu-Val-Leu-Glu-Nle-Ala-Arg-Ala-Glu-Gln-Cml-Ala-Gln-Glu-Ala-Aib-Lys-Asn-Arg-Lys-Leu-Nle-Glu-Cml-Ile-$NH_2$ (SEQ ID NO: 6), wherein Y is any acyl group having not more than 12 carbon atoms.

In other examples of peptides having Formula I, the Leu residue in the 27 position is substituted with a methyl group on its α-carbon atom, i.e., Cml. Cml may optionally also be present in the 10, 14, 15, 17, 18, 24, 36, 37, 38, 40 and/or 41 positions. In other particular examples, $R_{27}$ is Cml and at least one more Cml residue is found in the cyclic CRF antagonist peptide. In still other examples, residues 19 and 21 are Cml. CαMeAla, which is also known as α-aminoisobutyric acid (Aib), may also optionally be at one or more of residues 22, 24, 28, 29, 31, 32, 34, 39, 40 and/or 41. The foregoing cyclic CRF antagonist peptides are believed to have enhanced biopotency and/or increased duration of action as compared to astressin (Gulyas et al., *Proc. Natl. Acad. Sci.*, 92.10575-10579, 1995). For example, the combination of Cml27 with one or more of Cml18, and Cml40 and/or with one or more of Aib22, Aib24, Aib28, Aib31 and Aib32 (together with the 30-33 side chain bridge) has been shown to provide long duration of bioactivity (e.g., U.S. Pat. No. 6,323,312).

In other exemplary methods, cyclic CRF peptide antagonists have Formula I, wherein wherein Y is an acyl group having up to 15 carbon atoms; $R_{10}$ is Leu or Cml; $R_{11}$ is Thr or Ser; $R_{13}$ is His, Tyr or Glu; $R_{14}$ is Cml or Leu; $R_{15}$ is Leu or Cml; $R_{17}$ is Glu Cml, Asn or Lys; $R_{18}$ is Val, Nle, Cml or Met; $R_{19}$ is Leu or Ile; $R_{20}$ is Glu, D-Glu, or His; $R_{21}$ is Nle or Met; $R_{22}$ is Ala, D-Ala, Aib, Asp, Thr, D-Thr, Glu or D-Glu; $R_{23}$ is Arg or Lys; $R_{24}$ is Ala, Aib or Cml; $R_{25}$ is Glu or Asp; $R_{26}$ is Gln, Asn or Lys; $R_{28}$ is Ala, Lys, Aib or Arg; $R_{29}$ is Gln, Aib or Glu; $R_{31}$ is Aib or an L-isomer of an α-amino acid other than Cys; $R_{32}$ is Aib or a D- or L-isomer of an α-amino acid other than Cys; $R_{33}$ is Lys or Orn; $R_{34}$ is Asn or Aib; $R_{36}$ is Lys, Orn, Arg, Har, Cml or Leu; $R_{37}$ is Cml, Leu or Tyr; $R_{38}$ is Nle, Met or Cml; $R_{39}$ is Glu, Aib or Asp; $R_{40}$ is Cml, Ile, Aib, Thr, Asn, Glu, Ala, Val, Leu, Nle, Phe, Nva, Gly or Gln; and $R_{41}$ is Ala, Aib, Ile, Gly, Val, Leu, Cml, Nle, Phe, Nva or Gln; wherein D-Phe12 may be substituted by another D-amino acid, such as D-Leu, D-Tyr, D-Trp, D-Cpa, D-Trp, D-Nal or D-Pal, or by Phe or Tyr; provided, however, that either $R_{18}$ or $R_{40}$ is Cml and that at least one of $R_{22}$, $R_{24}$, $R_{28}$, $R_{31}$ and $R_{32}$ is Aib. In more particular examples, $R_{32}$ and $R_{41}$ are Aib and other residues are as provided in this paragraph.

Other exemplary cyclic CRF peptide antagonists useful in a disclosed method have Formula II:

(SEQ ID NO: 7)
(cyclo 30-33)Y-Asp-Leu-Thr-$R_{12}$-His-$R_{14}$-Leu-Arg-

Glu-$R_{18}$-$R_{19}$-$R_{20}$-$R_{21}$-$R_{22}$-$R_{23}$-$R_{24}$-$R_{25}$-Gln-Cml-$R_{28}$-

Gln-Glu-$R_{31}$-$R_{32}$-$R_{33}$-$R_{34}$-Arg-$R_{36}$-$R_{37}$-Nle-$R_{39}$-$R_{40}$-

$R_{41}$-NH$_2$ wherein Y is an acyl group having not more than 7 carbon atoms; $R_{12}$ is DPhe or D2Nal; $R_{14}$ is Leu or Cml; $R_{18}$ is Val, Cml or Nle; $R_{19}$ is Leu or Ile; $R_{20}$ is Glu or DGlu; $R_{21}$ is Nle or Met; $R_{22}$ is Ala, DAla, Aib or Thr; $R_{23}$ is Arg or Lays; $R_{24}$ is Ala or Aib; $R_{25}$ is Asp or Glu; $R_{28}$ is Ala or Aib; $R_{31}$ is Ala or Aib, $R_{32}$ is Aib, DHis, imBzl-DHis, DArg, D2Nal, or a D-isomer of another basic and/or aromatic α-amino acid; $R_{33}$ is Lys or Orn; $R_{34}$ is Aib or Asn; $R_{36}$ is Lys or Cml; $R_{37}$ is Leu or Cml; $R_{39}$ is Glu or Asp; $R_{40}$ is Ile, Cml or Aib; and $R_{41}$ is Ala, Aib, Cml or Ile.

In particular examples of peptides having Formula II, $R_{12}$ is DPhe, $R_{32}$ is Aib, and $R_{40}$ is Cml and all other residues are as previously described for Formula II.

Generally, in peptides having Formula II, DPhe12 may be substituted by another D-amino acid, such as DLeu, DTyr, DCpa, DNal, DTrp or DPal, or by Phe or Tyr. As an alternative to acylation at the N-terminus, a sulfonamide may be formed, or a sugar or a lipid can be added to modulate hydrophilicity and therefore duration of action and solubility. There is wide latitude for selection of the residue in position 32, and examples of suitable additional residues for $R_{32}$ include the D- and L-isomers of Asn, Trp, Arg, Nal, imBzl-His, Tyr, Ala, Leu, Val, Ser, Thr, Cpa, Pal, Lys, Phe and Gln, as well as Aib, Gly, D-Dpr(Nic), DAph, DAgl(Nic), DOrn, D-Dbu, D-Dpr, or DOrn(Nic). Other examples of suitable residues for $R_{32}$ include the D- and L-isomers of Asn, Trp, Arg, Nal, imBzl-His, Tyr, Ala, Leu, Val, Ser, Thr, Cpa, Pal, Lys, Phe and Gln, as well as Aib, Gly, D-Dpr(Nic), DAph, DAgl(Nic), DOrn, D-Dbu, D-Dpr, DOrn(Nic) and the like, including halogenated, methylated, and/or methoxylated aromatic rings.

Yet other representative cyclic CRF peptide antagonists useful in the disclosed methods have the following Formula III:

(SEQ ID NO: 8)
(cyclo 30-33)Y-Asp-Leu-Thr-DPhe-His-$R_{14}$-Leu-Arg-

Glu-$R_{18}$-Leu-$R_{20}$-Nle-$R_{22}$-$R_{23}$-$R_{24}$-$R_{25}$-Gln-Cml-$R_{28}$-

$R_{29}$-Glu-$R_{31}$-$R_{32}$-$R_{33}$-$R_{34}$-Arg-$R_{36}$-$R_{37}$-Nle-$R_{39}$-$R_{40}$-

$R_{41}$-NH$_2$ wherein Y is Ac, Acr or For; $R_{14}$ is Leu or Cml; $R_{18}$ is Val, Cml or Nle; $R_{20}$ is Glu or DGlu; $R_{22}$ is Ala, Aib, DAla or Thr; $R_{23}$ is Arg or Lys; $R_{24}$ is Ala or Aib; $R_{25}$ is Asp or Glu; $R_{28}$ is Ala or Aib; $R_{29}$ is Gln or Glu; $R_{31}$ is Ala or Aib; $R_{32}$ is Aib, His, DHis, DArg, imBzl-DHis, DNal, DGlu, DAla, DPal, DTrp, D-Dpr(Nic), DAph, DAgl(Nic), DOrn, D-Dbu, D-Dpr or DOrn(Nic); $R_{33}$ is Lys or Orn; $R_{34}$ is Asn or Aib; $R_{36}$ is Lys, Cml or Leu; $R_{37}$ is Leu or Cml; $R_{39}$ is Glu or Asp; $R_{40}$ is Ile, Cml, Aib or Glu; and $R_{41}$ is Ile, Aib, Cml or Ala; provided that D2Nal or DLeu or Phe may be substituted for DPhe.

In particular examples of peptides having Formula III, $R_{32}$ is Aib, and $R_{40}$ is Cml and all other residues are as previously described for Formula III.

In other examples of peptides having Formula III, Y is Ac, Acr or For; $R_{14}$ is Leu or Cml; $R_{18}$ is Val; $R_{20}$ is Glu or DGlu; $R_{22}$ is Ala, $R_{23}$ is Arg; $R_{24}$ is Ala, $R_{25}$ is Glu; $R_{28}$ is Ala; $R_{29}$ is Gln or Glu; $R_{31}$ is Ala or Aib; $R_{32}$ is His, DHis, DArg, imBzl-DHis, DNal, DGlu, DAla, DPal, DTrp, D-Dpr (Nic), DAph, DAgl(Nic), DOrn, D-Dbu, D-Dpr or DOrn (Nic); $R_{33}$ is Lys or Orn; $R_{34}$ is Asn or Aib; $R_{36}$ is Lys, Cml or Leu; $R_{37}$ is Leu or Cml; $R_{39}$ is Glu; $R_{40}$ is Ile, Cml, Aib or Glu; and $R_{41}$ is Ile; provided that D2Nal or DLeu or Phe may be substituted for DPhe.

Still other representative cyclic CRF peptide antagonists useful in the disclosed methods have the following Formula IV (SEQ ID NO: 9):

(SEQ ID NO: 9)
(cyclo 30-33)Y-Asp-$R_{10}$-Thr-$R_{12}$-His-$R_{14}$-$R_{15}$-Arg- $R_{17}$-$R_{18}$-Leu-Glu-$R_{21}$-Ala-$R_{23}$-$R_{24}$-Glu-Gln-Cml-Ala- Gln-Glu-Ala-$R_{32}$-$R_{33}$-Asn-Arg-$R_{36}$-$R_{37}$-$R_{38}$-Glu-$R_{40}$-

$R_{41}$-NH$_2$ wherein Y is Ac, For or Acr; $R_{10}$ is Leu or Cml; $R_{12}$ is DPhe or D2Nal; $R_{14}$, $R_{15}$, and $R_{37}$ are independently Leu or Cml; $R_{17}$ is Glu or Cml; $R_{18}$ is Val or Cml; $R_{21}$ is Met or Nle; $R_{23}$ is Arg or Lys; $R_{24}$ is Ala or Cml; $R_{32}$ is Aib, His, DHis, imBzl-DHis, DArg, DAsn, DTyr, DPal, DNal, DTrp or another basic and/or aromatic D-isomer α-amino acid; $R_{33}$ is Lys or Orn; $R_{36}$ is Lys or Cml; $R_{38}$ is Met, Nle or Cml; and $R_{40}$ and $R_{41}$ are independently Ile or Cml; and wherein at least one of $R_{14}$, $R_{18}$, $R_{36}$, $R_{37}$, and $R_{41}$ is Cml.

In some methods, cyclic CRF peptide antagonists are as previously described for Formula IV, except $R_{12}$ is DPhe $R_{32}$ is Aib, and $R_{40}$ is Cml.

In other methods, cyclic CRF peptide antagonists have Formula IV, wherein Y is Ac, For or Acr; $R_{10}$ is Leu or Cml; $R_{12}$ is DPhe, $R_{14}$, $R_{15}$, and $R_{37}$ are independently Leu or Cml; $R_{17}$ is Glu or Cml; $R_{18}$ is Cml, $R_{21}$ is Met or Nle; $R_{23}$ is Arg; $R_{24}$ is Ala or Cml; $R_{32}$ is Aib; $R_{33}$ is Lys or Orn; $R_{36}$ is Lys or Cml; $R_{38}$ is Met, Nle or Cml; $R_{40}$ is Cml; and $R_{41}$ is Ile or Cml.

Some method embodiments involve cyclic CRF peptide antagonists having the following Formula V:

(SEQ ID NO: 10)
(cyclo 30-33)Y-Asp-$R_{10}$-Thr-$R_{12}$-His-$R_{14}$-$R_{15}$-Arg- $R_{17}$-$R_{18}$-Leu-Glu-$R_{21}$-$R_{22}$-$R_{23}$-$R_{24}$-Glu-Gln-Cml-$R_{28}$-

$R_{29}$-Glu-$R_{31}$-$R_{32}$-$R_{33}$-$R_{34}$-Arg-$R_{36}$-$R_{37}$-$R_{38}$-$R_{39}$-$R_{40}$-

$R_{41}$-NH$_2$ wherein Y is an acyl group having up to 15 carbon atoms; $R_{10}$, $R_{14}$, $R_{15}$, and $R_{37}$ are independently Leu or Cml; $R_{12}$ is DPhe or D2Nal; $R_{17}$ is Glu or Cml; $R_{18}$ is Val or Cml; $R_{21}$ is Met or Nle; $R_{22}$, $R_{28}$, and $R_{31}$ are independently either Ala or Aib; $R_{23}$ is Arg or Lys; $R_{24}$ is Ala, Aib or Cml; $R_{29}$ is Gln or Aib; $R_{32}$ is His, Aib, DHis, imBzl-DHis, DArg, DAsn, DTyr, DPal, DNal, DTrp or another basic and/or aromatic D-isomer α-amino acid; $R_{33}$ is Lys or Orn; $R_{34}$ is Asn or Aib; $R_{36}$ is Lys or Cml; $R_{38}$ is Met, Nle or Cml; $R_{39}$ is Glu or Aib; and $R_{40}$ is Ile, Cml or Aib; $R_{41}$ is Leu, Cml or Aib; and wherein at least one of $R_{22}$, $R_{24}$, $R_{28}$, and $R_{31}$ is Aib.

Particular methods involve cyclic CRF peptide antagonists as previously described for Formula V, except $R_{12}$ is DPhe, $R_{32}$ is Aib, and $R_{40}$ is Cml. More particular methods involve cyclic CRF peptide antagonists as previously described for Formula V, except $R_{12}$ is DPhe, $R_{32}$ is Aib, $R_{40}$ is Cml, and at least one of $R_{14}$, $R_{18}$, or $R_{37}$ is Cml.

In other exemplary methods, cyclic CRF peptide antagonists have Formula V, wherein Y is an acyl group having up to 15 carbon atoms; $R_{10}$, $R_{14}$, $R_{15}$, and $R_{37}$ are independently Leu or Cml; $R_{12}$ is DPhe, $R_{17}$ is Glu or Cml; $R_{18}$ is Val or Cml; $R_{21}$ is Met or Nle; $R_{22}$, $R_{28}$ and $R_{31}$ are independently either Ala or Aib; $R_{23}$ is Arg or Lys; $R_{24}$ is Ala, Aib or Cml; $R_{29}$ is Gln or Aib; $R_{32}$ is His, Aib, DHis, imBzlD-His, DArg, DAsn, DTyr, DPal, DNal, DTrp or another basic and/or aromatic D-isomer α-amino acid; $R_{33}$ is Lys or Orn; $R_{34}$ is Asn or Aib; $R_{36}$ is Lys or Cml, $R_{38}$ is Met, Nle or Cml; $R_{39}$ is Glu or Aib; $R_{40}$ is Cml, Ile or Aib; and $R_{41}$ is Leu, Cml or Aib; provided that either $R_{18}$ or $R_{40}$ is Cml and that at least one of $R_{22}$, $R_{24}$, $R_{28}$, and $R_{31}$ is Aib.

Cyclic CRF peptide antagonists that are functional fragments of any of Formula I, II, III, IV or V are also contemplated for use in a disclosed method.

Further exemplary cyclic CRF peptide antagonists useful in the disclosed methods have the following formula:

(SEQ ID NO: 11)
(cyclo 30-33)Y-Asp-Leu-Thr-DPhe-His-$R_{14}$-Leu-Arg-

Glu-$R_{18}$-Leu-$R_{20}$-Nle-$R_{22}$-Arg-$R_{24}$-$R_{25}$-Gln-Cml-$R_{28}$-

Gln-Glu-$R_{31}$-$R_{32}$-$R_{33}$-$R_{34}$-Arg-$R_{36}$-$R_{37}$-Nle-$R_{39}$-$R_{40}$-

$R_{41}$-NH$_2$ wherein Y is Ac, Acr or For; $R_{14}$ is Leu or Cml; $R_{18}$ is Val, Cml or Nle; $R_{20}$ is Glu or DGlu; $R_{22}$ is Ala or Aib; $R_{24}$ is Ala or Aib; $R_{25}$ is Asp or Glu; $R_{28}$ is Ala or Aib; $R_{31}$ is Ala or Aib; $R_{32}$ is His, Aib, DHis, DArg, DNal, DGlu, DAla, DPal, DTrp, DAph, DOrn, D-Dbu or D-Dpr; $R_{33}$ is Lys or Orn; $R_{34}$ is Asn or Aib; $R_{36}$ is Lys or Cml; $R_{37}$ is Leu or Cml; $R_{39}$ is Glu or Asp; $R_{40}$ is Ile, Cml or Aib; and $R_{41}$ is Ile, Aib, Cml or Ala; provided that D2Nal or DLeu or Phe may be substituted for DPhe.

Other method embodiments involve exemplary cyclic CRF peptide antagonists having the formula:

(SEQ ID NO: 12)
(cyclo 30-33)Y-Asp-$R_{10}$-Thr-$R_{12}$-His-$R_{14}$-$R_{15}$-Arg- $R_{17}$-$R_{18}$-Leu-Glu-$R_{21}$-Ala-Arg-$R_{24}$-Glu-Gln-Cml-Ala- Gln-Glu-Ala-$R_{32}$-$R_{33}$-Asn-Arg-$R_{36}$-$R_{37}$-$R_{38}$-Glu-$R_{40}$-

$R_{41}$-NH$_2$ wherein Y is Ac, For or Acr; $R_{10}$ is Leu or Cml; $R_{12}$ is DPhe or D2Nal; $R_{14}$, $R_{15}$, and $R_{37}$ are independently Leu or Cml; $R_{17}$ is Glu or Cml; $R_{18}$ is Val or Cml; $R_{21}$ is Met or Nle; $R_{24}$ is Ala or Cml; $R_{32}$ is His, Aib, DHis, imBzl-DHis, DArg, DAsn, DTyr, DPal, DNal, DTrp or another basic and/or aromatic D-isomer α-amino acid; $R_{33}$ is Lys or Orn; $R_{36}$ is Lys or Cml; $R_{38}$ is Met, Nle or Cml; and $R_{40}$ and $R_{41}$ are independently Ile or Cml; and wherein at least one of $R_{10}$, $R_{14}$, $R_{15}$, $R_{17}$, $R_{19}$, $R_{37}$, $R_{40}$ and $R_{41}$ is Cml.

Still other method embodiments involve cyclic CRF peptide antagonists having the formula:

(SEQ ID NO: 13)
(cycle 30-33)Y-Asp-Leu-Thr-$R_{12}$-$R_{13}$-$R_{14}$-$R_{15}$-Arg-$R_{17}$-

$R_{18}$-Leu-$R_{20}$-Nle-$R_{22}$-$R_{23}$-$R_{24}$-$R_{25}$-$R_{26}$-Cml-$R_{28}$-$R_{29}$-

Glu-$R_{31}$-$R_{32}$-$R_{33}$-$R_{34}$-Arg-$R_{36}$-$R_{37}$-Nle-$R_{39}$-$R_{40}$-$R_{41}$-NH$_2$ wherein Y is an acyl group having not more than 7 carbon atoms; $R_{12}$ is DPhe, DLeu, D2Nal or DTyr; $R_{13}$ is His, Tyr or Glu; $R_{14}$ is Leu or Cml; $R_{15}$, is Leu or Cml; $R_{17}$ is Glu or Cml; $R_{18}$ is Val, Cml, Nle or Met; $R_{20}$ is Glu or DGlu; $R_{22}$ is Ala, DAla, Aib, Thr, Asp or Glu; $R_{23}$ is Arg or Lys; $R_{24}$ is Ala, Aib or Cml; $R_{25}$ is Asp or Glu; $R_{26}$ is Gln, Asn or Lys; $R_{28}$ is Ala or Aib; $R_{29}$ is Gln, Aib or Glu; $R_{31}$ is Ala or Aib; $R_{32}$ is His, DHis, Aib, DArg, D2Nal, D3Pal, DTrp, imBzl-DHis, Gly, Tyr, DTyr, Leu, DLeu, Ala or DAla; $R_{33}$ is Lys or Orn; $R_{34}$ is Asn or Aib; $R_{36}$ is Lys, Orn, Arg, Har, Cml or Leu; $R_{37}$ is Cml, Leu or Tyr; $R_{39}$ is Glu, Aib or Asp; $R_{40}$ is Ile, Cml, Aib, Thr, Glu, Asn or Gln; and $R_{41}$ is Ala, Aib, Ile, Cml, Val or Phe, provided that at least one of $R_{18}$ and $R_{40}$ Cml.

Yet other exemplary methods involve cyclic CRF peptide antagonists having one of the following formulas:

(SEQ ID NO: 14)
(cyclo 30-33)Y-Asp-$R_{10}$-Thr-$R_{12}$-His-$R_{14}$-$R_{15}$-Arg-$R_{17}$-

$R_{18}$-Leu-Glu-$R_{21}$-Ala-Arg-$R_{24}$-Glu-Gln-Cml-Ala-Gln-

Glu-Ala-$R_{32}$-$R_{33}$-Asn-Arg-$R_{36}$-$R_{37}$-$R_{38}$-Glu-$R_{40}$-$R_{41}$-NH$_2$ wherein Y is Ac, For or Acr; $R_{10}$ is Leu or Cml; $R_{12}$ is DPhe or D2Nal; $R_{14}$, $R_{15}$, and $R_{37}$ are independently Leu or Cml; $R_{17}$ is Glu or Cml; $R_{18}$ is Val or Cml; $R_{21}$ is Met or Nle; $R_{24}$ is Ala or Cml; $R_{32}$ is His, DHis, imBzl-DHis, DArg, DAsn, DTyr, DPal, DNal, DTrp or another basic and/or aromatic D-isomer α-amino acid; $R_{33}$ is Lys or Orn; $R_{36}$ is Lys or Cml; $R_{38}$ is Met, Nle or Cml; and $R_{40}$ and $R_{41}$ are independently Ile or Cml; and wherein at least one of $R_{18}$ and $R_{40}$ is Cml; or (SEQ ID NO: 15)
(cyclo 30-33)Y-Asp-Leu-Thr-$R_{12}$-His-Leu-Leu-Arg-Glu- Val-Leu-Glu-Nle-Ala-$R_{23}$-Ala-Glu-Gln-Cml-Ala-Gln- Glu-Ala-His-$R_{33}$-Asn-Arg-Lys-Leu-Nle-Glu-Ile-Ile-NH$_2$ wherein Y is Ac or Acr; $R_{12}$ is DPhe or D2Nal; $R_{23}$ is Arg or Lys; $R_{33}$ is Lys or Orn; and wherein His32 may optionally be substituted by DHis, imBzl-DHis, DArg, DTyr, DNal, DPal, DTrp, DAsn DLys, D-Dpr(Nic), DAph, DPhe, DCpa, DAgl(Nic), DOrn D-Dbu D-Dpr or DOrn(Nic).

Other exemplary cyclic CRF antagonist peptides useful in a disclosed method (where Ac is an acetyl group and, in each case, the C-terminal residue is amidated) are: (cyclo 30-33) [Glu30,32, Aib31, Lys33, Cha38, Asp39] Ac-h/rCRF(30-41); (cyclo 30-33)[Glu30,32, Aib31 Lys33, Cha38, Asp39, Cml40] Ac-h/rCRF(30-41); (cyclo 30-33)[DPhe12, Nle21,38, Cml27,40, Glu30, Aib31, Lys33] Ac-h/rCRF(9-41); (cyclo 30-33)[DPhe12, Nle21,38, Aib22, Cml27,40, Glu30, Lys33] Ac-h/rCRF(9-41); (cyclo 30-33)[DPhe12, Nle21,38, Aib24, Cml27,40, Glu30, Lys33] Ac-h/rCRF(9-41); (cyclo 30-33)[DPhe12, Nle21,38, Cml27,40, Aib28, Glu30, Lys33] Ac-h/rCRF(9-41); (cyclo 30-33)[DPhe12, Nle21,38, Glu30, Lys33] Ac-h/rCRF(12-41); (cyclo 30-33)[DPhe12, Nle21, 38, Cml27,40, Glu30, Lys33]Ac-h/rCRF(10-41); (cyclo 30-33)[DPhe12, Nle21,38, Cml27,40, Glu30, Lys33]Ac-h/ rCRF(11-41); (cyclo 30-33)[DPhe12, Nle21,38, Cml27,40, Glu30, Lys33]Ac-h/rCRF(12-41); (cyclo 30-33)[Nle21,38, Cml27,40, Glu30, Lys33]Ac-h/rCRF(13-41); (cyclo 30-33) [Nle21.38, Cml27,40, Glu30, Lys33]Ac-h/rCRF(14-41); (cyclo 30-33)[Nle21,38, Cml27,40, Glu30, Lys33]Ac-h/ rCRF(15-41); (cyclo 30-33)[Nle21,38, Cml27,40, Glu30, Lys33]Ac-h/rCRF(16-41); (cyclo 30-33)[Nle21,38, Cml27, 40, Glu30, Lys33]Ac-h rCRF(17-41); (cyclo 30-33)[Nle21, 38, Cml27,40, Glu30, Lys33]Ac-h/rCRF(18-41); (cyclo 30-33)[Nle21,38, Cml27,40, Glu30, Lys33]Ac-h/rCRF(19-41); (cyclo 30-33)[Nle21,38, Cml27,40, Glu30, Lys33]Ac-h/rCRF(20-41); (cyclo 30-33)[Nle21,38, Cml27,40, Glu30, Lys33]Ac-h/rCRF(21-41); (cyclo 30-33)[Cml27,40, Glu30, Lys33, Nle38]Ac-h/rCRF(22-41); (cyclo 30-33)[Cml27,40, Glu30, Lys33, Nle38]Ac-h/rCRF(23-41); (cyclo 30-33) [Cml27,40, Glu30, Lys33, Nle38]Ac-h/rCRF(24-41); (cyclo 30-33)[Cml27,40, Glu30, Lys33, Nle38]Ac-h/rCRF(25-41); (cyclo 30-33)[Cml27,40, Glu30, Lys33, Nle38]Ac-h/rCRF (26-41); (cyclo 30-33)[Cml27,40, Glu30, Lys33, Nle38]Ac-h/rCRF(27-41); (cyclo 30-33)[Glu30, Lys33, Nle38, Cml40] Ac-h/rCRF(28-41); (cyclo 30-33)[Glu30, Lys33, Nle38, Cml40]Ac-h/rCRF(29-41); (cyclo 30-33)[Glu30, Lys33, Nle38, Cml40]Ac-h/rCRF(30-41); (cyclo 30-33)[DPhe12, Cml14,27, Nle21,38, Glu30, DHis32, Lys33]Ac-h/rCRF(9-41); (cyclo 30-33)[DPhe12, Cml18,27, Nle21,38, Glu30, DHis32, Lys33]Ac-h/rCRF(9-41); (cyclo 30-33)[DPhe12, Nle21,38, Cml27,36,37, Glu30, Lys33]Ac-h/rCRF(9-41); (cyclo 30-33)[DPhe12, Nle21,38, Cml27,40 Glu30, Lys33] Ac-h/rCRF(9-41); (cyclo 30-33)[DPhe12, Nle21,38, Cml27, 37, Glu30, Lys33]Ac-h/rCRF(9-41); (cyclo 30-33)[DPhe12, Cml14,27,40, Nle21,38, Glu30, Lys33]Ac-h/rCRF(9-41); (cyclo 30-33)[DPhe12, Nle21,38 Cml14,27,37,40, Glu30, Lys33]Ac-h/rCRF(9-41); (cyclo 30-33)[D2Nal12, Cml14, 27,37,40, Nle21,38, Glu30, Lys33]Ac-h rCRF(9-41); (cyclo 30-33)[DPhe12, Nle21,38, Cml27,37,40, Glu30, Lys33]Ac-h/rCRF(9-41); (cyclo 30-33)[DPhe12, Nle21,38, Aib24, Cml27,40, Glu30, Lys33]Ac-h/rCRF(9-41); (cyclo 30-33) [DPhe12, Nle21,38, Cml27, Aib28, Glu30, Lys33]Ac-h/r CRF(9-41); (cyclo 30-33)[DPhe12, Nle21,38, Cml27,40, Aib28, Glu30, Lys33]Ac-h/rCRF(9-41); (cyclo 30-33) [DPhe12, Nle21,38, Cml27,37, Aib28,31, Glu30, Lys33]Ac-h/rCRF(9-41); (cyclo 30-33)[DPhe12, Nle21,38, Cml27,40, Glu30, Aib32, Lys33]Ac-h/rCRF(9-41); (cyclo 30-33) [DPhe12, Cml14,27, Nle21,38, Glu30, Aib31, Lys33]Ac-h/ rCRF(9-41); (cyclo 30-33)[DPhe12, Nle21,38, Cml27, Glu30, DHis32, Lys33]Ac-h/rCRF(9-41); (cyclo 30-33) [DPhe12, Cml14,27, Nle21,38, Glu30, Lys33]Ac-h/rCRF(9-41); (cyclo 30-33)[DPhe12, Cml18,27, Nle21,38, Glu30 Lys33]Ac-h/rCRF(9-41); (cyclo 30-33)[DPhe12, Nle21,38, Cml27,36, Glu30, Lys33]Ac-h/rCRF(9-41); (cyclo 30-33) [DPhe12, Nle21,38, Cml27,37, Glu30, Lys33]Ac-h/rCRF(9-41); (cyclo 30-33)[DPhe12, Nle21,38, Cml27,40, Glu30, Lys33]Ac-h/rCRF(9-41); (cycle 30-33)[DPhe12, Nle21,38, Cml27,41, Glu30, Lys33]Ac-h/rCRF(9-41); (cycle 30-33) [Cml10,27, DPhe12, Nle21,38, Glu30, Lys33]Ac-h/rCRF(9-41); (cyclo 30-33)[DPhe12, Cml15,27, Nle21,38, Glu30, Lys33]Ac-h/rCRF(9-41); (cyclo 30-33)[DPhe12, Cml19,27, Nle21,38, Glu30, Lys33]Ac-h/rCRF(9-41); (cyclo 30-33) [DPhe12, Nle21,38, Cml24,27, Glu30, Lys33]Ac-h/rCRF(9-41); (cyclo 30-33)[DPhe12, Cml14,27,37,40, Nle21,38, Glu30, Lys33]Ac-h/rCRF(9-41); (cyclo 30-33)[D2Nal12, Cml14,27,37,40, Nle21,38, Glu30, Lys33]Ac-h/rCRF(9-41); (cyclo 30-33)[DPhe12, Nle21,38, Cml27,37,40, Glu30, Lys33]Ac-h/rCRF(9-41); (cyclo 30-33)[DPhe12, Cml17,27, Nle21,38, Glu30, Lys33]Ac-h/rCRF(9-41); (cyclo 30-33) [D2Nal12, Cml17,27, Nle21,38, Glu30, Lys33]Ac-h/rCRF (9-41); (cyclo 30-33)[DPhe12, Cml15,27, Nle21,38, Glu30, Aib32, Lys33]Ac-h/rCRF(9-41); (cyclo 30-33)[DPhe12, Cml21,27, Glu30, Aib32, Lys33, Nle38]Ac-h/rCRF(9-41); (cyclo) 30-33)[DPhe12, Nle21, Cml27,38, Glu30, Lys33] Ac-h/rCRF(9-41); (cyclo 30-33)[DPhe12, Nle21,38, Cml27, 40, Glu30, Aib32, Lys33]Ac-h/rCRF(9-41); (cyclo 30-33) [DPhe12, Nle21,38, Cml27, Glu30, Orn33]Ac-h/rCRF(9-41); (cyclo 30-33)[DPhe12, Nle21,38, Cml27,40, Glu30, Aib32, Orn33]Ac-h/rCRF(9-41); (cyclo 30-33)[DPhe12, Cml14,27, Nle21,38, Glu30, DTrp32, Lys33]Bz-h/rCRF(9-41); (cyclo 30-33)[Ser11, DPhe12, Cml14,27, Nle21,38, Glu30, Lys33]Acr-h/rCRF(9-41); (cyclo 30-33)(DLeu12, Cml17,27, Glu30, Lys33]Acr-h/rCRF(9-41); (cyclo 30-33) [DPhe12, Cml15,27, Nle21,38, Arg28, Glu30, Lys33]Nph-h/rCRF(9-41); (cyclo 30-33)[DPhe12, Cml14,27, Nle21,38, Glu30, DTrp32, Lys33]Bz-h/rCRF(9-41); (cyclo 30-33) [DPhe12, Cml27,37, Nle21,38, Glu30, Lys33]Vac-h/rCRF (9-41); (cyclo 30-33)[DPhe12, Cml27,37, Glu30, DTrp32, Lys33, Aib28]Nph-h/rCRF(9-41); (cyclo 30-33)[Cml27,37, Nle21,38, Glu30, Lys33]Bz-h/rCRF(9-41); (cyclo 30-33) [DPhe12, Cml14,27, Glu30, Aib32, Lys33]For-h/rCRF(9-41); (cyclo 30-33)[DPhe12, Cml14,27, Nle21,38, Lys28,33, Glu30]Vl-h/rCRF(9-41); (cyclo 30-33)[Ser11, DPhe12, Nle21,38, Cml27,40, Glu30, Aib32, Lys33]Flu-h/rCRF(9-41); (cyclo 30-33)[DPhe12, Nle21,38, Lys23, Cml27,41, Glu30, Aib32, Lys33]Ac-h/rCRF(9-41); (cyclo 30-33) [DPhe12, Cml27, Glu30, DLeu32, Lys33]Bz-h/rCRF(9-41); (cyclo 30-33)[DPhe12, Nle21,38, Aib22, Cml27, Glu30, Lys33]Ac-h/rCRF(9-41); (cyclo 30-33)[DPhe12, Nle21,38, Aib24, Cml27, Glu30, Lys33]Ac-h/rCRF(9-41); (cyclo 30-33)[DPhe12, Nle21,38, Cml27, Aib28, Glu30, Lys33] Ac-h/rCRF(9-41); (cyclo 30-33)[DPhe12, Nle21,38, Cml27, Aib29, Glu30, Lys33]Ac-h/rCRF(9-41); (cyclo 30-33) [DPhe12, Nle21,38, Cml27, Glu30, Aib31, Lys33]Ac-h/ rCRF(9-41); (cyclo 30-33)[DPhe12, Nle21,38, Cml27, Glu30, Lys33, Aib34]Ac-h/rCRF(9-41); (cyclo 30-33) [DPhe12, Nle21,38, Cml27, Glu30, Lys33, Aib39]Ac-h/ rCRF(9-41); (cyclo 30-33)[DPhe12, Nle21,38, Cml27, Glu30, Lys33, Aib40]Ac-h/rCRF(9-41); (cyclo 30-33) [DPhe12, Nle21,38, Cml27, Glu30, Lys33, Aib41]Ac-h/ rCRF(9-41); (cyclo 30-33)[DPhe12, Nle21,38, Cml27,40, Glu30, Lys33, Aib41]Ac-h/rCRF(9-41); (cyclo 30-33) [DPhe12, Nle21,38, Aib24, Cml27,40, Glu30, Lys33]Ac-h/ rCRF(9-41); (cyclo 30-33)[DPhe12, Nle21,38, Aib22,24, Cml27, Glu30, Lys33]Ac-h/rCRF(9-41); (cyclo 30-33) [DPhe12, Nle21,38, Cml27, Glu30, Aib31,41, Lys33]Ac-h/ rCRF(9-41); (cyclo 30-33)[DPhe12, Cml14,27, Nle21,38, Glu30, Aib31, Lys33]Ac-h/rCRF(9-41); (cyclo 30-33) [DPhe12, Nle21,38, Cml27,40, Aib32,41, Glu30, Lys33]Ac-h/rCRF(9-41); (cyclo 30-33)[DPhe12, Cml14,27, Nle21,38, Aib24,41, Glu30, Lys33]Ac-h/rCRF(9-41); (cyclo 30-33)) [DPhe12, Nle21,38, Cml27,36,40, Glu30, Lys33]Ac-h/ rCRF(9-41); (cyclo 30-33)[DPhe12, Nle21,38, Cml27,40, Glu30, DHis32, Lys33]Ac-h/rCRF(9-41); (cyclo 30-33) [DPhe12, Nle21,38, Cml27,36,37, Glu30, Lys33]Ac-h/ rCRF(9-41); (cyclo 30-33)[DPhe12, Nle21,38, Cml27,37, 41, Glu30, Lys33]Ac-h/rCRF(9-41); (cyclo 30-33)[DPhe12, Nle21,38, Cml27,37,41, Glu30, DHis32, Lys33]Ac-h/rCRF (9-41); (cyclo 30-33)[DPhe12, Nle21,38, Cml27,36,40, Glu30, DHis32, Lys33]Ac-h/rCRF(9-41); and/or (cyclo 30-33)[DPhe12, Cml14,27,40, Nle21,38, Glu30, Lys33]Ac-h/rCRF(9-41).

As demonstrated herein, full-length astressin B promotes hair growth (e.g., reverses and/or prevents hair loss) in living mammals. Moreover, structure-activity studies have shown that fragments of astressin B are functionally active (Yamada et al., *J. Med. Chem.*, 47(5):1075-1078, 2004; Rijkers et al., *ChemBioChem*, 5:340-348, 2004). Thus, also described herein are methods of promoting hair growth (e.g., slowing, stopping, reversing or preventing hair loss, or stimulating hair growth in the absence of hair loss) by administering astressin B ((cyclo 30-33)[DPhe12, Nle21,38, Cml27,40, Glu30, Lys33]Ac-h/rCRF(9-41)- or a functional fragment thereof. In one embodiment, a functional fragment of astressin B lacks up to 2, up to 5, up to 8, up to 10, up to 12, up to 15, up to 16, or up to 21 N-terminal amino acids. In other embodiments, a functional fragment of astressin B includes at least the 12 C-terminal amino acids of the parent peptide. A functional fragment of astressin B retains at least one functional activity of the parent peptide, including, e.g., hair-growth promoting activity, CRF-R1 and/or CRF-R2 binding activity, inhibition of CRF-stimulated ACTH release, and/or inhibition of CRF-stimulated cAMP production.

B. Exemplary Syntheses of Cyclic CRF Antagonist Peptides

Cyclic CRF antagonist peptides useful in the disclosed methods may be synthesized by any method known in the chemical arts. Exemplary techniques for peptide and peptidometric synthesis are described by, for instance, Bodanszky and Bodanszky, *The Practice of Peptide Synthesis*, New York:Springer Verlag, 1994; Jones, *Amino Acid and Peptide Synthesis*, 2nd Ed., Oxford University Press, 2002, and "Solid Phase Peptide Synthesis," In: *Methods in Enzymology*, Vol. 289, ed. by Fields, New York:Academic Press, 1997. Moreover, custom peptide synthesis is widely available in the commercial market. Companies providing such service include GenScript Corporation (Piscatawa, N.J.), Invitrogen (Carlsbad, Calif.), AnaSpec (San Jose, Calif.), Dalton Chemical Laboratories (Toronto, Ontario Canada), Orbigen (San Diego, Calif.), and many others.

In one example, classical peptide solution synthesis can be used to synthesize cyclic CRF antagonist peptides, for example to generate large quantities of peptides. If more limited quantities of cyclic CRF antagonist peptides (e.g., less than about 3 kg) are desirable for a particular method embodiment, solid phase synthesis can be used (see, e.g., Merrifield, *J. Am. Chem. Soc.*, 85:2149, 1964).

In some methods of cyclic CRF antagonist peptide synthesis, reactive side chain groups of the various amino acid moieties will be blocked with suitable protecting groups which will prevent a chemical reaction from occurring at such side chain until the protecting group is removed. If desirable, an alpha-amino group on an amino acid or a peptide can also be blocked, for example, during reactions involving a carboxyl group of an amino acid or peptide. An alpha-amino protecting group can be selectively removed to allow subsequent reaction to take place at that location. Accordingly, during synthesis of a peptide, an intermediate compound can be produced which includes each of the amino acid residues located in its desired sequence in the peptide chain with various of these residues having side-chain protecting groups.

Alpha-amino protecting groups are known in the art in the stepwise synthesis of polypeptides. Exemplary alpha-amino protecting groups, include, for example, (i) acyl-type protecting groups, such as formyl (For), acrylyl (Acr), benzoyl (Bz) and/or acetyl (Ac), which can be used at the N-terminal residue (e.g., to protect against aminopeptidases) and, unlike traditional protecting groups, may not be removed from the synthesized polypeptide; (ii) aromatic urethan-type protecting groups, such as benzyloxycarbonyl (Z) and substituted Z, such as p-chlorobenzyloxycarbonyl, p-nitrobenzyloxycarbonyl, p-bromobenzyloxycarbonyl, and/or p-methoxybenzyloxycarbonyl; (iii) aliphatic urethan protecting groups, such as t-butyloxycarbonyl (BOC), diisopropylmethoxycarbonyl, isopropyloxycarbonyl, ethoxycarbonyl, and/or allyloxycarbonyl; (iv) cycloalkyl urethan-type protecting groups, such as fluorenyl methyloxycarbonyl (Fmoc), cyclopentyloxy-carbonyl, adamantyloxycarbonyl, and/or cyclohexyloxy-carbonyl; and/or (v) thiourethan-type protecting groups, such as phenylthiocarbonyl. In some methods for synthesizing cyclic CRF antagonist peptides, two exemplary alpha-amino protecting groups are BOC and Fmoc.

Thr and Ser side chains include a hydroxyl group, which is optionally protected during the synthesis of cyclic CRF antagonist peptides. Groups useful for protecting the hydroxyl group of Thr or Ser include acetyl (Ac), benzoyl (Bz), tert-butyl, triphenylmethyl (trityl), tetrahydropyranyl, benzyl ether (Bzl) and/or 2,6-dichlorobenzyl (DCB). In some methods of cyclic CRF antagonist peptide synthesis, an exemplary protecting group for Thr and/or Ser hydroxyl groups is Bzl.

Optional protecting groups for the guanidino group of Arg or liar can include nitro, p-toluenesulfonyl (Tos), Z, adamantyloxycarbonyl and/or BOC.

An optional protecting group for the amido group of Asn or Gln is a xanthyl (Xan) group. In other syntheses, Asn or Gln can be coupled without side chain protection in the presence of hydroxybenzotriazole (HOBt).

An ester-forming protecting group can be used to protect the β- or γ-carboxyl group of Asp or Glu. Exemplary ester-forming protecting groups include cyclohexyl (OChx), benzyl (OBzl), 2,6-dichlorobenzyl, methyl, ethyl, and/or t-butyl (Ot-Bu) esters. When a BOC strategy is used, the Boc group at the N-terminus is cleaved in 60-100% trifluoroactic acid (TFA) while side chain protection is achieved with protecting groups that are resistant to TFA deblocking. Final cleavage and deprotection of the peptido resin is then achieved with a stronger acid, for instance, hydrofluoric acid (HF). For the protection of the side chains of Boc-glutamic and Boc-aspartic acids, OChx is a preferred ester-protecting group.

The side chains of Lys or Orn optionally can be protected with amino-protecting groups, such as Z, 2-chlorobenzyloxycarbonyl (2Cl-Z), Tos, t-amyloxycarbonyl (Aoc), BOC and/or aromatic or aliphatic urethan-type protecting groups described above. When a BOC strategy is used for Lys, 2Cl-Z is an exemplary amino-protecting group.

The imidazole nitrogen of His residues optionally may be protected with a group such as Tos or 2,4-dinitrophenyl (DNP). The hydroxyl group of Tyr residues optionally may be protected with DCB. The sulfur of a Met residue may be protected, if desired, with oxygen.

The selection of a side chain amino protecting group is not critical except that it should be one which is not removed during deprotection of the alpha-amino groups during the synthesis. Hence, the alpha-amino protecting group and the side chain amino protecting group ideally are not the same.

The C-terminus of a peptide optionally can be modified with —$NH_2$ (or other amino group, —$N(R_1)R_2$, where is $R_1$ and $R_2$ are independently, hydrogen or lower alkyl (such as methyl, ethyl, propyl, i-propyl, butyl, i-butyl, tert-butyl, or other substituent described elsewhere for amidated peptides), a protecting group, such as an ester, or an anchoring bond used in solid phase synthesis for linking to a solid resin support, such as NH-benzhydrylamine (BHA) resin support or NH-pararmethylbenzhydrylamine (MBHA) resin support.

Cleavage from a BHA or MBHA resin directly provides an amide analog of a CRF antagonist. By employing a methyl derivative of such a resin, a methyl-substituted amide can be created.

An amide cyclizing linkage (lactam bridge) may be carried out while a partially protected peptide remains attached to a resin as disclosed in U.S. Pat. Nos. 5,064,939 and 5,043,322. Such a procedure effectively creates an amide cyclizing bond between the two desired side chains while other residues, such as Asp, Glu, Orn and/or Lys, in the peptide intermediate retain their side chain protection.

When cyclizing via an amide bond between a side chain carboxyl group of the 30-position residue and a side chain amino group of the 33-position residue or vice versa, it is advantageous to synthesize the protected peptide on an MBHA or BHA resin and to derivatize the benzyl ester of the particular carboxyl acid side chain to the hydrazide while the peptide is still attached to the resin and then react it with a selectively deprotected amino side chain as set forth in U.S. Pat. No. 5,043,322. Cyclization can be accomplished by using a base-labile protecting group, e.g., OFm, for the carboxyl side chain of the residue to be involved in the amide-bond bridge and using Fmoc as a protecting group for the amino side chain on the other residue that is to be involved. The alpha-amino protecting group on the residue at the N-terminus of the intermediate and all of the other side chain protecting groups remain in place while the two base-labile groups are removed using piperidine or the like. Following such selective removal, a reaction to accomplish cyclization is carried out by treating with BOP which effects substantially complete generation of an amide bond.

Introduction of a carbamoyl group at the N-terminus of a cyclic CRF antagonist peptide can be achieved, in one example, via reaction of the deprotected N-terminus with tertio-butyl isocyanate. In other examples, carbamoylated peptides and alkylurea-containing peptides can be prepared by reaction of a resin-bound partially deprotected amino peptide with an isocyanate (such as, tosyl isocyanate, benzyl isocyanate, trimethylsilyl isocyanate, and t-butyl isocyanate). The reaction can occur either during elongation or after completion of the peptide chain. Protecting groups of the resulting ureas can be removed during final anhydrous HF cleavage except for trimethylsilyl, which is acid labile and is advantageously removed under TFA deprotection conditions (e.g., 1% m-cresol in 50% TFA/DCM) during SPPS. The presence of a base such as DIEA is not preferred when using tosyl or trimethylsilyl isocyanates because it may result in overreaction of the isocyanate and biuret as byproduct. Amino peptido-resins may also be reacted with benzyl isocyanate; provided that, removal of benzyl groups from benzylureas may involve extended treatment of anhydrous HF (e.g., 6 hours at room temperature). Protected peptido-resins can be cleaved and deprotected in anhydrous HF in the presence of a scavenger.

Other representative methods for synthesis of cyclic CRF antagonist peptides are described in U.S. Pat. No. 6,323,312 (see, e.g., Examples I-XVI) and U.S. Pat. No. 5,874,227, and in Example 10 (below). Synthesized peptides can be purified, for example, by reverse-phase HPLC or any other method commonly known in the art.

C. Representative Methods for Determining CRF Antagonist Activity

The CRF antagonist activity of cyclic peptides useful in a disclosed method optionally can be determined using any of a number of standard assays, including functional assays or competitive binding assays. CRF receptors mediate a number of cellular functions, the inhibition of which functions can identify a compound as a CRF antagonist. In one standard assay, CRF antagonist activity is determined by the inhibition of CRF-stimulated ACTH release from primary rat pituitary cultures (Vale et al., *Endocrinol.*, 91:562-572, 1972). Briefly, rat pituitaries are harvested, pituitary cells dissociated (e.g., in collagenase buffer containing DNase II) and isolated, and grown in culture for several days. On the assay day, the cells are placed in serum-free medium containing 0.1% (w/v) ovalbumin and 1 μg/ml aprotinin. hCRF (e.g., 0.3 nM) in the presence or absence of a cyclic CRF peptide antagonist are added to the culture medium for several hours (e.g., about 3 hours). After the incubation period, the culture medium is removed and assayed for ACTH concentration, e.g., using commercially available radioimmunoassay kits (e.g., DiaSorin, Inc., Stillwater, Minn.). A cyclic CRF antagonist peptide will substantially reduce or inhibit CRF-induced ACTH release from the pituitary cells.

In another functional assay, cyclic CRF peptide antagonist inhibition of CRF-stimulate cyclic adenosine monophosphate production can be determined (see, e.g., Guo et al., *J. Med. Chem.*, 48(16):5104-7, 2005).

A variety of CRF receptor binding assays, for example utilizing CRF-R1 or CRF-R2 alone or in combination with other CRF receptors, can also be used to characterize cyclic CRF peptide antagonist. A cyclic CRF peptide antagonist may be a competitive (reversibly or irreversibly blocking the action of native or non-native CRF receptor agonists such as CRF) or non-competitive antagonist. Binding assays for competitive and non-competitive receptor antagonists are very well known in the art; for example, Li et al. (*J. Pharmacol. Exp. Ther.*, 305(1):86-96, 2003) describe CRF-R2 antagonist competition binding assays using membranes prepared from HEK293e cells expressing human recombinant CRF-R1, and rat cortex and pituitary membranes containing native CRF-R1. Another representative binding assay utilizing CRF receptor is described in Chen et al., *Proc. Natl. Acad. Sci. USA*, 90:8967-8971, 1993.

The activity of a cyclic CRF peptide antagonist also can be determined in vivo using adrenalectomized (adx) rats as described in Hernandez et al., *J. Med. Chem.*, 36:2860-2867, 1993. Briefly, rats are adrenalectomized under anesthesia and permitted to recover for several days (e.g., at least about one week) with a diet supplemented with oranges and water containing 0.9% NaCl. Rats are administered (e.g., by intravenous injection) a putative cyclic CRF peptide antagonist. Blood samples are collected before and after treatment (e.g., immediately after treatment and/or at various times after treatment (such as, 15-30 minutes, up to 2 hours, up to 4 hours, up to 12 hours, and/or up to 24 hours or more after treatment)). Plasma from frozen samples is assayed for ACTH concentration (e.g., using commercially available kits, such as, Allegro Kit, Nicoles Institute, San Juan Capistrano, Calif.). Adx rats normally have elevated ACTH levels and a cyclic CRF peptide antagonist will lower such levels. Cyclic CRF antagonist peptides having a long duration of action can be expected to depress ACTH levels in Adx rats for an extended period following peptide administration (see, e.g., Rivier et al., *J. Med. Chem.*, 42:3175-3182, 1999).

IV. Methods of Use

As this disclosure demonstrates, cyclic CRF antagonist peptides stimulate hair regrowth in subjects having alopecia and prevent hair loss in subjects at risk for developing alopecia. This discovery reveals new uses for cyclic CRF antagonist peptides. Accordingly, described herein are methods of promoting hair growth in a subject by administering to the subject a therapeutically effective amount of one or more cyclic CRF antagonist peptides. Also described are methods of promoting hair growth in a tissue containing hair follicles by contacting such tissue with a therapeutically effective amount of one or more cyclic CRF antagonist peptides. Additional non-limiting methods involve combination therapies, such as, use of one or more cyclic CRF antagonist peptides together with one or more hair-growth promoting drugs (e.g., minoxidil) and/or hair-replacement (e.g., hair implantation) treatment. Cyclic CRF antagonists useful in the disclosed methods have been described in detail above.

Any organism capable of growing hair on any portion of its surface, e.g., a mammal, is contemplated as a subject in the disclosed methods. Thus, in particular examples, a subject in a disclosed method is a human or veterinary subject. Veterinary subjects include, e.g., any non-human mammals (such as, rodents (including mice or rats), dogs, cats, sheep, cows, goats (e.g., angora goats and others), horses, mink, llama, alpaca, fox, rabbit, chinchillas, beaver, sable, non-human primates (including lemurs, monkeys, orangutans, gorillas, bonobos, or chimpanzees), any animal from which fur (e.g., wool or pelt) is harvested, or any animal for which it is desirable to reduce hair loss (e.g., felines (for instance, to reduce production of hairballs) or other domestic animals (for instance, to reduce shed hair present in residence)), or combinations thereof (see, Nelson et al., *Vet. Rec.*, 12:121(24):576, 1987; Jefferies et al., *Vet. Rec.*, 121(24):576, 1987; Reuter et al., *Aust. Vet. J.*, 64(11): 351-2, 1987; Ray et al., *Vet. Res. Commun.*, 21(8):541-6, 1997; Sawyer et al., *J. Am. Vet. Med. Assoc.*, 214(1):71-4, 1999; Schmeitzel, *Vet. Clin. North Am. Small Anim. Pract.*, 20(6):1579-601, 1990; Baker, *In. Pract.*, 8(2):71-8, 1986; McElwee et al., *Dermatol.*, 211(1):47-53, 2005; Porter, *J. Anat.*, 202:125-131, 2003). In some exemplary methods, a subject is treated with a cyclic CRF antagonist peptide to increase the density and/or quality of hair (or fur) on all or a portion of its body. In particular examples, an animal from which fur is harvested (or which is harvested for its pelt) may be treated (e.g., from about 1 to about 8 weeks prior to harvest, from about 1 month to about 3 months prior to harvest, from about 3 months to about 6 months prior to harvest, from about 6 months to about 12 months prior to harvest, or for the lifetime (or the adult lifetime) of the animal) with a cyclic CRF peptide antagonist to improve the quality of the fur or pelt.

A subject may or may not (i) show observable signs of hair loss (such as, hair thinning or balding) and/or (ii) have a predisposition (e.g., genetic) or expectation (e.g., undertaking a therapeutic treatment known to cause hair loss) for developing hair loss. In some examples, a subject may exhibit (or reasonably expect) hair loss as a result of a health disorder, a therapeutic treatment, a nutritional deficiency (e.g., zinc, biotin and/or iron deficiency(ies)) or excess (e.g., excessive dietary zinc, selenium, calcium, and/or fat), and/or exposure to environmental hazards (such as, certain chemicals). Exemplary therapeutic treatments that can cause hair loss include radiation therapy and chemotherapy for the treatment of a variety of diseases, including neoplasia, Very high dose radiation treatments may permanently damage hair follicles; thus, in some embodiments, a disclosed method is practiced before, during and/or after radiation therapy of less than about 6,000 cGy. Many therapeutic agents are known to cause hair loss. Exemplary therapeutics having this effect, include cyclophosphamide, daunorubicin, doxorubicin, etoposide, ifosamide, paclitaxel, docetaxel, trimethadione, tacrolimus, lithium, atenolol, metoprolol, nadolol, propranolol, timolol, warfarin, heparin, allopurinol, amphetamines, levodopa, bromocriptine and pergolide, pramipexole, ropinerole, vitamin A, isotretinoin, etretinate, tricyclic antidepressants, amphetamines, bupropion, selegeline, clofibrate, gemfibrozil, cimetidine, ranitidine, famotidine, auranofin, indomethacin, naproxen, sulindac, methotrexate, lisinopril, carbimazole, iodine, thiocyanate, steroids, thiouracil, or combinations thereof. A cyclic CRF antagonist peptide may be administered before, during and/or after radiation therapy or a therapeutic treatment (and as discussed in more detail below).

Hair loss is the symptom of and/or accompanies a variety of health disorders (including some nutritional imbalances). Accordingly, the disclosed methods can be useful in subjects having, exhibiting symptoms of, and/or predisposed to such health disorders, including alopecia areata (universalis, totalis, patchy, or androgenica), traction alopecia, folliculitis alopecia, telogen effluvium, loose-anagen syndrome, toxic alopecia, acquired immune deficiency (AID), hypothroidism, hyperthyroidism, lupus erythematosus, diabetes, iron deficiency, syphilis, Cushing syndrome, dermatitis, zinc deficiency, anxiety disorders, trichotillomania, hypercortisolemia, urticaria, inflammation of the skin, or inflammatory skin disorders (such as, psoriasis, eczema, acne and/or seborrhea), or combinations thereof.

The activation of corticotropin releasing factor (CRF) signaling pathway has emerged as an important component to coordinate the acute endocrine, behavioral, immune and visceral responses to stress (Bale and Vale, *Ann. Rev. Pharmacol. Toxicol.*, 44:525-557, 2004; Tache et al., *Brit. J. Pharmacol.*, 141:1321-13301, 2004; Turnbull and Rivier, *Proc. Soc. Exp. Biol. Med.*, 215:1-10, 1997; Bale, *Hormone Behavior*, 48:1-10, 2005, De Souza, *Psychoneuroendocrinol.*, 20:789-819, 1995). Both animal and human studies have shown that stress is a primary and/or exacerbating factor of hair loss as well as itchiness of the skin and inflammation of the skin (Peters et al., *Exp. Dermatol.*, 15:1-13, 2006; York et al., *Psychol. Rep.*, 82:1044-1046, 1998; Garcia-Hernandez et al., *J. Dermatol.* 26:625-632, 1999). Acute emotional stress has also been suggested to precipitate alopecia areata by activation of overexpressed CRF-2b receptors in the hair follicles (Katsarou-Katsari et al., *Dermatol.*, 203:157-161, 2001). Accordingly, some disclosed method embodiments are directed to treatment and/or prevention of hair loss accompanying stress disorder (e.g., acute stress disorder and/or posttraumatic stress disorder).

The disclosed methods may be used to promote hair growth on any body surface of a subject where hair growth is desired, including, for example, the scalp, chest, face (e.g., beard, eyebrows, etc.), and/or genital area. In veterinary subjects, hair growth over the entire body surface (excluding eyes, mouth, nose and other typically hair-less regions) may be desired. Particular methods involve growing hair on all or part of the scalp (such as, an area of premature balding or hair thinning) or in an area of alopecia-affected skin of a subject.

This disclosure further contemplates the use of cyclic CRF antagonist peptides for promoting in vitro hair growth, for instance, in isolated hair follicles (Waldon et al., *In Vitro Cell Dev. Biol. Anim.*, 29A(7):555 61, 1993) or hair-follicle-containing tissues (such as, transected hair follicles (Raposio et al., *Plast. Reconstr. Surg.*, 102(1):221-6, 1998) or hair grafts (Bernstein, *Dermatol. Surg.*, 24(12):1342-1346, 1998)). In some embodiments, cyclic CRF antagonist peptides can be used to promote hair growth in a pre-transplantation and/or post-transplantation graft.

"Promoting hair growth" for the purposes of the disclosed methods is intended to have its broadest possible meaning. Thus, in some examples, promoting hair growth is to decrease a rate of hair loss in an area that normally has hair such that (i) on-going hair loss occurs at a slower rate (e.g., retarded or slowed hair loss); (ii) hair loss is substantially stopped (e.g., the rate of hair loss is substantially the same as the rate of hair growth); or (iii) hair loss is reversed (e.g., the rate of hair loss is lower than the rate of hair growth) such that the area of interest exhibits a net increase in the amount of hair. In another example, promoting hair growth is to induce hair growth on a substantially hairless surface capable of growing hair, such as a body surface that formerly had, but has lost substantially all, hair. In still another example, promoting hair growth includes inducing or stimulating hair growth on a hair-containing surface that is not experiencing hair loss; for example, increasing the rate at which hair-growing cells grows hair and/or increasing the number of hair-growing cells (e.g., increasing the number of hair follicles or the number of follicles in the anagen phase). Such latter method embodiments may be useful to increase hair density or length. Promotion of hair growth also includes decreased shedding (either at the roots or by breaking/fragility) measured, for example, by hair pull tests. The promotion of hair growth can be measured using any method known in the art or any of the methods disclosed herein, for example, quantitative and qualitative comparison of treated areas or subjects to controls.

Administration of Cyclic CRF Antagonist Peptides

This disclosure contemplates administering to a subject one or more cyclic CRF antagonist peptides, for example, to promote hair growth (e.g., to slow, stop, or reverse hair loss). Any cyclic CRF antagonist peptide delivery system or treatment regimen that has the desired effect (such as, effective treatment of hair loss) can be used. Similarly, cyclic CRF antagonist peptide-containing compositions can be formulated in any manner known in the art. Exemplary cyclic CRF antagonist peptide formulations may include diluent(s), excipient(s) or carrier(s), or one or more additional ingredients, such as UV-blocking agents, antioxidants, emollients, or fragrances. The specific dose level and frequency of dosage for any particular subject may be varied and will depend upon a variety of factors, including the activity of the specific peptide, the metabolic stability and length of action of that peptide, the age, body weight, general health, gender, diet, mode and time of administration, rate of excretion, drug combination, and nature and/or severity of the condition of the subject receiving therapy. An attending healthcare worker (or the subject) may elect to modify the concentration, amount, and/or dosage in order to adjust the dose to the particular response of each subject. Exemplary modes of administration, formulations and dosage regimens applicable to the disclosed methods and compositions are discussed in more detail below.

1. Selected Methods of Administration and Formulations

Modes of administration of a cyclic CRF antagonist peptide (also referred to as a "therapeutic agent") useful in the disclosed methods include, parenteral and/or enteral routes, such as intrathecal, intramuscular, intraperitoneal (ip), intravenous (iv), subcutaneous, intranasal (e.g., U.S. Pat. No. 6,440,392), epidural, transdermal (e.g., topical), intrarectal, intravaginal, buccal absorption, and/or oral (U.S. Pat. Nos. 5,912,014 and 6,086,918) routes. For purposes of this disclosure "subcutaneous" administration includes any route (such as injection) of delivering a therapeutic under any layer of the skin (e.g., dermis or epidermis); thus, "subcutaneous" includes subdermal, intradermal, and/or intracutaneous delivery. Particular examples involve subcutaneous, intraperitoneal, and/or intravenous modes of administration (such as injection). More particular examples involve administration of cyclic CRF antagonist peptides by subcutaneous injection. Still other examples involve transdermal (or topical) administration of cyclic CRF antagonist peptides (e.g., using iontophoresis or microneedles). Injection methods, such as intraperitoneal or intravenous injection, may be facilitated by a catheter, for example attached to a reservoir, which has been inserted into the appropriate biological space.

In some examples, a therapeutic agent (such as one or more cyclic CRF antagonists) is administered systemically to a subject. For example, cyclic CRF antagonists can be systemically administered via injection (e.g. intraperitoneal or intravenous injection) or orally. In a specific example, one or more cyclic CRF antagonists are administered orally. Methods of oral administration of peptides are known. For example, cyclic CRF antagonists can be administered orally using Emisphere's Eligen® technology or using adjuvant permeation enhancers (such as sodium caprate).

In a specific embodiment, a therapeutic agent is administered locally to an area in need of treatment or where treatment is desirable (e.g., the scalp). This may be achieved, for example, by local or regional injection or infusion, transdermal delivery (e.g., iontophoresis), topical application, and/or implantation (such as, with implants formed from porous, non-porous, or gelatinous materials, including membranes, such as sialastic membranes or fibers and the like). In one embodiment, local or regional administration can be by one or more injections (such as, subcutaneous injections) at a site or in a region where treatment is desired, such as all or part of the scalp. In particular examples, multiple subcutaneous injections (such as up to about 10, up to about 15, up to about 20, up to about 25, or even as many as 50 or 100 sc injections) are given at substantially the same time (e.g., sequentially or concomitantly) in different regions of an area to be treated, such as all or part of the scalp.

Transdermal delivery of therapeutic peptides is also known. Some formulations for transdermal peptide delivery contain mixed micelles, modified liposomes, nanoparticles, albumin conjugates, and/or polysaccharides (such as, hyaluronan). In particular examples, various delivery systems that may be used to facilitate administration of peptide therapeutics include liposomes (Tian et al., *Proc. Int. Symp. Control. Release Bioact. Mat.*, 25:439-440, 1998; Hoffman, *J. Drug Target,* 5(2):67-74, 1998; Langer, *Science,* 249: 1527, 1990; Treat et al., In: *Liposomes in the Therapy of infectious Disease and Cancer*, ed. by Lopez et al., N.Y.: Liss, pp. 353-365, 1989), biodegradable microspheres (Hora et al., *Biotechnol.,* 8:755-758, 1990; Wang and Wang, *J. Biomater. Sci. Polym. Ed.,* 14(2): 157-83, 2003 (describing microspheres including poly(lactide/glycolide) polymers); Johnston et al. *Pharm. Res.,* 9:425-434, 1992), hydrogels, for example superporous hydrogels (Hennink et al., *J. Control. Release,* 48:107-114, 1997 and Omidian et al., *J. Pharm. Pharmacol.* 58:317-37, 2007), poloxamer gels (Morishita et al., *Int. J. Pharm.,* 212:289-293, 2001; Stratton et al., *J. Pharm. Sci.,* 86:1006-1010, 1997; Wenzel et al., *J. Control. Release,* 85:51-59, 2002; Wang et al., *J. Parenter. Sci. Technol.,* 47:183-189, 1993), biodegradable matrices (e.g., poly(lactide/glycolide) polymers; Liu et al., *Biomaterials,* 25:3201-3210, 2004), hydrophilic creams (Harada and Okajima, *Growth Horm. IGF Res.* 17:171-6, 2007), thiomers (for example for delivery via a mucosal surface) (see for example Leitner et al., *J. Pharm. Sci.* 93: 1682-91, 2004 describing a polycarbophil-cysteine (PCP-Cys)/glutathione (GSH) gel formulation), and iodine (for example pre-treatment of the skin with iodine (such as 1% iodine, for example povidone-iodine 10% ointment) followed by dermal application of the desired peptide, see Sintov and Wormser, *J. Control. Release* 118:185-8, 2007). In some examples, the delivery system includes a combination of systems, such as liposomes and hydrogels (see for example Mourtas et al., *Colloids and Surfaces* 55:212-21, 2007).

In particular examples, peptides (such as cyclic CRF antagonists) are delivered to a subject using encapsulants. For example, encapsulants containing one or more cyclic CRF antagonists will release their peptide contents when broken open (for example with friction, pressure, moisture, pH 4-6, or bacteria present on the skin). Methods of making encapsulants are known in the art. In a particular example, an encapsulation particle is 20 to 40 nm in diameter, wherein the outer layer is a monolayer phospholipid membrane, which surrounds an inner lipid core containing one or more cyclic CRF antagonists. In some examples, encapsulants are made up of equal parts of gelatin and gum arabic; algin; carrageenan; chiosan; Tegosphere® methacrylate copolymer (Degussa, Germany): polymethyl methacrylate; phosphatidyl choline; poly (lactic-co-glycolic acid); anionic polylactide-co-glycolide; albumin and dextran sulfate (such as the Promaxx® microspheres from Baxter Healthcare); and copolymers of ethylene oxide and butylene oxide.

Various physical and/or mechanical technologies also are available to permit the transdermal administration of macromolecules (such as, peptides). Such technologies include iontophoresis (see for example Kalia et al., *Adv. Drug Del. Rev.* 56:619-58, 2004) sonophoresis, needle-less injection, and/or microstructured arrays (sometimes called microneedles; one particular example is the Microstructured Transdermal System (MTS) commercially available from 3M) (see, e.g., Alain et al., *J. Control. Release,* 81:113-119, 2002; Santi et al., *Pharm. Res.,* 14(1):63-66, 1997; Sebastien et al., *J. Pharm. Sci.,* 87(8):922-925, 1998). Methods of making and using arrays of solid microneedles that can be inserted into the skin for transdermal delivery of peptides (such as cyclic CRF antagonists) are provided in Martanto et al. (*Pharm. Res.* 21:947-52, 2004 and *Am. Inst. Chem. Eng.* 51:1599-607, 2005). In some examples, the delivery system includes a combination of systems, such as microneedles made of biocompatible and biodegradable polymers (Park et al., *J. Control. Release* 104:51-66, 2005). Laser systems have also been developed to ablate the stratum corneum from the epidermal layer (Lee et al., *J. Pharm. Sci.,* 91(7): 1613-1626, 2002). The laser-ablated regions offer lower resistance to drug (peptide) diffusion than non-ablated skin.

In other examples, administration of a therapeutic may be achieved by adhesive-backed tablets that are placed in the mouth between the gum and either the cheek or lip. Such tablets have been used to successfully deliver a 30-amino acid peptide (glucagon-like peptide 1 (GLP-1) in a formulation developed by TheraTech™).

In yet another embodiment, a therapeutic peptide can be delivered in a controlled release system. In one embodiment, a pump may be used (see, e.g., Langer, *Science,* 249:1527, 1990; Sefton, *Crit. Rev. Biomed. Eng.,* 14:201, 1987; Buchwald et al., *Surgery,* 88:507, 1980; Saudek et al., *N. Engl. J. Med.,* 321:574, 1989). In another embodiment, polymeric materials can be used (see, e.g., Ranger et al., *Macromol. Sci. Rev. Macromol. Chem.,* 23:61, 1983; Levy et al., *Science,* 228:190, 1985; During et al., *Ann. Neurol.,* 25:351, 1989; Howard et al., *J. Neurosurg.,* 71:105, 1989). Other controlled release systems, such as those discussed in the review by Langer (*Science,* 249:1527, 1990), can also be used.

The vehicle in which a therapeutic agent is delivered can include pharmaceutically acceptable compositions known to those of ordinary skill in the art. For instance, in some embodiments, therapeutic agents useful in the disclosed methods are contained in a pharmaceutically acceptable carrier. The term "pharmaceutically acceptable" means approved by a regulatory agency of the federal or a state government or listed in the U.S. Pharmacopoeia or other generally recognized pharmacopoeia for use in animals, and, more particularly in humans. The term "carrier" refers to a diluent, adjuvants excipient, or vehicle with which the therapeutic is administered. Such pharmaceutical carriers can be sterile liquids, such as water and oils, including those of petroleum, animal, vegetable, or synthetic origin, such as peanut oil, soybean oil, mineral oil, sesame oil, and the like. Saline solution is an exemplary carrier when the pharmaceutical composition is administered via injection (such as intravenously, intraperitoneally or subcutaneously). Water, blood plasma medium, aqueous dextrose, and glycerol solutions can also be employed as liquid carriers, particularly for injectable solutions. The medium may also contain conventional pharmaceutical adjunct materials such as, for example, pharmaceutically acceptable salts to adjust the osmotic pressure, lipid carriers such as cyclodextrins, proteins such as serum albumin, hydrophilic agents such as methyl cellulose, detergents, buffers, preservatives and the like.

Examples of pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The therapeutic, if desired, can also contain minor amounts of wetting or emulsifying agents, or pH buffering agents. The therapeutic can take the form of solutions, suspensions, emulsion, tablets, pills, capsules, powders, sustained release formulations, and the like. The therapeutic can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, and the like. A more complete explanation of parenteral pharmaceutical carriers can be found in Remington, *The Science and Practice of Pharmacy,* 19th Edition, Chapter 95, 1995.

Therapeutics useful in some disclosed methods may take a variety of forms and may be supplied either separately or mixed together in unit dosage form, for example, in solid, semi-solid and liquid dosage forms such as tablets, pills, powders, liquid solutions, or suspensions, or as a dry lyophilized powder or water free concentrate in a hermetically sealed container such as an ampoule or sachette indicating the quantity of active agent. Where the composition is to be administered by infusion it can be dispensed with an infusion bottle containing sterile pharmaceutical grade water or saline. Where the composition is administered by injection, an ampoule of sterile water or saline can be provided so that the ingredients may be mixed prior to administration.

2. Topical Formulations

Particular method embodiments envision application of a therapeutic agent containing one or more cyclic CRF antagonist peptides to the skin of a subject. When a cyclic CRF antagonist peptide is administered in a cutaneous or topical carrier or diluent, the carrier or diluent may be chosen from any known in the cosmetic or medical arts; for example, any gel cream, lotion, ointment, liquid or non liquid carrier, emulsifier, solvent, liquid diluent or other similar vehicle which does not exert deleterious effect on the skin or other living animal tissue. The carrier or diluent is usually a mixture of several ingredients, including, but not limited to liquid alcohols, liquid glycols, liquid polyalkylene glycols, water, liquid amides, liquid esters, liquid lanolin, lanolin derivatives and similar materials. Alcohols include mono and polyhydric alcohols, including ethanol, glycerol, sorbitol, isopropanol, diethylene glycol, propylene glycol, ethylene glycol, hexylene glycol, mannitol and methoxyethanol. Typical carriers may also include ethers (such as, diethyl and dipropyl ether), methoxypolyoxyethylenes, carbowaxes, polyethyleneglycerols, polyoxyethylenes and sorbitols. In some embodiments, the topical carrier includes both water and alcohol in order to maximize the hydrophylic and lipophylic solubility (for instance, a mixture of ethanol or isopropanol with water). One skilled in the art may choose other carriers or diluents to adapt to specific dermatologic needs.

A topical carrier may also include various other ingredients commonly used in ointments and lotions and well known in the cosmetic or medical arts; for example, agents capable of blocking ultraviolet radiation (e.g., sunscreens), antioxidants, fragrances, perfumes, gelling agents, thickening agents (such as carboxymethylcellulose), surfactants, stabilizers, emollients, coloring agents and other similar agents.

In some examples a topical composition contains one or more agents capable of blocking UV radiation (such as, UVA or UVB radiation, or both). Such agents include, without limitation, para-aminobenzoate (PABA) and its derivatives, ethylhexyl methoxycinnamate) DEA methoxycinnamate, padimate O ethylhexyl salicylate homosalate, TEA salicylate, oxybenzone, dioxybenzone, sulisobenzone, avobenzone, octocrylene, titanium dioxide, zinc oxide or menthyl anthranilate. In other embodiments, a topical composition contains at least one UVA-blocking agent, such as oxybenzone, dioxybenzone, sulisobenzone, avobenzone or zinc oxide. In still other embodiments, a topical composition includes at least one UVB-blocking agent, such as substituted para-aminobenzoates (e.g., octyl dimethyl PABA), alkyl esters of para-methoxycinnamate (e.g., octyl para-methoxycinnamate), certain esters of salicylic acid (e.g., homomethyl salicylate or octyl salicylate), ethylhexyl methoxycinnamate, DEA methoxycinnamate, padimate O, ethylhexyl salicylate, homosalate, TEA salicylate, octocrylene or titanium dioxide.

In particular embodiments, a topical composition contains one or more antioxidants such as, Vitamins A and E, or their esters, magnesium ascorbyl phosphate, DL panthenol, beta glucan, propyl, octyl or dodecyl esters of gallic acid, butylated hydroxyanisole (usually as a mixture of ortho and meta isomers), butylated hydroxytoluene or nordihydroguaiaretic acid.

In other embodiments, a topical composition includes one or more emollients. Non-limiting representative emollients include mineral oil, lanolin oil, coconut oil, cocoa butter, olive oil, almond oil, macadamia nut oil, aloe extract, jojoba oil, safflower oil, corn oil, liquid lanolin, cottonseed oil, peanut oil, purcellin oil, perhydrosqualene, castor oil, polybutene, odorless mineral spirits, sweet almond oil, calophyllum oil, ricin oil, vitamin E acetate, mineral spirits, the oil of cereal germs (such as the oil of wheat germ), and esters such as isopropyl palmitate, isopropyl myristate, butyl myristate, hexadecyl stearate, decyl oleate, acetyl glycerides, the octanoates and benzoates of (C12-C15) alcohols, the octanoates and decanoates of alcohols and polyalcohols such as those of glycol and glycerol, ricin oleates of alcohols and poly alcohols, such as those of isopropyl adipate, hexyl laurate and octyl dodecanoate.

In some examples, a cyclic CRF antagonist peptide is administered in a shampoo, hair mousse, skin cream or lotion, or other hair-care or skin-care product. In other examples, a cyclic CRF antagonist peptide is administered in a spray-on formulation or aerosol formulation.

3. Therapeutically Effective Amounts and Dosage Regimens

Therapeutic preparations will contain a therapeutically effective amount of at least one active ingredient (such as, a cyclic CRF antagonist peptide) together with a suitable amount of carrier so as to provide proper administration to the patient. The formulation should suit the mode of administration.

The amount of the therapeutic that will be effective depends on the mode of administration, the nature of the disorder or condition to be treated, as well as the stage of the disorder or condition. Effective amounts can be determined by standard clinical techniques. The precise dose to be employed in the formulation will also depend on the route of administration, and should be decided according to the judgment of the health care practitioner and each subject's circumstances. In some examples, a therapeutically effective amount for topical or transdermal delivery is at least 100-fold greater than a dose for injection such as at least 200-fold greater, at least 500-fold greater, at least 800-fold greater, at least 1000-fold greater, or at least 2000-fold greater.

For example, the amount of active ingredient (e.g., a cyclic CRF antagonist peptide) delivered in a local or regional injection regime (such as, subcutaneous, subdermal, intracutaneous, intradermal and/or intramuscular injection) is typically from about 0.1 µg to about 100 mg per injection site (such as from about 0.1 µg to about 10 mg, from about 0.1 µg to about 1000 µg, from about 0.2 µg to about 500 µg per injection site, from about 0.3 µg to about 250 µg per injection site, from about 0.4 µg to about 100 µg per injection site, from about 0.5 µg to about 50 µg per injection site, or from about 0.75 µg to about 25 µg per injection site, or from about 1.0 µg to about 10 µg per injection site). In some methods, the amount of active ingredient (e.g., a cyclic CRF antagonist peptide) delivered in a local or regional injection regime may be up to about 100 mg or more, for instance, to achieve longer durations of action. Similar amounts of active ingredient (e.g., a cyclic CRF antagonist peptide) will have use in some methods involving mechanical and/or physical transdermal application methods (such as iontophoresis, sonophoresis, needleless injection, and/or microneedles). In other embodiments, a dosage range for non-topical administration (such as, oral administration, or intravenous or intraperitoneal injection) of a composition containing a cyclic CRF antagonist peptide is from about 1 to about 1000 µg/kg body weight in single or divided doses; for example from about 1 to about 500 µg/kg, from about 1 to about 300 µg/kg, from about 1 to about 100 µg/kg, from about 2 to about 50 µg/kg from about 3 to about 25 µg/kg, or from about 5 to about 10 µg/kg. In still other embodiments, a formulation containing a cyclic CRF antagonist peptide is administered in such a manner and/or amount as to achieve a target tissue cyclic CRF antagonist peptide concentration from about 100 to about 200 µg/kg per day for topical or systemic administration. In specific embodiments, a formulation containing one or more cyclic CRF antagonist peptides is administered at cyclic CRF antagonist peptide concentration of at least 0.05 mg, such as at least 0.5 mg at least 5 mg, at least 50 mg, or at least 500 mg for topical or transdermal administration.

The therapeutic agents useful in the disclosed methods can be administered at about the same dose throughout a treatment period, in an escalating dose regimen, or in a loading-dose regime (for example, in which the loading dose is about two to five times the maintenance dose). In some embodiments, the dose is varied during the course of a treatment based on the condition of the subject being treated, the severity of the disease or condition, the apparent response to the therapy, and/or other factors as judged by one of ordinary skill in the art. In some embodiments long-term treatment with a therapeutic peptide in a disclosed method is contemplated, for instance, to prevent reoccurrence of hair loss. In particular method embodiments, a formulation containing a cyclic CRF antagonist peptide is administered once (or twice) per day for up to five consecutive days (such as, for three, four or five consecutive days). In humans, scalp hair has a cycle time of several years and vellus hair (very soft, short hair usually less than 2 cm long that grows in most places on the human body in both sexes) takes months to grow (Porter, *J. Anat.*, 202:125-131, 2003). Thus, in some methods, for example, involving human subjects, a formulation containing a cyclic CRF antagonist peptide is administered once or twice daily, weekly, or bimonthly for at least about 1 month (for example, at least about 3 months, at least about 6 months, at least about 9 months, at least about 12 months, or at least about 24 months). In some methods, administration of a formulation containing a cyclic CRF antagonist peptide is continued indefinitely.

4. Combination Therapy

The present disclosure also contemplates combinations of cyclic CRF antagonist peptides with one or more other agents or therapies useful in the treatment of hair loss (or the promotion of hair growth). For example one or more cyclic CRF antagonist peptides may be administered in combination with effective doses of other medicinal and pharmaceutical agents, or in combination other therapies such as hair transplantation. The term "administration in combination with" refers to both concurrent and sequential administration of the active agents. Examples of agents useful in combination with a cyclic CRF antagonist peptide for the promoting hair growth (such as preventing hair loss), include, e.g., minoxidil, finasteride, oral contraceptives (e.g., ethinyl estradiol-ethynodiol diacetate, desogesterl-ethynyl estradiol, and ethinyl estradiol-norgesterimate), spironlactone, dexamethasone, anthralin, psoralen and ultraviolet A, steroids, topical immunotherapy, immunosuppressives, and anti-microbial treatment.

EXAMPLES

The following examples are provided to illustrate certain particular features and/or embodiments. These examples should not be construed to limit the invention to the particular features or embodiments described.

Example 1

Astressin B Promotes Hair Growth and Pigmentation when Administered by Subcutaneous Injection This Example demonstrates that astressin B promotes hair growth when administered to a subject by subcutaneous injection in an alopecic region.

Adult (6-9 month old) male and female C57BL/6 mice that overexpress a rat CRF transgene (Stenzel-Poore et al., *Endocrinol.*, 130:3378-3386, 1992) were used in this Example. CRF transgenic (CRF-OE) mice exhibit endocrine abnormalities involving the hypothalamic-pituitary-adrenal axis, such as elevated plasma levels of ACTH and glucocorticoids. Moreover, these animals display physical changes, such as excess abdominal fat accumulation, muscle atrophy, thin skin, and alopecia on the back and ventral abdomen area. Alopecia in these animals develops after about 7-8 weeks of age and is fully developed at about 4 months of age. This phenotype, i.e., hair loss in adulthood, is similar to that observed in some forms of human alopecia (e.g., the age-dependent balding of adult, human males (and females)).

The CRF-OE model further is believed to be applicable across species because, for example, recent evidence indicates that major components of the CRF system are expressed in the mouse and human skin (Slominski et al., *Ann. NY Acad. Sci.* 885:287-311, 1999). In particular Ucn 1 and Ucn 2 gene are highly expressed in human or mouse dorsal skin as detected by immunohistochemistry at the level of epidermis, blood vessel walls and adnexal structures including hair follicle and sebaceous glands (Chen et al., *Endocrinol.*, 145:2445-2457, 2004; Slominski et al., *J. Clin. Endocrinol. Metab.*, 85:815-823, 2000; Singh et al., *Brain Behav. Immun.*, 13:225-2397, 1999). Clinical reports indicate that acute emotional stress activates CRF2 receptors in scalp skin biopsies in patients (Katsarou-Katsari et al., *Dermatol.*, 203:157-61, 2001). $CRF_1$ receptors and alternative splice variants have been described in mouse skin to vary in function of the follicle cycle (Pisarchik and Slominski, *FASEB J.*, 15:2754-2756, 2001).

CRF-OE mice were housed in standard plastic cages in a controlled environment (temperature=21-23° C.; humidity=30-35%; 12-hour light cycle with lights on 06:00 AM) and fed a standard rodent diet (PROLAB™ RMH 2500). Experiments were conducted in accordance with institutional guidelines.

Eight (8) male and 9 female CRF-OE mice were injected subcutaneously with 5 µg/mouse astressin B or astressin 2B, in 0.1 ml sterile water, once per day for 5 consecutive days. Similar doses of astressin B and astressin 2B previously were shown, respectively, to inhibit elevated ACTH release in adrenalectomized rats for over 12 hours (Rivier et al., *J. Med. Chem.*, 42:3175-3182, 1999) and delay gastric emptying for over 6 hours (Rivier et al., *J. Med. Chem.*, 45:4737-4747, 2002). Each injection was given in a single puncture located along or about the midline of the back. CRF-OE mice similarly injected with saline alone were used as negative controls. Astressin B and astressin 2B peptides were synthesized as previously described (Rivier et al., *J. Med. Chem.*, 45:4737-4747, 2002; Gulyas et al., *Proc. Natl. Acad. Sci. USA,* 92:10575-10579, 1995) and were diluted with sterile water immediately preceding each injection.

The effects of the treatments on hair growth and pigmentation in the CRF-OE mice were observed every other day in the first 2 weeks following the initial injection and twice a week for at least 2 months total time. It appeared that hair growth (if any) typically was completed by 4 weeks post-treatment. The general conditions of treated and control mice, such as weight, back skin thickness hair luster, skin wounds and indurations, were also noted.

Hair growth in CRF-OE mice was assessed using the hair growth scale developed by Vegesna et al. (*Endocrinology* 2002, 143:43) 89-4396, 2002) modified to account for phenotypic differences between CRF-OE mice. Scores were made visually as well as using photographs of each mouse at a weekly interval. The degree of alopecia varied between individual CRF-OE mice; thus, the percent difference between the amount of hair present in the test area (described below) before and 4 weeks after treatment was converted to a score of 0-10. A zero score corresponded to a no change in the amount of hair in the test area and a score of 10 corresponded to full hair growth in the entire test area. The scale for monitoring hair growth in CRF-OE mice is more particularly described in Table 2.

TABLE 2

Hair growth score on the back of mice

| Score | Description |
|---|---|
| 0 | No change in the amount of hair in the test region. |
| 1 | 10% of the test area covered by hair |
| 2 | 20% of the test area covered by hair |
| 3 | 30% of the test area covered by hair |
| 4 | 40% of the test area covered by hair |
| 5 | 50% of the test area covered by hair |
| 6 | 60% of the test area covered by hair |
| 7 | 70% of the test area covered by hair |
| 8 | 80% of the test area covered by hair |
| 9 | 90% of the test area covered by hair |
| 10 | 100% of the test area covered by hair (i.e., full hair growth in the entire test region) |

Hair-growth was observed in a region on the back of each CRF-OE mouse that fully developed alopecia (age≥4 months). The area was defined anteriorly by a line joining the front of the ears; posteriorly by a line joining the pelvic girdles; and laterally, between the lines projecting caudally from each ear root.

Pigmentation of the skin (also referred to as skin color) in the test region was also measured because, in C57BL/6 mice, the skin darkens at the onset of hair growth. A pigmentation score from 0-10 was given to each mouse with a score of 0 corresponding to bright pink skin color/pigment in the entire test region, a score of 1-5 corresponding to increasing intensity of a pale greyish color/pigment of skin in the test region, a score of 6-9 corresponding to increasing but non-confluent darker color/pigment of skin in the test region, and a score of 10 corresponding to black pigmentation of the entire test region. Pigmentation was measured one week after the fifth and final injection because changes (if any) in pigmentation are substantially complete by that time.

Figure 1B:
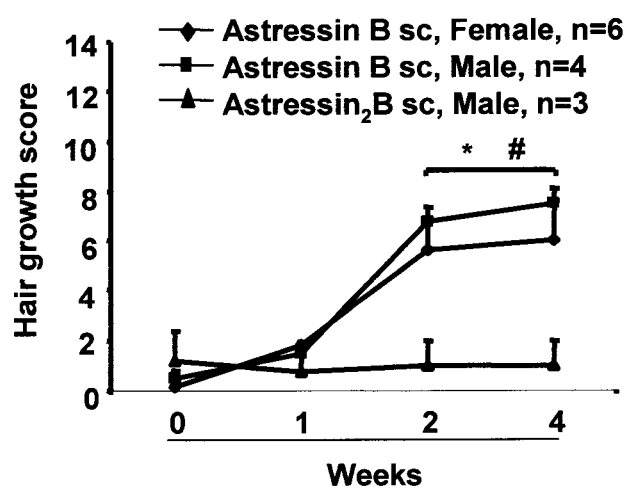

The pigmentation score at one week post-treatment and the 4-week hair growth scores of two sets of experiments in female and male CRF-OE mice are detailed in Table 3 and in FIGS. 1A and 1B. In addition, representative reproductions of CRF-OE mice before and after subcutaneous injection with astressin B or astressin 2B are illustrated in FIG. 1C.

TABLE 3

Skin pigmentation and hair growth in adult CRF-OE mice treated with sc astressin B or astressin 2B

| | | | Score | | | | |
|---|---|---|---|---|---|---|---|
| | | | Week 0 | | Week 1 | | Week 4 |
| Mouse ID | Sex | Treatment | Pg | BK | Pg | BK | BK |
| 327 | Female | Astressin B | 0 | 0 | 8 | 2 | 9 |
| 335 | Female | Astressin B | 0 | 0 | 7 | 2 | 8 |
| 347 | Female | Astressin B | 0 | 0 | 2 | 2 | 2 |
| 366 | Female | Astressin B | 0 | 1 | 8 | 1 | 8 |
| 378 | Female | Astressin B | 0 | 0 | 10 | 2 | 9 |
| 389 | Female | Astressin B | 0 | 0 | 0 | 2 | 0 |
| 325 | Male | Astressin B | 0 | 0 | 10 | 2 | 8 |
| 326 | Male | Astressin B | 0 | 0 | 10 | 2 | 9 |
| 333 | Male | Astressin B | 0 | 1 | 7 | 1 | 7 |
| 341 | Male | Astressin B | 0 | 1 | 4 | 1 | 6 |
| 345 | Male | Astressin 2B | 0 | 0 | 1 | 0 | 0 |
| 356 | Male | Astressin 2B | 0 | 5 | 2 | 0 | 0 |
| 371 | Male | Astressin 2B | 0 | 0 | 2 | 0 | 0 |

Pg = Skin pigmentation;
BK = Back Hair Growth Score

Eight (8) out of 9 (89%) female mice responded to injected (sc) astressin B with increased pigmentation and hair growth. Data for 6 female mice is shown in Table 3. The remaining 3 female mice were observed qualitatively. Similarly, 4 out of 4 (100%) of the male mice responded to astressin B with increased pigmentation and hair growth. In contrast, none of the astressin 2B-injected mice (0%) grew significant amounts of hair. Similarly, no hair growth was observed for 1 month post treatment in CRF-OE male and female mice (5-7 months old) that received subcutaneous astressin 2B (10 μg/mouse/day) for 7 days using an implanted mini-pump. Each of the pigment score and hair growth response score (at weeks 1, 2 and 4; see FIG. 1B) was significantly higher in astressin B-treated female and male mice as compared to the astressin 2B-treated mice.

As shown in FIG. 1B, subcutaneous injection of astressin B induced hair growth as early as one week after the last injection and such hair growth was maintained for at least 4 weeks post treatment (FIGS. 1B and 1C (left series of reproductions)). The hair growth coverage ranged between 20-90% with 1 female having 20% coverage, 2 males having 50-75% coverage, and 4 females and 2 males having 80-90% coverage. Two of the adult CRF-OE mice treated with astressin B were observed for an extended period; astressin B-dependent hair growth was substantially maintained (without subsequent treatment) for up to 4 months post treatment in these mice.

Experiments were repeated in female CRF-OE mice (4.5 months old) to confirm the results. Mice were injected with astressin B (5 μg/mouse, 10 mice) or saline (5 mice) for 5 days. Skin pigment and hair growth scores were given as described before. Five astressin B-treated and five saline injected mice were sacrificed for skin tissue collection at seven days post last injection. Additional mice (5) injected with astressin B were sacrificed on day 14. Five littermate wild type (WT) mice were used as normal control. Adrenal gland and abdominal fat weights were also checked at sacrifice of each mouse.

Scores of pigment and hair growth re-confirm the observation on the effect of astressin B to restore hair growth in alopecic CRF-OE mice (Table 4). There was no difference in weights of adrenal gland between CRF-OE and WT mice, while the weight of abdominal fat was significantly higher in CRF-OE than in WT mice when adjusted as per 20 g body weight. Astressin B injections in CRF-OE mice changed neither adrenal gland nor abdominal fat weight compared with saline at the times of observation (Table 5).

TABLE 4

Skin pigmentation and hair growth in adult female CRF-OE mice treated with sc astressin B or saline

| Follow up days post last injection | ID | Initial Wt. | Sex | Tx | Before (Week 0) Pg | BK | VAb | Week 1 Pg | BK | VAb | Week 2 Pg | BK | VAb |
|---|---|---|---|---|---|---|---|---|---|---|---|---|---|
| 7 days | 714 | 34.2 | F | AB | 0 | 0.5 | 0.25 | 8.5 | 8.5 | 0.25 | — | | |
|  | 716 | 35.6 | F | AB | 0 | 0.5 | 0.5 | 10 | 10 | 0.5 | — | | |
|  | 762 | 40 | F | AB | 0 | 1 | 0.5 | 9.5 | 9.5 | 0.5 | — | | |
|  | 774 | 35.6 | F | AB | 0 | 1 | 0.25 | 10 | 10 | 0.25 | — | | |
|  | 775 | 34.4 | F | AB | 0 | 0.5 | 0.25 | 9.5 | 9.5 | 0.25 | — | | |
|  | Ave. | 35.96 | | | 0 | 0.7 | 0.35 | 9.5 | 9.5 | 0.35 | | | |
| 14 days | 722 | 36.6 | F | AB | 0 | 0 | 0.25 | 10 | 10 | 0.25 | — | 5 | 0.5 |
|  | 724 | 38.1 | F | AB | 0 | 0.5 | 0.25 | 9.5 | 9.5 | 0.25 | — | 9.5 | 0.5 |
|  | 747 | 36 | F | AB | 0 | 0 | 0.5 | 7 | 7 | 0.75 | — | 8 | 0.5 |
|  | 754 | 34.9 | F | AB | 0 | 0 | 0.25 | 10 | 10 | 0.25 | — | 10 | 0.5 |
|  | 780 | 33.1 | F | AB | 0 | 0 | 0.5 | 9 | 9 | 0.25 | — | 8 | 0.5 |
|  | Ave. | 35.74 | | | 0 | 0.1 | 0.35 | 9.1 | 9.1 | 0.35 | | 8.1 | 0.5 |
| 7 days | 715 | 37.3 | F | Sal | 0 | 0 | 0.25 | 0 | 0 | 0.25 | — | | |
|  | 739 | 37.3 | F | Sal | 0 | 0 | 0.25 | 0 | 0 | 0.25 | — | | |
|  | 753 | 40.2 | F | Sal | 0 | 0.5 | 0.25 | 0 | 0 | 0.25 | — | | |
|  | 760 | 34.7 | F | Sal | 0 | 0 | 0.5 | 0 | 0 | 0.25 | — | | |
|  | 766 | 37.8 | F | Sal | 0 | 0 | 0.25 | 0 | 0 | 0.25 | — | | |
|  | Ave. | 37.46 | | | 0 | 0.1 | 0.3 | 0 | 0 | 0.25 | | | |

ID = Mouse No.;
Initial Wt. = Initial weight (gm);
Tx = Treatment;
Pg = Skin pigmentation;
BK = Back Hair Growth Score;
VAb = Ventral Abdomen Hair Growth Score;
AB = Astressin B;
Sal = Saline

TABLE 5

Adrenal gland and abdominal fat weight in adult female CRF-OE mice and wild type (WT) littermates treated with sc astressin B or saline

| Follow up days post last injection | ID | Wt. @ euth | Sex | Tx | Adjusted/20 g Wt Adren (mg) | AbdFat (g) |
|---|---|---|---|---|---|---|
|  | 714 | 35.6 | F | AB | 6.6 | 1.5 |
| CRF-OE | 716 | 35.5 | F | AB | 5.4 | 1.4 |
| 7 days | 762 | 40.3 | F | AB | 5.7 | 1.9 |
|  | 774 | 35.6 | F | AB | 6.6 | 1.4 |
|  | 775 | 35.6 | F | AB | 4.7 | 1.2 |
|  | Ave. | 36.52 | | | 5.8 | 1.5 |
|  | 722 | 37.6 | F | AB | 6.3 | 1.3 |
| CRF-OE | 724 | 38 | F | AB | 5.7 | 1.2 |
| 14 days | 747 | 36.1 | F | AB | 6.8 | 1.2 |
|  | 754 | 36.1 | F | AB | 7.4 | 1.3 |
|  | 780 | 33.3 | F | AB | 6.8 | 1.3 |
|  | Ave. | 36.22 | | | 6.6 | 1.2 |
|  | 715 | 37.2 | F | Sal | 5.8 | 1.3 |
| CRF-OE | 739 | 36.2 | F | Sal | 6.7 | 1.5 |
| 7 days | 753 | 40.2 | F | Sal | 6.1 | 1.2 |
|  | 760 | 33.4 | F | Sal | 7.2 | 1.5 |
|  | 766 | 36.8 | F | Sal | 6.4 | 1.2 |
|  | Ave. | 36.76 | | | 6.4 | 1.4 |
| WT | 706 | 24.9 | F | — | 5.7 | 0.4 |
|  | 712 | 24.7 | F | — | 5.7 | 0.8 |
|  | 708 | 23.3 | F | — | 5.3 | 0.8 |
|  | 709 | 25.9 | F | — | 8.3 | 0.6 |
|  | 735 | 31.7 | F | — | 6.4 | 1.0 |
|  | Ave. | 26.1 | | | 6.3 | 0.7 |

ID = Mouse No.;
Wt. @ euth = weight (gm) on the day of euthanasia;
Tx = Treatment;
Adren = adrenal glands weight;
AbdFat = abdominal fat weight;
AB = Astressin B;
Sal = Saline This Example demonstrates that astressin B induces significant, long-lasting hair growth in male and female subjects having an alopecia phenotype.

Example 2

Astressin B Promotes Hair Growth when Administered by Intraperitoneal Injection

Example 1 demonstrated that localized subcutaneous injection of astressin B promotes hair growth in alopecic mice. This Example illustrates that astressin B also promotes hair growth in such mice when administered by intraperitoneal injection.

CRF-OE mice (approximately 4 months old) with fully developed alopecia on their backs were injected intraperitoneally (ip) with equal volumes (0.1 ml) of either saline or astressin B (5 μg/mouse/day) for 5 consecutive days. Skin pigment score and hair growth (on the back) score were determined as described in Example 1. In addition, because adult CRF-OE mice also lose ventral abdomen hair, a ventral abdomen (Vab) hair growth score was determined. The area considered for scoring ventral abdomen hair growth was delineated, in the front (anteriorly), by a horizontal line across the tip of the xifoid process (distal sternum), in the rear (posteriorly), by a horizontal line joining the back of the thighs along the anus, and, laterally, by a straight line along the lateral side of the ventral abdomen on left and right sides.

Figure 2A:
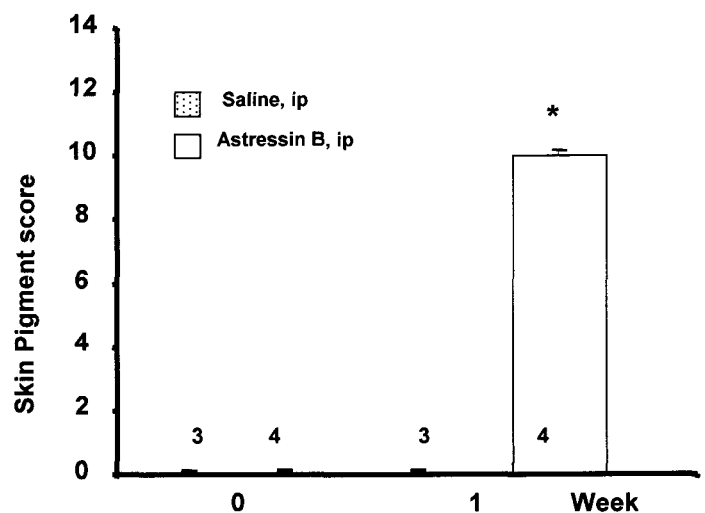
FIG. 2 includes several panels showing the effect of 5 consecutive daily intraperitoneal injections (5 µg/mouse/day) of astressin B or saline on hair growth and skin pigmentation in adult, CRF-OE mice over a period of approximately eight weeks. The bar graph in panel (A) shows the skin pigmentation score before the start of injection (week 0) and 1 week after the final injection. Panel (B) shows a time course of the hair growth score (on the back) from before injection (week 0) to 8 weeks after the final injection. Data points in panels A and B represent the mean±SEM for 4 CRF-OE mice. *$p<0.05$ versus week 0 (paired t-test) or all other corresponding saline time points (t-test). Panel (C) shows images of representative saline- or astressin B-treated mice, as indicated. Images of astressin B-treated mice were taken 3 days (middle row) or 4 weeks (bottom row) after the final injection. The same four mice are shown in the middle and bottom rows.

As shown in Table 6 and FIG. 2A, all astressin B-injected mice (4/4) had dark skin (score of 10) one week after the final injection, whereas none of the saline-injected mice (0/3) had dark skin at this time point. Four and seven weeks after the final injection, all astressin B-injected mice had fully grown hair (score of 9-10) whereas all saline-injected mice remained bald (score 0) or even got worse by developing patches of alopecia in regions (e.g., the buttocks) outside the hair-growth scoring areas (Table 6 and FIG. 2B).

in control male CRF-OE mice injected ip with saline, the skin color remained pink and no hair grew throughout the monitoring period.

Example 3

Astressin B Administration Promotes Histological Change in the Hair Follicles of Alopecic Skin This Example demonstrates that subcutaneous administration of astressin B affected histological change in the hair follicles of adult CRF-OE mice.

Wild-type (C57BL/6) mice, saline-treated CRF-OE mice, CRF-OE mice treated with astressin B or astressin 2B as described in Example 1 (sc injection), and adult CRF-OE mice treated with astressin 2B as described in Example 2 (ip injection), were euthanized, Male mice were used in each case. Whole dorsal skin pieces were harvested for histology four weeks after the final sc injection of the respective peptides or two weeks after ip astressin B or saline injection.

Skin samples were fixed in 4% paraformaldehyde. Paraffin-embedded sections were processed for staining of

TABLE 6

Skin pigmentation and hair growth in adult CRF-OE mice treated with ip astressin B or saline

| ID | WT | Sex | Tx | Before (Week 0) | | | Week 1 | | | Week 4 | | Week 8 | |
|---|---|---|---|---|---|---|---|---|---|---|---|---|---|
| | | | | Pg | BK | VAb | Pg | BK | VAb | BK | VAb | BK | VAb |
| 2498 | 32.2 | M | AB | 0.0 | 1 | 2.5 | 10 | 9 | 8 | 9.5 | 10 | 8.5 | 8 |
| 2501 | 26.9 | M | AB | 0.0 | 1 | 5 | 10 | 9 | 10 | 10 | 10 | 8 | 10 |
| 2491 | 28.4 | M | AB | 0.0 | 2 | 5 | 10 | 9.5 | 10 | 10 | 10 | 10 | 10 |
| 2492 | 28.7 | M | AB | 0.0 | 1 | 5 | 10 | 10 | 8 | 10 | 10 | 9.5 | 8 |
| Ave. | 29 | | | 0 | 1.25 | 4.4 | 10 | 9.4 | 9 | 9.9 | 10 | 9 | 9 |
| 12N | 27.0 | M | Sal | 0.0 | 1 | 2.5 | 0.0 | 0 | 2.5 | 0.0 | 2.5 | 0.0 | 2.5 |
| 12L | 29.1 | M | Sal | 0.0 | 0 | 2.5 | 0.0 | 0 | 2.5 | 0.0 | 2.5 | 0.0 | 2.5 |
| 17R | 30.0 | M | Sal | 0.0 | 3 | 5 | 0.0 | 0 | 2.5 | 0.0 | 2.5 | 0.0 | 2.5 |
| Ave. | 28.7 | | | 0.0 | 1.33 | 3.3 | 0.0 | 0 | 2.5 | 0.0 | 2.5 | 0.0 | 2.5 |

Figure 2B:
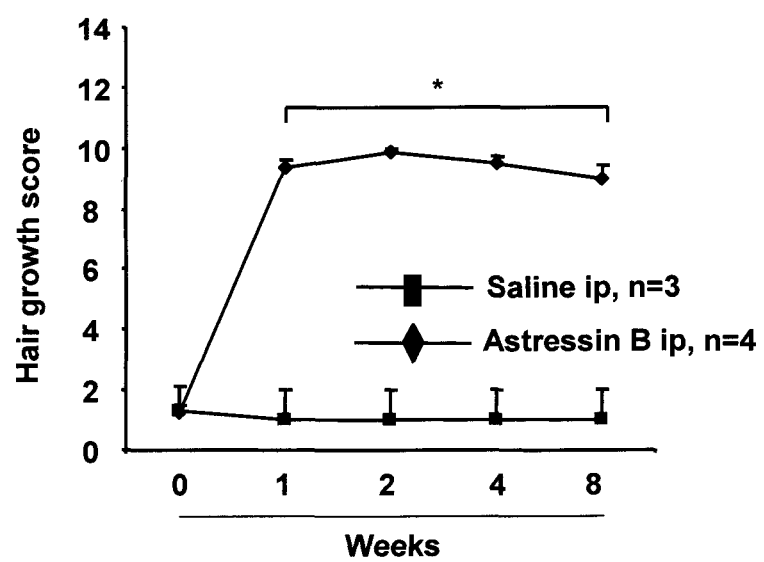
Figure 2C:
Figure 2C:
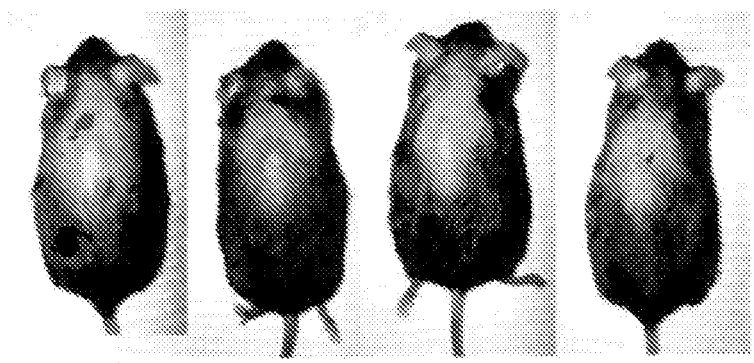
Figure 2C:

ID = Mouse No.;
WT = weight (gm);
Tx = Treatment;
Pg = Skin pigmentation;
BK = Back Hair Growth Score;
VAb = Ventral Abdomen Hair Growth Score;
AB = Astressin B;
Sal = Saline FIG. 2C (images in the middle row) shows that astressin B induced dark skin pigment as early as 3 days after the final injection with the darkest skin color observed at 7-10 days after the final injection (see FIG. 2A). Thereafter, the pigment waned and back hair grew over the entire alopecic area as illustrated in FIGS. 2B and 2C (bottom row). Hair grown in response to astressin B was maintained, at least, for 8 weeks (FIG. 2B) to 12 weeks after the final ip injection.

Therefore, short term treatment with the long acting (≥24 h) $CRF_1/CRF_2$ receptor antagonist, astressin-B injected intraperitoneally (ip) at 5 μg/mouse, once a day for 5 consecutive days in four-month old male CRF-OE mice, resulted in the development of dark pigment on the initially pink alopecic skin within 3 days after the last injection, and as the pigment increased to a maximal response within 7-10 days, hair sprouted out and grew to full length with 95-100% of hair coverage at 2 weeks (FIG. 2B). The re-grown hair was retained for the following 8 weeks and largely maintained up to 16 weeks after the last ip injection. By contrast, hematoxylin/eosin and examined by light microscopy. The thickness of the epidermis plus dermis and depth of hair follicles were measured and the number of hair follicles was counted per unit (a field obtained with 10× objective) in a total of 5 units per section.

Hair follicles in alopecic skin of saline-treated or astressin 2-B treated CRF-OE mice did not have the normal morphology found in wild-type mice (FIGS. 3A and 3D); for example, normal-sized hair follicles were rarely observed (FIGS. 3C and 3E) and hair follicles did not lean in the same direction. The depth of hair follicles in untreated CRF-OE mice was significantly shorter than that of wild type mice (0.37±0.03 mm versus 0.54±0.03 mm; p<0.05). In comparison, the average depth of hair follicles in astressin B-treated CRF-OE mice (FIG. 3B) was 0.42±0.05 mm, which is not significantly different from wild type mice. The hair follicles of astressin B-treated CRF-OE mice were also more developed and defined in structure (FIGS. 3B and 3F). For example, as shown in FIG. 3F, in hair re-grown areas of ip astressin B treated CRF-OE mice, hair follicle reformation was observed two weeks after the end of treatment (FIG.

3F). There were no significant differences in skin thickness or in hair follicle numbers between wild type mice (FIGS. 3A and 3D) and adult CRF-OE mice treated with astressin B (FIGS. 3B and 3F) or astressin 2B (FIG. 3C).

Example 4

Astressin B Prevents Hair Loss in Subjects Prone to Alopecia

This Example illustrates that astressin B not only promotes hair growth in already bald (or balding) subjects, but also prevents hair loss in subjects predisposed to alopecia.

Young CRF-OE mice do not exhibit the alopecia phenotype characteristic of adult CRF-OE mice. Alopecia in this strain fully develops in adulthood at approximately 12 weeks and older.

Young CRF-OE mice (5-6 weeks old) were treated with astressin B, astressin 2B, or vehicle (saline). Treatments were a single, daily subcutaneous injection (0.1 ml volume) of vehicle alone or 5 µg peptide per mouse for five consecutive days. Pigmentation and hair coverage scores were determined pretreatment and 1, 4, 8 and 16 weeks after the last treatment. Hair growth and pigmentation were determined as described in Examples 1 and 2.

Figure 4A:
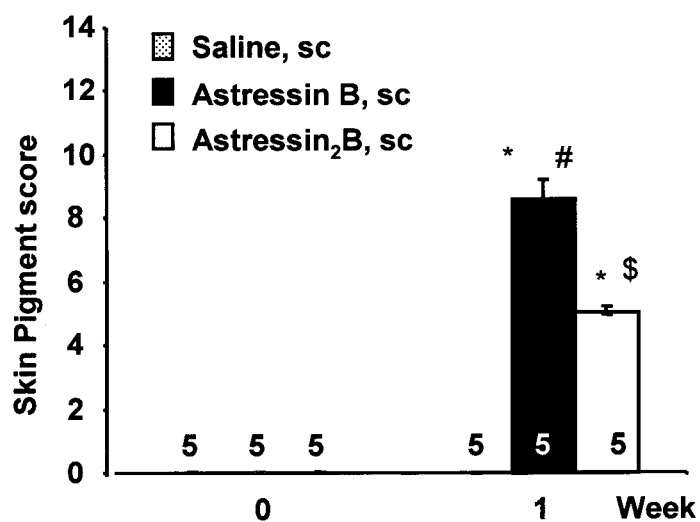
FIG. 4 includes several panels showing the effect of 5 consecutive daily subcutaneous injections (5 µg/mouse/day) of astressin B or astressin 2B on hair growth and skin pigmentation in young (not-yet-alopecic) CRF-OE mice over a period of approximately 16 weeks. Week 0 corresponds to results prior to injection of the respective peptides or vehicle (saline) alone. Weeks 1, 4, 8, and 16 correspond to results at the indicated number of weeks after the last injection. The bar graph in panel (A) shows the skin pigmentation score before the start of injection (week 0) and 1 week after the final injection for saline-, astressin B- and astressin 2B-treated mice. Panel (B) shows a time course of the hair growth score (on the back) from before injection (week 0) to 16 weeks after the final injection. Data points in panels A and B represent the mean±SEM for 5 mice. *$p<0.05$ vs week 0, paired t-test; \$ $p<0.05$ versus saline week 1; # $p<0.05$ versus astressin 2B or saline at the corresponding week, One Way ANOVA; β $p<0.05$ vs saline at the corresponding week, t-test. The left-most series of digital images in panel (C) shows a representative astressin B-treated female mouse at the indicated time periods. The right-most series of digital images show a representative astressin 2B-treated female mouse at the indicated time periods. The same mouse is shown at each time point in the respective series of images.
Figure 4B:
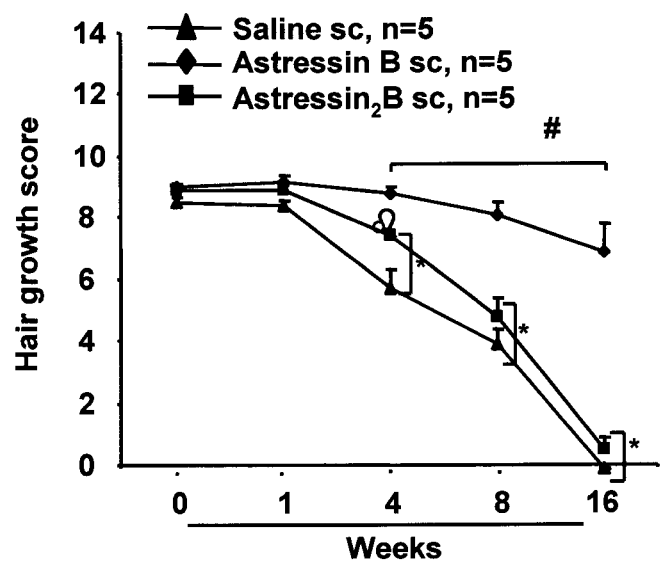

As shown in Table 7 and in FIGS. 4A-4C, all mice treated with astressin B (5/5) had dark pigmentation of the skin at 1 week after the last injection and had little or less (as compared to vehicle-treated subjects) hair loss (4/5) by 4, 8 and 16 weeks after the last injection. In contrast, all saline- and astressin 2B-injected mice lost hair and developed full alopecia as would be expected of CRF-OE mice (FIGS. 4B and 4C).

As expected, hair growth scores of the saline-, astressin 2B- and astressin B-treated groups were similar before and 1 week after treatment because the subject mice were almost fully furred at the onset of the trial. Between week 4 and week 16 post treatment, the saline and astressin 2B groups lost hair whereas astressin B-treated mice remained protected from developing full alopecia (FIGS. 4B and 4C). Some astressin 1-treated mice started to lose hair gradually 2 months after treatment (through a 4-month observation period) although to a lesser degree than the saline- or astressin 2B-treated groups (FIGS. 4B and 4C). Other astressin B-treated mice substantially retained their hair through the observation period.

Mice treated with saline did not develop skin pigmentation during the 16 week observation period while those treated with astressin 2B exhibited a moderate induction of skin pigments during the first week post injection (FIG. 4A). Astressin B also induced skin pigmentation within one week after the final injection.

This Example demonstrates that astressin B can prevent or substantially delay the onset of alopecia in subjects having a tendency to develop this disorder. It is expected that subsequent treatment with astressin B could prevent the gradual hair loss that developed over time in some astressin B-treated subjects. Due to the long-lasting effects of astressin B treatment on prevention of hair loss, repeated treatments could be relatively widely spaced in time; thus, presenting little or no inconvenience to the subject being treated.

TABLE 7

Skin pigmentation and hair growth in young (not-yet-hairless) CRF-OE mice treated with sc astressin B, astressin 2B, or saline

| ID | Wt | Sex | Tx | Before (Week 0) Pg | BK | Week 1 Pg | BK | Week 4 BK | VAb | Week 8 BK | VAb | Week 16 BK | VAb |
|---|---|---|---|---|---|---|---|---|---|---|---|---|---|
| 3N | 13.1 | F | AB | 0 | 8 | 9 | 9 | 10 | 10 | 10 | 10 | 8.5 | 10 |
| 4N | 14.6 | F | AB | 0 | 8 | 9 | 9 | 9 | 10 | 8.5 | 7.5 | 5 | 7.5 |
| 6L | 15.2 | F | AB | 0 | 9 | 6 | 9 | 8 | 10 | 7 | 7.5 | 2 | 7.5 |
| 7L | 15.3 | F | AB | 0 | 9 | 9 | 9 | 9 | 10 | 9 | 10 | 6 | 10 |
| 22R | 16.7 | M | AB | 0 | 9 | 10 | 10 | 9 | 10 | 9 | 10 | 6 | 10 |
| | | | | 0 | 8.6 | 8.6 | 9.2 | 9 | 10 | 8.7 | 9 | 5.5 | 9 |
| 8N | 14.3 | F | A2B | 0 | 9 | 6 | 9 | 8 | 5 | 6 | 2.5 | 0 | 2.5 |
| 9N | 13.8 | F | A2B | 0 | 9 | 5 | 9 | 7.5 | 5 | 6.5 | 5 | 0 | 2.5 |
| 16N | 14.1 | F | A2B | 0 | 9 | 5 | 9 | 8 | 5 | 6.5 | 2.5 | 0 | 2.5 |
| 18N | 16.2 | F | A2B | 0 | 9 | 5 | 9 | 7 | 7.5 | 7 | 5 | 2.5 | 2.5 |
| 21N | 15.4 | F | A2B | 0 | 9 | 5 | 9 | 7 | 5 | 6 | 2.5 | 1 | 2.5 |
| | | | | 0 | 9 | 5.2 | 9 | 7.5 | 5 | 6.4 | 3.5 | 0.7 | 2.5 |
| 23N | 15.4 | F | Sal | 0 | 9 | 0 | 9 | 8 | 5 | 6.5 | 5 | 0 | 2.5 |
| 23L | 13.4 | F | Sal | 0 | 9 | 0 | 9 | 6.5 | 5 | 6.5 | 5 | 0 | 2.5 |
| 24L | 15.9 | F | Sal | 0 | 9 | 0 | 9 | 6 | 7.5 | 4 | 2.5 | 0 | 2.5 |
| 24R | 13.6 | F | Sal | 0 | 8 | 0 | 8 | 5 | 5 | 3 | 5 | 0 | 2.5 |
| 24N | 15 | F | Sal | 0 | 8 | 0 | 8 | 6 | 5 | 5 | 5 | 0 | 2.5 |
| | | | | 0 | 8.6 | 0 | 8.6 | 6.3 | 5 | 5 | 4.5 | 0 | 2.5 |

ID = Mouse No.;
Wt = weight (gm);
Tx = Treatment;
Pg = Skin pigmentation;
BK = Back Hair Score;
VAb = Ventral Abdomen Hair Score;
AB = Astressin B;
A2B = Astressin 2B;
Sal = Saline

Example 5

Astressin B has Long-Term Effects on Hair Growth

This Example shows that a relatively short course of treatment with astressin B has long-lasting effects on hair growth.

Two female CRF-OE mice, which had fully developed alopecia, received a single daily subcutaneous injection of 5 µg astressin B (in 0.1 ml saline) in the back for five consecutive days. Four (4) months after the final injection, the growth of hair on the backs of both mice was scored 9 out of 10. Similarly, two out of four male CRF-OE mice received intraperitoneal injection of 5 µg astressin B for five consecutive days. Thus, the mice not only grew hair in a previously bald (or balding) region, but such hair was maintained for months without on-going treatment.

Similarly, a long-term protective effect of five daily subcutaneous injections of 5 µg astressin B (in 0.1 ml saline) was demonstrated in Example 4, wherein young CRF-OE mice maintained robust amounts of hair 4 months (16 weeks) after a fifth and final astressin B injection (see Table 7). Typically, untreated CRF-OE mice would fully develop alopecia by 4 months of age. In contrast, astressin 2B- and saline-injected mice exhibited considerable hair loss in the same 4 month time period.

Example 6

Astressin B is Superior to Non-Peptide CRF-R1 Antagonist (NBI 27914) and Minoxidil for the Promotion of Hair Growth Four groups of five adult (approximately 5 month old), female CRF-OE mice were injected subcutaneously with (i) 1% minoxidil sulfate (SIGMA, St. Louis) in 0.1 ml 1:2:7 (v/v) ethanol, polyethylene glycol and saline, respectively, pH 5.0, once per day for 10 consecutive days; (ii) 0.5 mg selective CRF-R1 non-peptide antagonist, NBI 27914 (TOCRIS™), in 0.1 ml 1:0.5:8.5 of ethanol, Tween-80, saline, respectively, pH 5.0 twice per day (each 12 hours) for 5 consecutive days, (iii) NBI 27914 vehicle (1:0.5:8.5 of ethanol, Tween-80, saline, respectively, pH 5.0) twice per day (each 12 hours) for 5 consecutive days; or (iv) minoxidil vehicle (1:2:7 (v/v) ethanol, polyethylene glycol and saline, pH 5.0) once per day for 10 consecutive days). Each subcutaneous injection (0.1 ml volume) was given in a single puncture located along or about the midline of the back. The regimen of minoxidil administration has previously been shown to facilitate hair regrowth (Shirai et al., *J. Dermatol. Sci.*, 25:213-218, 2001). The NBI 27914 administration regimen was as previously described by Martinez et al. (*J. Pharmacol. Exp. Ther.*, 301:611-617, 2002).

Figure 5A:
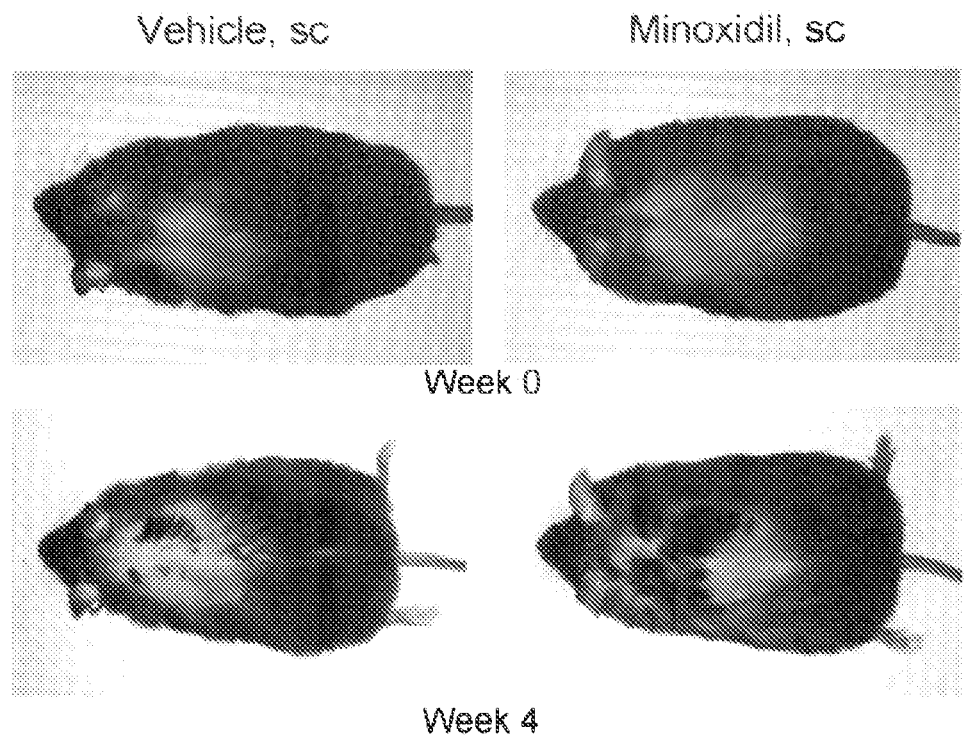
FIG. 5 shows the effects of subcutaneously injected minoxidil sulfate on alopecia in adult CRF-OE mice. Panel A shows images of representative mice before and 4 weeks after treatment with minoxidil or vehicle. Panel B is a time course of hair growth in minoxidil-(filled squares) or vehicle-(x) treated mice. Each point represents the mean±SEM, n=5.
Figure 5B:
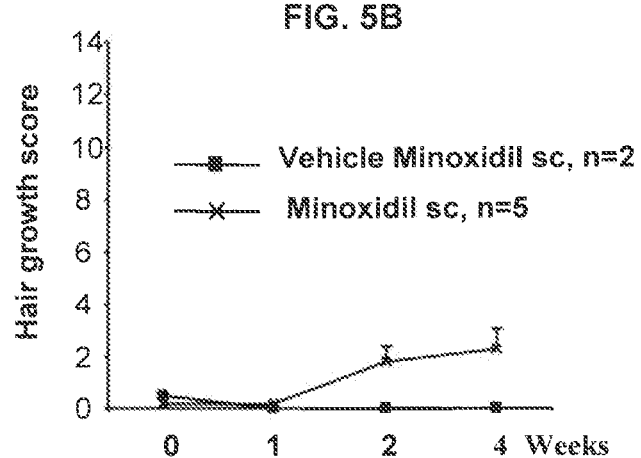

By two weeks after the final injection, minoxidil had induced patches of pigmentation in 3 of the 4 still-living, treated mice (one treated mouse died a few days after the first injection). Moderate hair growth in the pigmented patches was observed at 2 and 4 weeks after the last injection (FIGS. 5A and 5B). In contrast, mice receiving injections of minoxidil vehicle did not exhibit pigmentation or hair growth (FIGS. 5A and 5B).

Mice that received subcutaneous NBI 27914 injections developed poor health conditions and 4 out of 5 subjects did not survive more than four weeks following the final injection. Four weeks after the final injection, the surviving mouse exhibited small areas of patchy hair growth.

In comparison to previous examples (e.g., Examples 1 and 2), this Example demonstrates that the cyclic CRF antagonist peptide, astressin B, is a far-superior agent for inducing hair growth in subjects having alopecia than are non-peptide agents, minoxidil, or NBI 27914.

Example 7

Astressin B is Superior to Non-Peptide CRF-R1 Antagonist (NBI 27914) and Minoxidil for the Prevention of Hair Loss A representative number of young (not yet alopecic, e.g., 6-7 week old) male and/or female CRF-OE mice (e.g. 6 or 8 mice) are injected subcutaneously or intraperitoneally with (i) 5 µg of astressin B or an astressin B fragment in 0.1 ml sterile saline once per day for 5 consecutive days, (ii) 1% minoxidil sulfate (SIGMA, St Louis) in 0.1 ml 1:2:7 (v/v) ethanol, polyethylene glycol and saline, respectively, pH 5.0, once per day for 5 consecutive days, or (iii) 0.5 mg selective CRF-R1 non-peptide antagonist, NBI 27914 (TOCRIS™), in 0.1 ml 1:0.5:8.5 of ethanol, Tween-80, saline, respectively, twice per day (each 12 hours) for 5 consecutive days. Each subcutaneous injection is given in a single puncture located along or about the midline of the back. Age-matched CRF-OE mice similarly injected with 0.1 ml vehicle alone are used as negative controls. Astressin B fragments are as described in Example 8. Alternatively, topical astressin B can be applied to the mouse's back, for example 0.05 mg, 0.5 mg, 5 mg, 50 mg, or 500 mg of an astressin B fragment once daily for at least five consecutive days The effects of each treatment on prevention of hair loss and pigmentation are observed every other day in the first 2 weeks following the initial injection and twice a week for at least 2 months total time. Hair growth (or hair loss) is assessed using the hair growth scale described in Example 1. The general conditions of treated and control mice, such as weight, back skin thickness, hair luster, skin wounds and indurations, are noted.

Mice treated with the non-peptide antagonist, NBI 27914, or minoxidil exhibit substantially more loss of hair than do astressin B-treated mice over a two-month period. The general conditions of astressin B-treated mice are well and substantially the same throughout the treatment and observation periods. At least some of the mice treated with the non-peptide antagonist, NBI 27914, are expected to die or fail to thrive.

Example 8

Astressin B Fragments Promote Hair Growth

A representative number of adult male and/or female CRF-OE mice (e.g., 6 or 8 mice) with fully developed alopecia are injected subcutaneously or intraperitoneally with 5 µg of an astressin B fragment in 0.1 ml sterile saline once per day for 5 consecutive days. Each subcutaneous injection is given in a single puncture located along or about the midline of the back, CRF-OE mice similarly injected with 0.1 ml saline alone (or 5 µg astressin 2B in 0.1 ml saline) are used as negative controls. Alternatively, topical astressin B can be applied to the mouse's back, for example 0.05 mg, 0.5 mg, 5 mg, 50 mg, or 500 mg of an astressin B fragment once daily for at least five consecutive days. Similar methods can be used to demonstrate the ability of any cyclic CRF antagonist to promote hair growth (in any mammalian subject of interest).

Astressin B fragments include: (cyclo 30-33)[DPhe12, Nle21,38, Cml27,40, Glu30, Lys33]Ac-h/rCRF(10-41); (cyclo 30-33)[DPhe12, Nle21,38, Cml27,40, Glu30, Lys33]Ac-h/rCRF(11-41); (cyclo 30-33)[DPhe12, Nle21,38, Cml27, 40, Glu30, Lys33]Ac-h/rCRF(12-41); (cyclo 30-33)[Nle21, 38, Cml27,40, Glu30, Lys33]Ac-h/rCRF(13-41); (cyclo 30-33)[Nle21,38, Cml27,40, Glu30, Lys33]Ac-h/rCRF(14-41); (cyclo 30-33)[Nle21,38, Cml27,40, Glu30, Lys33]Ac-h/rCRF(15-41); (cyclo 30-33)[Nle21,38, Cml27,40, Glu30, Lys33]Ac-h/rCRF(16-41); (cyclo 30-33)[Nle21,38, Cml27, 40, Glu30, Lys33]Ac-h/rCRF(17-41); (cyclo 30-33)[Nle21, 38, Cml27,40, Glu30, Lys33]Ac-h/rCRF(18-41); (cyclo 30-33)[Nle21,38, Cml27,40, Glu30, Lys33]Ac-h/rCRF(19-41); (cyclo 30-33)[Nle21,38, Cml27,40, Glu30, Lys33]Ac-h/rCRF(20-41); (cyclo 30-33)[Nle21,38, Cml27,40, Glu30, Lys33]Ac-h/rCRF(21-41); (cyclo 30-33)[Cml27,40 Glu30, Lys33, Nle38]Ac-h/rCRF(22-41); (cyclo 30-33)[Cml27,40 Glu30, Lys33, Nle38]Ac-h/rCRF(23-41); (cyclo 30-33) [Cml27,40 Glu30, Lys33, Nle38]Ac-h/rCRF(24-41); (cyclo 30-33)[Cml27,40 Glu30, Lys33, Nle38]Ac-h/rCRF(25-41); (cyclo 30-33)[Cml27,40 Glu30, Lys33, Nle38]Ac-h/rCRF (26-41); (cyclo 30-33)[Cml27,40 Glu30, Lys33, Nle38]Ac-h/rCRF(27-41); (cyclo 30-33)[Glu30, Lys33, Nle38, Cml40] Ac-h/rCRF(28-41); (cyclo 30-33)[Glu30, Lys33, Nle38, Cml40]Ac-h/rCRF(29-41); and/or (cyclo 30-33)[Glu30, Lys33, Nle38, Cml40]Ac-h/rCRF(30-41).

The effects of treatment with each foregoing astressin B fragment on hair growth and pigmentation in the CRF-OE mice are observed every other day in the first 2 weeks following the initial injection and twice a week for at least 2 months total time. Hair growth in CRF-OE mice is assessed using the hair growth scale described in Example 1. The general conditions of treated and control mice, such as weight, back skin thickness, hair luster, skin wounds and indurations, are noted.

At all time points at least four weeks after the final injection, all mice injected with an astressin B fragment exhibit fully (or nearly fully) grown hair in the test area whereas all saline-injected mice remained bald in the test area. The general conditions of control and treated mice are substantially the same throughout the treatment and observation periods.

Example 9

Astressin B Fragments Prevent Hair Loss

A representative number of young male and/or female CRF-OE mice (e.g., 6 or 8 mice) that have not yet developed the alopecia phenotype are injected subcutaneously or intraperitoneally with 5 μg of an astressin B fragment in 0.1 ml sterile saline once per day for 5 consecutive days. Each subcutaneous injection is given in a single puncture located along or about the midline of the back. CRF-OE mice similarly injected with 0.1 ml saline alone (or 5 μg astressin 2B in 0.1 ml saline) are used as negative controls. Astressin B fragments are as described in Example 8. Alternatively, topical astressin B can be applied to the mouse's back, for example 0.05 mg, 0.5 mg, 5 mg, 50 mg, or 500 mg of an astressin B fragment once daily for at least five consecutive days. Similar methods can be used to demonstrate the ability of any cyclic CRF antagonist to prevent hair loss (in any mammalian subject of interest).

The effects of treatment with each astressin B fragment on hair loss and pigmentation in the CRF-OE mice are observed every other day in the first 2 weeks following the initial injection and twice a week for at least 2 months total time. Hair growth in CRF-OE mice is assessed using the hair growth scale described in Example 1. The general conditions of treated and control mice, such as weight, back skin thickness, hair luster, skin wounds and indurations, are noted.

At all time points, all mice injected with an astressin B fragment exhibit fully (or nearly fully) grown hair in the test area whereas all saline-injected (or astressin 2B-injected) mice develop ultimately alopecia in the test area. The general conditions of control and treated mice are substantially the same throughout the treatment and observation periods.

Example 10

Cyclic CRF Antagonists Promote Hair Growth

This example describes methods that can be used to demonstrate the ability of one or more cyclic CRF antagonists to promote hair growth in a mammalian subject. Although mice are particularly described, one skilled in the art will appreciate that other laboratory animals and human subjects can be used, and doses adjusted accordingly (for example based on the weight of the subject, or the area to which the peptide is to be applied). Similarly although particular modes of administration are described, one will appreciate that variations can be made (such as those disclosed herein and those known in the art).

A representative number of adult male and/or female CRF-OE mice (e.g., 6 or 8 mice) with fully developed alopecia are administered therapeutically effective amounts of one or more cyclic CRF antagonists. Any method of administration can be used, including injection, transdermal/topical delivery, or combinations thereof.

In one example, therapeutic peptides are administered via injection. For example, mice can be injected subcutaneously or intraperitoneally with at least 0.05 μg, at least 0.5 μg, at least 5 μg, at least 50 μg, or at least 500 μg of one or more therapeutic peptides (for example 0.5-50 μg peptide, 0.5-10 μg peptide, or 5 μg peptide). The peptide can be administered in 0.1 ml sterile saline (or 5% mannitol) once per day for at least 5 consecutive days, such as at least 10 days, at least 30 days, or at least 60 days. Subcutaneous injections are given in a single puncture located along or about the midline of the back. As a negative control, CRF-OE mice receive saline alone (such as 10-100 μl) or 5 μg astressin 2B in 0.1 ml saline.

In another example, therapeutic peptides are administered topically or transdermally. For example, a topical/transdermal preparation that includes at least 0.05 mg, at least 0.5 mg, at least 5 mg, at least 50 mg, or at least 500 mg of one or more therapeutic peptides (for example 0.5-50 mg peptide, 0.5-10 mg peptide, or 5 mg peptide). The peptide can be administered in a carrier, for example a hydrophilic cream or lotion or liposome vehicle (such as Novasome A, which contains ethoxydiglycol (25%), glyceryl dilaurate (8%), propylene glycol dicaylate (4%), cholesterol (1.5%), and ceteraryl alcohol/cetearyl glucoside (1%)). For example, 10-30 μl of carrier (such as 20 μl) can be administered to a rodent (such as a mouse) and 0.1 ml to 1 ml carrier (such as 0.1 ml to 0.5 ml) can be administered to larger mammals (such as a human or non-human primate) once per day for at least 5 consecutive days, such as at least 10 days, at least 30 days, or at least 60 days, Topical/transdermal formulations can given by applying the formulation to the skin on the mouse's back (for example in areas where there is no visible hair). In some examples, microneedles are inserted into the back for delivery of the peptide. If desired, treated areas can be covered with a plastic lap. As a negative control, CRF-OE mice receive carrier alone (such as with 10-100 µl) or 5 mg astressin 2B.

The effects of treatment with one or more cyclic CRF antagonists on hair growth and skin pigmentation in the CRS-OE mice are observed every other day in the first 2 weeks following the initial administration and twice a week for at least 2 months total time. Hair growth in CRF-OE mice is assessed using the hair growth scale described in Example 1. The general conditions of treated and control mice, such as weight, back skin thickness, hair luster, skin wounds and indurations, are noted.

At all time points at least four weeks after the final administration, all mice administered one or more cyclic CRF antagonists exhibit fully (or nearly fully) grown hair in the test area whereas all saline-treated (or astressin 2B-treated) mice remain bald in the test area. The general conditions of control and treated mice are substantially the same throughout the treatment and observation periods.

Example 11

Cyclic CRF Antagonists Prevent Hair Loss

This example describes methods that can be used to demonstrate the ability of one or more cyclic CRF antagonists to prevent hair loss in a mammalian subject. Although mice are particularly described, one skilled in the art will appreciate that other laboratory animals and human subjects can be used, and doses adjusted accordingly (for example based on the weight of the subject, or the area to which the peptide is to be applied). Similarly, although particular modes of administration are described, one will appreciate that variations can be made (such as those disclosed herein and those known in the art).

A representative number of young male and/or female CRF-OE mice (e.g. 6 or 8 mice) that have not yet developed the alopecia phenotype are administered therapeutically effective amounts of one or more cyclic CRF antagonists. Any method of administration can be used, including injection, transdermal/topical delivery, or combinations thereof.

In one example, therapeutic peptides are administered via injection. For example, mice can be injected subcutaneously or intraperitoneally with at least 0.05 µg, at least 0.5 µg, at least 5 µg, at least 50 µg, or at least 500 µg of one or more therapeutic peptides (for example 0.5-50 µg peptide, 0.5-10 µg peptide, or 5 µg peptide). The peptide can be administered in 0.1 ml sterile saline (or 5% mannitol) once per day for at least 5 consecutive days, such as at least 10 days, at least 30 days, or at least 60 days. Subcutaneous injections are given in a single puncture located along or about the midline of the back. As a negative control, CRF-OE mice receive saline alone (such as 10-100 µl) or 5 µg astressin 2B in 0.1 ml saline.

In another example, therapeutic peptides are administered topically or transdermally. For example, a topical/transdermal preparation that includes at least 0.05 mg, at least 0.5 mg, at least 5 mg, at least 50 mg, or at least 500 mg of one or more therapeutic peptides (for example 0.5-50 mg peptide, 0.5-10 mg peptide, or 5 mg peptide). The peptide can be administered in a carrier, for example a hydrophilic cream or lotion or liposome vehicle (such as Novasome A, which contains ethoxydiglycol (25%), glyceryl dilaurate (8%), propylene glycol dicaylate (4%), cholesterol (1.5%), and ceteraryl alcohol/cetearyl glucoside (1%)). For example, 10-30 µl of carrier (such as 20 µl) can be administered to a rodent (such as a mouse) and 0.1 ml to 1 ml carrier (such as 0.1 ml to 0.5 ml) can be administered to larger mammals (such as a human or non-human primate) once per day for at least 5 consecutive days, such as at least 10 days, at least 30 days, or at least 60 days. Topical/transdermal formulations can given by applying the formulation to the skin on the mouse's back (for example in areas where there is no visible hair). In some examples, microneedles are inserted into the back for delivery of the peptide. If desired, treated areas can be covered with a plastic lap. As a negative control, CRF-OE mice receive carrier alone (such as with 10-100 µl) or 5 mg astressin 2B.

The effects of treatment with one or more cyclic CRF antagonists on hair loss and skin pigmentation in the CRF-OE mice are observed every other day in the first 2 weeks following the initial administration and twice a week for at least 2 months total time. Hair growth in CRF-OE mice is assessed using the hair growth scale described in Example 1. The general conditions of treated and control mice, such as weight, back skin thickness hair luster, skin wounds and indurations, are noted.

At all time points at least four weeks after the final administration, all mice administered one or more cyclic C(R antagonists exhibit fully (or nearly fully) grown hair in the test area whereas all saline-treated (or astressin 2B-treated) mice ultimately develop alopecia in the test area. The general conditions of control and treated mice are substantially the same throughout the treatment and observation periods.

Example 12

Synthesis of Astressin B and its Analogs

All analogs, like (cyclo 30-33)[Glu30, Aib31, Glu32, Lys33, Cha38, Asp39]Ac-hCRF(30-41)) and (cyclo 30-33) [Glu30, Aib31, Glu32, Lys33, Cha38, Asp39, $C_\alpha$MeLeu40] Ac-hCRF(30-41)) (short astressin analogs), cyclo(31-34) [DPhe12, Nle21,38, Glu31, Lys34]Ac-hCRF(4-41)) (stressin$_1$) (cyclo 30-33)[DPhe12, Nle21,38, Glu30, Lys33] hCRF(12-41)) (astressin), (cyclo 30-33)[DPhe12, Nle21,38, $C_\alpha$MeLeu27,40, Glu30, Lys33]Ac-hCRF(9-41)) (astressin B), cyclo(31-34)[DPhe11, His12, $C_\alpha$MeLeu13,39, Nle17, Glu31, Lys34]Ac-Sau(8-40) (astressin 2B), were synthesized either manually or automatically on a methylbenzhydrylamine (MBHA) resin (Miranda et al., *J. Med. Chem.*, 37:1450-1459, 1994) using the solid phase approach and the Boc strategy with orthogonal protection of the side chain of the lysine (Fmoc) and glutamic acid (OFm) residues to be cyclized (Felix et al., *Int. J. Pep. Prot. Res.*, 32:441)-454, 1988).

Amino acids derivatives Boc-Ala, Boc-Arg(Tos), Boc-Asn(Xan), Boc-Asp(cHex), Boc-Gln(Xan), Boc-Glu(cHex), Boc-His(Tos), Boc-Ile, Boc-Leu, Boc-Lys(2-Cl-Z), Boc-Met, Boc-Nle, Boc-Phe, Boc-Pro, Boc-Ser(Bzl), Boc-Thr (Bzl), Boc-Val are commercially available. Boc-Glu(OFm), Boc-Lys(Fmoc) and Boc-L-$C_\alpha$MeLeu were synthesized as described earlier (Felix et al., *Int. J. Pep. Prot. Res.*, 31:231-238, 1988; Hernandez et al., *J. Med. Chem.*, 36:2860-2867, 1993). All solvents were reagent grade or better. Trifluoroacetic acid (TFA), 50-60% in DCM (1% m-cresol), was used to remove the Boc group. Main chain assembly was mediated in most cases by diisopropylcarbodiimide (DIG). Three-fold excess of protected amino acid was used based on the original substitution of the MBHA resin. The solid phase synthesis of the C$_\alpha$-substituted CRF analogues (astressin B (cyclo 30-33)[Glu30, Aib31, Lys33, Cha38, Asp39, C$_\alpha$MeLeu40]Ac-hCRF(30-41)) and astressin 2B) exhibited some difficulties that were remedied using a 1:4 mixture of TBTU/HOBt (pH 9-10, 2 hours). In case of incomplete couplings, monitored by Kaiser's ninhydrin test (Kaiser et al. *Anal. Biochem.*, 34:595-598, 1970), couplings were repeated followed by acetylation (excess of acetic anhydride in dichloromethane (DCM) for 15 minutes). γ-OFm-Glu and ε-Fmoc-Lys were deblocked using 20% piperidine in N-methyl-2-pyrrolidone (NMP) after complete assembly of the peptide resin. Lactam formation was mediated by TBTU/HOBt in NMP for 1 hour. Good results were obtained when the peptide chain was assembled in its entirety prior to cleavage of the Fmoc and OFm protecting groups and cyclized as described earlier (Miranda et al., *J. Med. Chem.*, 37:1450-1459, 1994).

The peptide resins were treated with anhydrous HF to liberate the fully deblocked crude peptides. After elimination of HF under vacuum, crude peptides were washed with peroxide-free diethyl ether and extracted with 0.1% TFA in 60% acetonitrile/water. Then, crude peptides were purified using preparative RP-HPLC and two or three successive solvent systems (A: TEAP at pH 2.25 and/or pH 6.5 and 0.1% TFA, B: 60% acetonitrile/water) (Hoeger et al., *Biochromatography*, 2:134-142, 1987; Miller and Rivier, *Biopolymers*, 40:265-317, 1996; Rivier, *J. Liq. Chromatogr.*, 1:343-367, 1978).

Analytical RP-HPLC analysis using independent HPLC and CZE criteria revealed that the purity of all peptides was higher than 95%. Calculated values for protonated molecule ions were in agreement with those observed for each peptides using Matrix-assisted laser desorption-ionization mass spectroscopy (MALDI-MS) on an ABI-Perseptive DE STR instrument ((cyclo 30-33)[Glu30, Aib31, Glu32, Lys33, Cha38, Asp39]Ac-hCRF(30-41)) (1518.98 uma), (cyclo 30-33)[Glu30, Aib31, Glu32, Lys33, Cha38, Asp39, C$_\alpha$MeLeu40]Ac-hCRF(30-41)) (1532.74 uma), cyclo(31-34)[DPhe12, Nle21,38, Glu31, Lys34]Ac-hCRF(4-41)) (stressin1, 4470.5 uma), (cyclo 30-33)[DPhe12, Nle21,38, Glu30, Lys33]Ac-hCRF(12-41)) (astressin, 3562.1 uma), (cyclo 30-33)[DPhe12, Nle21,38, C$_\alpha$MeLeu27,40, Glu30, Lys33]Ac-hCRF(9-41)) (astressin B, 3961.3 uma) and cyclo (31-34)[DPhe11, His12, C$_\alpha$MeLeu13,39, Nle17, Glu31, Lys34]Ac-Sau(8-40)) (astressin 2B, 4040.3 uma)).

While this disclosure has been described with an emphasis upon particular embodiments, it will be obvious to those of ordinary skill in the art that variations of) the particular embodiments may be used and it is intended that the disclosure may be practiced otherwise than as specifically described herein. Accordingly, this disclosure includes all modifications encompassed within the spirit and scope of the disclosure as defined by the following claims:

---

The invention claimed is:

1. A method for promoting hair growth in a subject, comprising:
administering to a subject having a decrease in the number of hair follicles in the anagen phase an effective amount of a cyclic peptide non-selective antagonist of corticotrophin release factor (CRF) receptors 1 and 2 that increases the number of hair follicles in the anagen phase, wherein the antagonist is astressin B and administration is by subcutaneous, intraperitoneal, topical or transdermal delivery;
increasing the number of hair follicles in the anagen phase; and
promoting hair growth in the subject.

2. The method of claim 1, wherein administering the astressin B comprises topical administration, intraperitoneal injection, intravenous injection, subcutaneous injection, transdermal injection, or intramuscular injection.

3. The method of claim 1, wherein the astressin B is administered to an area of alopecia-affected skin.

4. The method of claim 1, wherein the effective amount is from about 1 μg/kg body weight to about 500 μg/kg body weight.

5. The method of claim 1, wherein the subject is a human.

6. The method of claim 5, wherein the astressin B is administered to the scalp of the human.

7. The method of claim 1, wherein the subject is a non-human animal.

8. The method of claim 1, wherein the decrease in the number of hair follicles in the anagen phase in the subject results from a health disorder or a therapeutic treatment.

9. The method of claim 8, wherein the health disorder is alopecia areata, traction alopecia, folliculitis alopecia, telogen effluvium, loose-anagen syndrome, toxic alopecia, acquired immune deficiency (AID), hypothyroidism, hyperthyroidism, lupus erythematosus, diabetes, iron deficiency, syphilis, zinc deficiency, trichotillomania, or Cushing syndrome.

10. The method of claim 8, wherein the therapeutic treatment is chemotherapy or radiation therapy.

11. The method of claim 8, wherein the therapeutic treatment comprises administration of cyclophosphamide, daunorubicin, doxorubicin, etoposide, ifosamide, paclitaxel, docetaxel, trimethadione, tacrolimus, lithium, atenolol, metoprolol, nadolol, propranolol, timolol, warfarin, heparin, allopurinol, amphetamines, levodopa, bromocriptine and pergolide, pramipexole, ropinerole, vitamin A, isotretinoin, etretinate, tricyclic antidepressants, amphetamines, bupropion, selegeline, clofibrate, gemfibrozil, cimetidine, ranitidine, famotidine, auranofin, indomethacin, naproxen, sulindac, methotrexate, lisinopril, carbimazole, iodine, thiocyanate, or thiouracil.

12. The method of claim 10, wherein the radiation therapy comprises a dose of radiation less than about 6,000 cGy.

13. The method of claim 1, wherein administering the astressin B comprises subcutaneous injection.

14. The method of claim 13, wherein the effective amount is from about 0.1 μg to about 14 mg per injection site.

15. The method of claim 1, wherein the effective amount is from about 1 μg/kg body weight to about 1000 μg/kg body weight.

16. The method of claim 1, wherein the effective amount is from about 5 μg to 5 mg of astressin B per dose.

17. The method of claim 1, wherein the subject has alopecia.

18. A method of preventing hair loss in a subject, comprising:
administering to a subject susceptible to hair loss a therapeutically effective amount of a cyclic peptide non-selective antagonist of corticotrophin release factor (CRF) receptors 1 and 2 that prevents hair loss, wherein the antagonist is astressin B and administration is by subcutaneous, intraperitoneal, topical or transdermal delivery;
assessing hair growth in the subject; and
preventing hair loss in the subject.

19. The method of claim 18, wherein the subject is at risk for developing alopecia.

* * * * *

SEQUENCE LISTING

```
<160> NUMBER OF SEQ ID NOS: 15

<210> SEQ ID NO 1
<211> LENGTH: 41
<212> TYPE: PRT
<213> ORGANISM: Homo sapiens
<220> FEATURE:
<221> NAME/KEY: MOD RES
<222> LOCATION: (41)..(41)
<223> OTHER INFORMATION: AMIDATION

<400> SEQUENCE: 1

Ser Glu Glu Pro Pro Ile Ser Leu Asp Leu Thr Phe His Leu Leu Arg
1               5                   10                  15

Glu Val Leu Glu Met Ala Arg Ala Glu Gln Leu Ala Gln Gln Ala His
            20                  25                  30

Ser Asn Arg Lys Leu Met Glu Ile Ile
        35                  40

<210> SEQ ID NO 2
<211> LENGTH: 33
<212> TYPE: PRT
<213> ORGANISM: Artificial sequence
<220> FEATURE:
<223> OTHER INFORMATION: Cyclic corticotrophin releasing factor
      antagonist peptide
<220> FEATURE:
<221> NAME/KEY: MISC_FEATURE
<222> LOCATION: (2)..(2)
<223> OTHER INFORMATION: Xaa can be Leu or Calpha CH3 L Leu
<220> FEATURE:
<221> NAME/KEY: MISC_FEATURE
<222> LOCATION: (3)..(3)
<223> OTHER INFORMATION: Xaa can be Thr or Ser
<220> FEATURE:
<221> NAME/KEY: MISC_FEATURE
<222> LOCATION: (4)..(4)
<223> OTHER INFORMATION: Xaa can be DPhe, DLeu, DTyr, DTrp, DCpa, DNal,
      DPal, Phe, or Tyr
<220> FEATURE:
```

```
<221> NAME/KEY: MISC_FEATURE
<222> LOCATION: (5)..(5)
<223> OTHER INFORMATION: Xaa can be His, Tyr, or Glu
<220> FEATURE:
<221> NAME/KEY: MISC_FEATURE
<222> LOCATION: (6)..(6)
<223> OTHER INFORMATION: Xaa can be Leu, Cml, or Ile
<220> FEATURE:
<221> NAME/KEY: MISC_FEATURE
<222> LOCATION: (7)..(7)
<223> OTHER INFORMATION: Xaa can be Leu, Cml, or Ile
<220> FEATURE:
<221> NAME/KEY: MISC_FEATURE
<222> LOCATION: (9)..(9)
<223> OTHER INFORMATION: Xaa can be Glu, Cml, Asn or Lys
<220> FEATURE:
<221> NAME/KEY: MISC_FEATURE
<222> LOCATION: (10)..(10)
<223> OTHER INFORMATION: Xaa can be Val, Nle, Cml, or Met
<220> FEATURE:
<221> NAME/KEY: MISC_FEATURE
<222> LOCATION: (11)..(11)
<223> OTHER INFORMATION: Xaa can be Leu or Ile
<220> FEATURE:
<221> NAME/KEY: MISC_FEATURE
<222> LOCATION: (12)..(12)
<223> OTHER INFORMATION: Xaa can be Glu, DGlu, or His
<220> FEATURE:
<221> NAME/KEY: MISC_FEATURE
<222> LOCATION: (13)..(13)
<223> OTHER INFORMATION: Xaa can be Nle or Met
<220> FEATURE:
<221> NAME/KEY: MISC_FEATURE
<222> LOCATION: (14)..(14)
<223> OTHER INFORMATION: Xaa can be Ala, DAla, Aib, Asp, Thr, DThr, Glu,
      or DGlu
<220> FEATURE:
<221> NAME/KEY: MISC_FEATURE
<222> LOCATION: (15)..(15)
<223> OTHER INFORMATION: Xaa can be Arg or Lys
<220> FEATURE:
<221> NAME/KEY: MISC_FEATURE
<222> LOCATION: (16)..(16)
<223> OTHER INFORMATION: Xaa can be Ala, Aib, Cml, or Val
<220> FEATURE:
<221> NAME/KEY: MISC_FEATURE
<222> LOCATION: (17)..(17)
<223> OTHER INFORMATION: Xaa can be Glu or Asp
<220> FEATURE:
<221> NAME/KEY: MISC_FEATURE
<222> LOCATION: (18)..(18)
<223> OTHER INFORMATION: Xaa can be Gln, Asn, or Lys
<220> FEATURE:
<221> NAME/KEY: MISC_FEATURE
<222> LOCATION: (19)..(19)
<223> OTHER INFORMATION: Xaa can be Leu, Cml, or Ala
<220> FEATURE:
<221> NAME/KEY: MISC_FEATURE
<222> LOCATION: (20)..(20)
<223> OTHER INFORMATION: Xaa can be Ala, Aib, Lys, or Arg
<220> FEATURE:
<221> NAME/KEY: MISC_FEATURE
<222> LOCATION: (21)..(21)
<223> OTHER INFORMATION: Xaa can be Gln, Aib, Glu, or Ala
<220> FEATURE:
<221> NAME/KEY: MISC_FEATURE
<222> LOCATION: (22)..(22)
<223> OTHER INFORMATION: Xaa can be cGlu or cASP
<220> FEATURE:
<221> NAME/KEY: MISC_FEATURE
<222> LOCATION: (23)..(23)
<223> OTHER INFORMATION: Xaa can be Aib, DAla, or any L-alpha-amino acid
      with the exception of Cys
<220> FEATURE:
<221> NAME/KEY: MISC_FEATURE
<222> LOCATION: (24)..(24)
<223> OTHER INFORMATION: Xaa can be His, Glu, DHis, Leu, Lys, Ala, or
      Aib
<220> FEATURE:
```

```
<221> NAME/KEY: MISC_FEATURE
<222> LOCATION: (25)..(25)
<223> OTHER INFORMATION: Xaa can be cLys, cOrn, cDbu, or cHly
<220> FEATURE:
<221> NAME/KEY: MISC_FEATURE
<222> LOCATION: (26)..(26)
<223> OTHER INFORMATION: Xaa can be Asn, Ala, or Lys
<220> FEATURE:
<221> NAME/KEY: MISC_FEATURE
<222> LOCATION: (27)..(27)
<223> OTHER INFORMATION: Xaa can be Arg, Ala, or Lys
<220> FEATURE:
<221> NAME/KEY: MISC_FEATURE
<222> LOCATION: (28)..(28)
<223> OTHER INFORMATION: Xaa can be Lys, Orn, Arg, Har, Cml, Leu, or Ala
<220> FEATURE:
<221> NAME/KEY: MISC_FEATURE
<222> LOCATION: (29)..(29)
<223> OTHER INFORMATION: Xaa can be Leu, Cml, Tyr, or Ala
<220> FEATURE:
<221> NAME/KEY: MISC_FEATURE
<222> LOCATION: (30)..(30)
<223> OTHER INFORMATION: Xaa can be Nle, Cha, Met, Cml, or Phe
<220> FEATURE:
<221> NAME/KEY: MISC_FEATURE
<222> LOCATION: (31)..(31)
<223> OTHER INFORMATION: Xaa can be Glu, Asp, Aib, or Ala
<220> FEATURE:
<221> NAME/KEY: MISC_FEATURE
<222> LOCATION: (32)..(32)
<223> OTHER INFORMATION: Xaa can be Ile, Cml, or Ala
<220> FEATURE:
<221> NAME/KEY: MISC_FEATURE
<222> LOCATION: (33)..(33)
<223> OTHER INFORMATION: Xaa can be Ile, Ala, Leu, Val, Aib, Gly, Cml,
      Nle, Nva, Gln, Asn, or Phe

<400> SEQUENCE: 2

Asp Xaa Xaa Xaa Xaa Xaa Xaa Arg Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa

<210> SEQ ID NO 3
<211> LENGTH: 27
<212> TYPE: PRT
<213> ORGANISM: Artificial sequence
<220> FEATURE:
<223> OTHER INFORMATION: Cyclic corticotrophin releasing factor
      antagonist peptide
<220> FEATURE:
<221> NAME/KEY: MISC_FEATURE
<222> LOCATION: (1)..(1)
<223> OTHER INFORMATION: Xaa can be Leu, Cml, or Ile
<220> FEATURE:
<221> NAME/KEY: MISC_FEATURE
<222> LOCATION: (3)..(3)
<223> OTHER INFORMATION: Xaa can be Glu, Cml, Asn or Lys
<220> FEATURE:
<221> NAME/KEY: MISC_FEATURE
<222> LOCATION: (4)..(4)
<223> OTHER INFORMATION: Xaa can be Val, Nle, Cml, or Met
<220> FEATURE:
<221> NAME/KEY: MISC_FEATURE
<222> LOCATION: (5)..(5)
<223> OTHER INFORMATION: Xaa can be Leu or Ile
<220> FEATURE:
<221> NAME/KEY: MISC_FEATURE
<222> LOCATION: (6)..(6)
<223> OTHER INFORMATION: Xaa can be Glu, DGlu, or His
<220> FEATURE:
<221> NAME/KEY: MISC_FEATURE
<222> LOCATION: (7)..(7)
<223> OTHER INFORMATION: Xaa can be Nle or Met
```

-continued

```
<220> FEATURE:
<221> NAME/KEY: MISC_FEATURE
<222> LOCATION: (8)..(8)
<223> OTHER INFORMATION: Xaa can be Ala, DAla, Aib, Asp, Thr, DThr, Glu,
      or DGlu
<220> FEATURE:
<221> NAME/KEY: MISC_FEATURE
<222> LOCATION: (9)..(9)
<223> OTHER INFORMATION: Xaa can be Arg or Lys
<220> FEATURE:
<221> NAME/KEY: MISC_FEATURE
<222> LOCATION: (10)..(10)
<223> OTHER INFORMATION: Xaa can be Ala, Aib, Cml, or Val
<220> FEATURE:
<221> NAME/KEY: MISC_FEATURE
<222> LOCATION: (11)..(11)
<223> OTHER INFORMATION: Xaa can be Glu or Asp
<220> FEATURE:
<221> NAME/KEY: MISC_FEATURE
<222> LOCATION: (12)..(12)
<223> OTHER INFORMATION: Xaa can be Gln, Asn, or Lys
<220> FEATURE:
<221> NAME/KEY: MISC_FEATURE
<222> LOCATION: (13)..(13)
<223> OTHER INFORMATION: Xaa can be Leu Cml, or Ala
<220> FEATURE:
<221> NAME/KEY: MISC_FEATURE
<222> LOCATION: (14)..(14)
<223> OTHER INFORMATION: Xaa can be Ala, Aib, Lys, or Arg
<220> FEATURE:
<221> NAME/KEY: MISC_FEATURE
<222> LOCATION: (15)..(15)
<223> OTHER INFORMATION: Xaa can be Gln, Aib, Glu, or Ala
<220> FEATURE:
<221> NAME/KEY: MISC_FEATURE
<222> LOCATION: (16)..(16)
<223> OTHER INFORMATION: Xaa can be cGlu or cAsp
<220> FEATURE:
<221> NAME/KEY: MISC_FEATURE
<222> LOCATION: (17)..(17)
<223> OTHER INFORMATION: Xaa can be Aib, DAla, or any L-alpha-amino acid
      with the exception of Cys
<220> FEATURE:
<221> NAME/KEY: MISC_FEATURE
<222> LOCATION: (18)..(18)
<223> OTHER INFORMATION: Xaa can be His, Glu, DHis, Leu, Lys, Ala, or
      Aib
<220> FEATURE:
<221> NAME/KEY: MISC_FEATURE
<222> LOCATION: (19)..(19)
<223> OTHER INFORMATION: Xaa can be cLys, cOrn, cDbu, or cHly
<220> FEATURE:
<221> NAME/KEY: MISC_FEATURE
<222> LOCATION: (20)..(20)
<223> OTHER INFORMATION: Xaa can be Asn, Ala, or Lys
<220> FEATURE:
<221> NAME/KEY: MISC_FEATURE
<222> LOCATION: (21)..(21)
<223> OTHER INFORMATION: Xaa can be Arg, Ala, or Lys
<220> FEATURE:
<221> NAME/KEY: MISC_FEATURE
<222> LOCATION: (22)..(22)
<223> OTHER INFORMATION: Xaa can be Lys, Orn, Arg, Har, Cml, Leu, or Ala
<220> FEATURE:
<221> NAME/KEY: MISC_FEATURE
<222> LOCATION: (23)..(23)
<223> OTHER INFORMATION: Xaa can be Leu, Cml, Tyr, or Ala
<220> FEATURE:
<221> NAME/KEY: MISC_FEATURE
<222> LOCATION: (24)..(24)
<223> OTHER INFORMATION: Xaa can be Nle, Cha, Met, Cml, or Phe
<220> FEATURE:
<221> NAME/KEY: MISC_FEATURE
<222> LOCATION: (25)..(25)
<223> OTHER INFORMATION: Xaa can be Glu, Asp, Aib, or Ala
<220> FEATURE:
<221> NAME/KEY: MISC_FEATURE
<222> LOCATION: (26)..(26)
<223> OTHER INFORMATION: Xaa can be Ile, Cml, or Ala
```

```
<220> FEATURE:
<221> NAME/KEY: MISC_FEATURE
<222> LOCATION: (27)..(27)
<223> OTHER INFORMATION: Xaa can be Ile, Ala, Leu, Val, Aib, Gly, Cml,
      Nle, Nva, Gln, Asn, or Phe

<400> SEQUENCE: 3

Xaa Arg Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25

<210> SEQ ID NO 4
<211> LENGTH: 16
<212> TYPE: PRT
<213> ORGANISM: Artificial sequence
<220> FEATURE:
<223> OTHER INFORMATION: Cyclic corticotrophin releasing factor
      antagonist peptide
<220> FEATURE:
<221> NAME/KEY: MISC_FEATURE
<222> LOCATION: (1)..(1)
<223> OTHER INFORMATION: Xaa can be Gln, Asn, or Lys
<220> FEATURE:
<221> NAME/KEY: MISC_FEATURE
<222> LOCATION: (2)..(2)
<223> OTHER INFORMATION: Xaa can be Leu, Cml, or Ala
<220> FEATURE:
<221> NAME/KEY: MISC_FEATURE
<222> LOCATION: (3)..(3)
<223> OTHER INFORMATION: Xaa can be Ala, Aib, Lys, or Arg
<220> FEATURE:
<221> NAME/KEY: MISC_FEATURE
<222> LOCATION: (4)..(4)
<223> OTHER INFORMATION: Xaa can be Gln, Aib, Glu, or Ala
<220> FEATURE:
<221> NAME/KEY: MISC_FEATURE
<222> LOCATION: (5)..(5)
<223> OTHER INFORMATION: Xaa can be cGlu or cAsp
<220> FEATURE:
<221> NAME/KEY: MISC_FEATURE
<222> LOCATION: (6)..(6)
<223> OTHER INFORMATION: Xaa can be Aib, DAla, or any L-alpha-amino
      acid with the exception of Cys
<220> FEATURE:
<221> NAME/KEY: MISC_FEATURE
<222> LOCATION: (7)..(7)
<223> OTHER INFORMATION: Xaa can be His, Glu, DHis, Leu, Lys, Ala, or
      Aib
<220> FEATURE:
<221> NAME/KEY: MISC_FEATURE
<222> LOCATION: (8)..(8)
<223> OTHER INFORMATION: Xaa can be cLys, cOrn, cDbu, or cHly
<220> FEATURE:
<221> NAME/KEY: MISC_FEATURE
<222> LOCATION: (9)..(9)
<223> OTHER INFORMATION: Xaa can be Asn, Ala, or Lys
<220> FEATURE:
<221> NAME/KEY: MISC_FEATURE
<222> LOCATION: (10)..(10)
<223> OTHER INFORMATION: Xaa can be Arg, Ala, or Lys
<220> FEATURE:
<221> NAME/KEY: MISC_FEATURE
<222> LOCATION: (11)..(11)
<223> OTHER INFORMATION: Xaa can be Lys, Orn, Arg, Har, Cml, Leu, or Ala
<220> FEATURE:
<221> NAME/KEY: MISC_FEATURE
<222> LOCATION: (12)..(12)
<223> OTHER INFORMATION: Xaa can be Leu, Cml, Tyr, or Ala
<220> FEATURE:
<221> NAME/KEY: MISC_FEATURE
<222> LOCATION: (13)..(13)
<223> OTHER INFORMATION: Xaa can be Nle, Cha, Met, Cml, or Phe
<220> FEATURE:
<221> NAME/KEY: MISC_FEATURE
<222> LOCATION: (14)..(14)
```

```
<223> OTHER INFORMATION: Xaa can be Glu, Asp, Aib, or Ala
<220> FEATURE:
<221> NAME/KEY: MISC_FEATURE
<222> LOCATION: (15)..(15)
<223> OTHER INFORMATION: Xaa can be Ile, Cml, or Ala
<220> FEATURE:
<221> NAME/KEY: MISC_FEATURE
<222> LOCATION: (16)..(16)
<223> OTHER INFORMATION: Xaa can be Ile, Ala, Leu, Val, Aib, Gly, Cml,
      Nle, Nva, Gln, Asn, or Phe

<400> SEQUENCE: 4

Xaa Xaa Xaa Xaa Xaa Xaa Xaa Xaa Xaa Xaa Xaa Xaa Xaa Xaa Xaa Xaa
1               5                   10                  15

<210> SEQ ID NO 5
<211> LENGTH: 12
<212> TYPE: PRT
<213> ORGANISM: Artificial sequence
<220> FEATURE:
<223> OTHER INFORMATION: Cyclic corticotrophin releasing factor
      antagonist peptide
<220> FEATURE:
<221> NAME/KEY: MISC_FEATURE
<222> LOCATION: (1)..(1)
<223> OTHER INFORMATION: Xaa can be cGlu or cAsp
<220> FEATURE:
<221> NAME/KEY: MISC_FEATURE
<222> LOCATION: (2)..(2)
<223> OTHER INFORMATION: Xaa can be Aib, DAla, or any L-alpha-amino acid
      with the exception of Cys
<220> FEATURE:
<221> NAME/KEY: MISC_FEATURE
<222> LOCATION: (3)..(3)
<223> OTHER INFORMATION: Xaa can be His, Glu, DHis, Leu, Lys, Ala, or
      Aib
<220> FEATURE:
<221> NAME/KEY: MISC_FEATURE
<222> LOCATION: (4)..(4)
<223> OTHER INFORMATION: Xaa can be cLys, cOrn, cDbu, or cHly
<220> FEATURE:
<221> NAME/KEY: MISC_FEATURE
<222> LOCATION: (5)..(5)
<223> OTHER INFORMATION: Xaa can be Asn, Ala, or Lys
<220> FEATURE:
<221> NAME/KEY: MISC_FEATURE
<222> LOCATION: (6)..(6)
<223> OTHER INFORMATION: Xaa can be Arg, Ala, or Lys
<220> FEATURE:
<221> NAME/KEY: MISC_FEATURE
<222> LOCATION: (7)..(7)
<223> OTHER INFORMATION: Xaa can be Lys, Orn, Arg, Har, Cml, Leu, or Ala
<220> FEATURE:
<221> NAME/KEY: MISC_FEATURE
<222> LOCATION: (8)..(8)
<223> OTHER INFORMATION: Xaa can be Leu, Cml, Tyr, or Ala
<220> FEATURE:
<221> NAME/KEY: MISC_FEATURE
<222> LOCATION: (9)..(9)
<223> OTHER INFORMATION: Xaa can be Nle, Cha, Met, Cml, or Phe
<220> FEATURE:
<221> NAME/KEY: MISC_FEATURE
<222> LOCATION: (10)..(10)
<223> OTHER INFORMATION: Xaa can be Glu, Asp, Aib, or Ala
<220> FEATURE:
<221> NAME/KEY: MISC_FEATURE
<222> LOCATION: (11)..(11)
<223> OTHER INFORMATION: Xaa can be Ile, Cml, or Ala
<220> FEATURE:
<221> NAME/KEY: MISC_FEATURE
<222> LOCATION: (12)..(12)
<223> OTHER INFORMATION: Xaa can be Ile, Ala, Leu, Val, Aib, Gly, Cml,
      Nle, Nva, Gln, Asn, or Phe

<400> SEQUENCE: 5

Xaa Xaa Xaa Xaa Xaa Xaa Xaa Xaa Xaa Xaa Xaa Xaa
```

-continued

```
1               5                   10
```

<210> SEQ ID NO 6
<211> LENGTH: 33
<212> TYPE: PRT
<213> ORGANISM: Artificial sequence
<220> FEATURE:
<223> OTHER INFORMATION: Cyclic corticotrophin releasing factor
      antagonist peptide
<220> FEATURE:
<221> NAME/KEY: MISC_FEATURE
<222> LOCATION: (2)..(2)
<223> OTHER INFORMATION: Xaa can be Leu or Cml
<220> FEATURE:
<221> NAME/KEY: MISC_FEATURE
<222> LOCATION: (3)..(3)
<223> OTHER INFORMATION: Xaa can be Thr or Ser
<220> FEATURE:
<221> NAME/KEY: MISC_FEATURE
<222> LOCATION: (4)..(4)
<223> OTHER INFORMATION: Xaa can be DPhe, DLeu, DTyr, DTrp, DCpa, DTrp,
      DNal, DPal, Phe, or Tyr
<220> FEATURE:
<221> NAME/KEY: MISC_FEATURE
<222> LOCATION: (5)..(5)
<223> OTHER INFORMATION: Xaa is DPhe
<220> FEATURE:
<221> NAME/KEY: MISC_FEATURE
<222> LOCATION: (6)..(6)
<223> OTHER INFORMATION: Xaa  can be His, Tyr or Glu
<220> FEATURE:
<221> NAME/KEY: MISC_FEATURE
<222> LOCATION: (7)..(7)
<223> OTHER INFORMATION: Xaa can be Cml or Leu
<220> FEATURE:
<221> NAME/KEY: MISC_FEATURE
<222> LOCATION: (9)..(9)
<223> OTHER INFORMATION: Xaa can be Leu or Cml
<220> FEATURE:
<221> NAME/KEY: MISC_FEATURE
<222> LOCATION: (10)..(10)
<223> OTHER INFORMATION: Xaa can be Glu, Cml, Asn
<220> FEATURE:
<221> NAME/KEY: MISC_FEATURE
<222> LOCATION: (11)..(11)
<223> OTHER INFORMATION: Xaa can be Leu or Ile
<220> FEATURE:
<221> NAME/KEY: MISC_FEATURE
<222> LOCATION: (12)..(12)
<223> OTHER INFORMATION: Xaa can be Glu, DGlu, or His
<220> FEATURE:
<221> NAME/KEY: MISC_FEATURE
<222> LOCATION: (13)..(13)
<223> OTHER INFORMATION: Xaa can be Nle or Met
<220> FEATURE:
<221> NAME/KEY: MISC_FEATURE
<222> LOCATION: (14)..(14)
<223> OTHER INFORMATION: Xaa can be Ala, DAla, Aib, Asp, Thr, DThr, Glu,
      or DGlu
<220> FEATURE:
<221> NAME/KEY: MISC_FEATURE
<222> LOCATION: (15)..(15)
<223> OTHER INFORMATION: Xaa can be Arg or Lys
<220> FEATURE:
<221> NAME/KEY: MISC_FEATURE
<222> LOCATION: (16)..(16)
<223> OTHER INFORMATION: Xaa can be Ala, Aib or Cml
<220> FEATURE:
<221> NAME/KEY: MISC_FEATURE
<222> LOCATION: (17)..(17)
<223> OTHER INFORMATION: Xaa can be Glu or Asp
<220> FEATURE:
<221> NAME/KEY: MISC_FEATURE
<222> LOCATION: (18)..(18)
<223> OTHER INFORMATION: Xaa can be Gln, Asn or Lys
<220> FEATURE:
<221> NAME/KEY: MISC_FEATURE
<222> LOCATION: (19)..(19)

```
<223> OTHER INFORMATION: Xaa is Cml
<220> FEATURE:
<221> NAME/KEY: MISC_FEATURE
<222> LOCATION: (20)..(20)
<223> OTHER INFORMATION: Xaa can be Ala, Lys, Aib or Arg
<220> FEATURE:
<221> NAME/KEY: MISC_FEATURE
<222> LOCATION: (21)..(21)
<223> OTHER INFORMATION: Xaa can be Gln, Aib or Glu
<220> FEATURE:
<221> NAME/KEY: MISC_FEATURE
<222> LOCATION: (23)..(23)
<223> OTHER INFORMATION: Xaa can be Aib or an L-isomer of an amino acid
      other than Cys
<220> FEATURE:
<221> NAME/KEY: MISC_FEATURE
<222> LOCATION: (24)..(24)
<223> OTHER INFORMATION: Xaa can be Aib or a D or L isomer of an amino
      acid other than Cys
<220> FEATURE:
<221> NAME/KEY: MISC_FEATURE
<222> LOCATION: (25)..(25)
<223> OTHER INFORMATION: Xaa can be Lys or Orn
<220> FEATURE:
<221> NAME/KEY: MISC_FEATURE
<222> LOCATION: (26)..(26)
<223> OTHER INFORMATION: Xaa can be Asn or Aib
<220> FEATURE:
<221> NAME/KEY: MISC_FEATURE
<222> LOCATION: (28)..(28)
<223> OTHER INFORMATION: Xaa can be Lys, Orn, Arg, Har, Cml or Leu
<220> FEATURE:
<221> NAME/KEY: MISC_FEATURE
<222> LOCATION: (29)..(29)
<223> OTHER INFORMATION: Xaa can be Cml, Leu or Tyr
<220> FEATURE:
<221> NAME/KEY: MISC_FEATURE
<222> LOCATION: (30)..(30)
<223> OTHER INFORMATION: Xaa can be Nle, Met or Cml
<220> FEATURE:
<221> NAME/KEY: MISC_FEATURE
<222> LOCATION: (31)..(31)
<223> OTHER INFORMATION: Xaa can be Glu, Aib or Asp
<220> FEATURE:
<221> NAME/KEY: MISC_FEATURE
<222> LOCATION: (32)..(32)
<223> OTHER INFORMATION: Xaa can be Cml, Ile, Aib, Thr, Asn, Glu, Ala,
      Val, Leu, Nle, Phe, Nva, Gly or Gln
<220> FEATURE:
<221> NAME/KEY: MISC_FEATURE
<222> LOCATION: (33)..(33)
<223> OTHER INFORMATION: Xaa can be Ala, Aib, Ile, Gly, Val, Leu, Cml,
      Nle, Phe, Nva or Gln

<400> SEQUENCE: 6

Asp Xaa Xaa Xaa Xaa Xaa Xaa Arg Xaa Xaa Xaa Xaa Xaa Xaa Xaa Xaa
1               5                   10                  15

Xaa Xaa Xaa Xaa Xaa Glu Xaa Xaa Xaa Xaa Arg Xaa Xaa Xaa Xaa Xaa
            20                  25                  30

Xaa

<210> SEQ ID NO 7
<211> LENGTH: 33
<212> TYPE: PRT
<213> ORGANISM: Artificial sequence
<220> FEATURE:
<223> OTHER INFORMATION: Cyclic corticotrophin releasing factor
      antagonist peptide
<220> FEATURE:
<221> NAME/KEY: MISC_FEATURE
<222> LOCATION: (4)..(4)
<223> OTHER INFORMATION: Xaa can be DPhe or D2Nal
<220> FEATURE:
<221> NAME/KEY: MISC_FEATURE
<222> LOCATION: (6)..(6)
```

```
<223> OTHER INFORMATION: Xaa can be Leu or Cml
<220> FEATURE:
<221> NAME/KEY: MISC_FEATURE
<222> LOCATION: (10)..(10)
<223> OTHER INFORMATION: Xaa can be Val, Cml or Nle
<220> FEATURE:
<221> NAME/KEY: MISC_FEATURE
<222> LOCATION: (11)..(11)
<223> OTHER INFORMATION: Xaa can be Leu or Ile
<220> FEATURE:
<221> NAME/KEY: MISC_FEATURE
<222> LOCATION: (12)..(12)
<223> OTHER INFORMATION: Xaa can be Glu or DGlu
<220> FEATURE:
<221> NAME/KEY: MISC_FEATURE
<222> LOCATION: (13)..(13)
<223> OTHER INFORMATION: Xaa can be Nle or Met
<220> FEATURE:
<221> NAME/KEY: MISC_FEATURE
<222> LOCATION: (14)..(14)
<223> OTHER INFORMATION: Xaa can be Ala, DAla, Aib or Thr
<220> FEATURE:
<221> NAME/KEY: MISC_FEATURE
<222> LOCATION: (15)..(15)
<223> OTHER INFORMATION: Xaa can be Arg or Lys
<220> FEATURE:
<221> NAME/KEY: MISC_FEATURE
<222> LOCATION: (16)..(16)
<223> OTHER INFORMATION: Xaa can be Ala or Aib
<220> FEATURE:
<221> NAME/KEY: MISC_FEATURE
<222> LOCATION: (17)..(17)
<223> OTHER INFORMATION: Xaa can be Asp or Glu
<220> FEATURE:
<221> NAME/KEY: MISC_FEATURE
<222> LOCATION: (19)..(19)
<223> OTHER INFORMATION: Xaa is Cml
<220> FEATURE:
<221> NAME/KEY: MISC_FEATURE
<222> LOCATION: (20)..(20)
<223> OTHER INFORMATION: Xaa can be Ala or Aib
<220> FEATURE:
<221> NAME/KEY: MISC_FEATURE
<222> LOCATION: (23)..(23)
<223> OTHER INFORMATION: Xaa can be Ala or Aib
<220> FEATURE:
<221> NAME/KEY: MISC_FEATURE
<222> LOCATION: (24)..(24)
<223> OTHER INFORMATION: Xaa can be Aib, DHis, imBzl, DHis, DArg, D2Nal,
      or a D isomer of another basic and/or aromatic amino acid
<220> FEATURE:
<221> NAME/KEY: MISC_FEATURE
<222> LOCATION: (25)..(25)
<223> OTHER INFORMATION: Xaa can be Lys or Orn
<220> FEATURE:
<221> NAME/KEY: MISC_FEATURE
<222> LOCATION: (26)..(26)
<223> OTHER INFORMATION: Xaa can be Aib or Asn
<220> FEATURE:
<221> NAME/KEY: MISC_FEATURE
<222> LOCATION: (28)..(28)
<223> OTHER INFORMATION: Xaa can be Lys or Cml
<220> FEATURE:
<221> NAME/KEY: MISC_FEATURE
<222> LOCATION: (29)..(29)
<223> OTHER INFORMATION: Xaa can be Leu or Cml
<220> FEATURE:
<221> NAME/KEY: MISC_FEATURE
<222> LOCATION: (30)..(30)
<223> OTHER INFORMATION: Xaa is Nle
<220> FEATURE:
<221> NAME/KEY: MISC_FEATURE
<222> LOCATION: (31)..(31)
<223> OTHER INFORMATION: Xaa can be Glu or Asp
<220> FEATURE:
<221> NAME/KEY: MISC_FEATURE
<222> LOCATION: (32)..(32)
<223> OTHER INFORMATION: Xaa can be Ile, Cml or Aib
<220> FEATURE:
```

```
<221> NAME/KEY: MISC_FEATURE
<222> LOCATION: (33)..(33)
<223> OTHER INFORMATION: Xaa can be Ala, Aib, Cml or Ile

<400> SEQUENCE: 7

Asp Leu Thr Xaa His Xaa Leu Arg Glu Xaa Xaa Xaa Xaa Xaa Xaa
1               5                   10                  15

Xaa Gln Xaa Xaa Gln Glu Xaa Xaa Xaa Xaa Arg Xaa Xaa Xaa Xaa Xaa
            20                  25                  30

Xaa

<210> SEQ ID NO 8
<211> LENGTH: 33
<212> TYPE: PRT
<213> ORGANISM: Artificial sequence
<220> FEATURE:
<223> OTHER INFORMATION: Cyclic corticotrophin releasing factor
      antagonist peptide
<220> FEATURE:
<221> NAME/KEY: MISC_FEATURE
<222> LOCATION: (4)..(4)
<223> OTHER INFORMATION: Xaa can be Dphe
<220> FEATURE:
<221> NAME/KEY: MISC_FEATURE
<222> LOCATION: (6)..(6)
<223> OTHER INFORMATION: Xaa can be Leu or Cml
<220> FEATURE:
<221> NAME/KEY: MISC_FEATURE
<222> LOCATION: (10)..(10)
<223> OTHER INFORMATION: Xaa can be Val, Cml or Nle
<220> FEATURE:
<221> NAME/KEY: MISC_FEATURE
<222> LOCATION: (12)..(12)
<223> OTHER INFORMATION: Xaa can be Glu or DGlu
<220> FEATURE:
<221> NAME/KEY: MISC_FEATURE
<222> LOCATION: (13)..(13)
<223> OTHER INFORMATION: Xaa can be Nle
<220> FEATURE:
<221> NAME/KEY: MISC_FEATURE
<222> LOCATION: (14)..(14)
<223> OTHER INFORMATION: Xaa can be Ala, Aib, DAla or Thr
<220> FEATURE:
<221> NAME/KEY: MISC_FEATURE
<222> LOCATION: (15)..(15)
<223> OTHER INFORMATION: Xaa can be Arg or Lys
<220> FEATURE:
<221> NAME/KEY: MISC_FEATURE
<222> LOCATION: (16)..(16)
<223> OTHER INFORMATION: Xaa can be Ala or Aib
<220> FEATURE:
<221> NAME/KEY: MISC_FEATURE
<222> LOCATION: (17)..(17)
<223> OTHER INFORMATION: Xaa can be Asp or Glu
<220> FEATURE:
<221> NAME/KEY: MISC_FEATURE
<222> LOCATION: (19)..(19)
<223> OTHER INFORMATION: Xaa can be Cml
<220> FEATURE:
<221> NAME/KEY: MISC_FEATURE
<222> LOCATION: (20)..(20)
<223> OTHER INFORMATION: Xaa can be Ala or Aib
<220> FEATURE:
<221> NAME/KEY: MISC_FEATURE
<222> LOCATION: (21)..(21)
<223> OTHER INFORMATION: Xaa can be Gln or Glu
<220> FEATURE:
<221> NAME/KEY: MISC_FEATURE
<222> LOCATION: (23)..(23)
<223> OTHER INFORMATION: Xaa can be Ala or Aib
<220> FEATURE:
<221> NAME/KEY: MISC_FEATURE
<222> LOCATION: (24)..(24)
<223> OTHER INFORMATION: Xaa can be Aib, His, DHis, DArg, imBzl DHis,
      DNal, DGlu, DAla, DPal, DTrp, D Dpr(Nic), DAph, DAgl(Nic), DOrn,
```

```
           DDbu, DDpr, or DOrn(Nic)
<220> FEATURE:
<221> NAME/K

```
<223> OTHER INFORMATION: Xaa can be Arg or Lys
<220> FEATURE:
<221> NAME/KEY: MISC_FEATURE
<222> LOCATION: (16)..(16)
<223> OTHER INFORMATION: Xaa can be Ala or Cml
<220> FEATURE:
<221> NAME/KEY: MISC_FEATURE
<222> LOCATION: (19)..(19)
<223> OTHER INFORMATION: Xaa is Cml
<220> FEATURE:
<221> NAME/KEY: MISC_FEATURE
<222> LOCATION: (24)..(24)
<223> OTHER INFORMATION: Xaa can be Aib, His, DHis, imBzl DHis, DArg,
     DAsn, DTyr, DPal, DNal, DTrp or another basic and/or aromatic D
     isomer amino acid
<220> FEATURE:
<221> NAME/KEY: MISC_FEATURE
<222> LOCATION: (25)..(25)
<223> OTHER INFORMATION: Xaa can be Lys or Orn
<220> FEATURE:
<221> NAME/KEY: MISC_FEATURE
<222> LOCATION: (28)..(28)
<223> OTHER INFORMATION: Xaa can be Lys or Cml
<220> FEATURE:
<221> NAME/KEY: MISC_FEATURE
<222> LOCATION: (29)..(29)
<223> OTHER INFORMATION: Xaa can be Leu or Cml
<220> FEATURE:
<221> NAME/KEY: MISC_FEATURE
<222> LOCATION: (30)..(30)
<223> OTHER INFORMATION: Xaa can be Met, Nle or Cml
<220> FEATURE:
<221> NAME/KEY: MISC_FEATURE
<222> LOCATION: (32)..(33)
<223> OTHER INFORMATION: Xaa can be Ile or Cml

<400> SEQUENCE: 9

Asp Xaa Thr Xaa His Xaa Xaa Arg Xaa Xaa Leu Glu Xaa Ala Xaa Xaa
1               5                   10                  15

Glu Gln Xaa Ala Gln Glu Ala Xaa Xaa Asn Arg Xaa Xaa Xaa Glu Xaa
            20                  25                  30

Xaa

<210> SEQ ID NO 10
<211> LENGTH: 33
<212> TYPE: PRT
<213> ORGANISM: Artificial sequence
<220> FEATURE:
<223> OTHER INFORMATION: Cyclic corticotrophin releasing factor
     antagonist peptide
<220> FEATURE:
<221> NAME/KEY: MISC_FEATURE
<222> LOCATION: (2)..(2)
<223> OTHER INFORMATION: Xaa can be Leu or Cml
<220> FEATURE:
<221> NAME/KEY: MISC_FEATURE
<222> LOCATION: (4)..(4)
<223> OTHER INFORMATION: Xaa can be DPhe or D2Nal
<220> FEATURE:
<221> NAME/KEY: MISC_FEATURE
<222> LOCATION: (6)..(7)
<223> OTHER INFORMATION: Xaa can be Leu or Cml
<220> FEATURE:
<221> NAME/KEY: MISC_FEATURE
<222> LOCATION: (9)..(9)
<223> OTHER INFORMATION: Xaa can be Glu or Cml
<220> FEATURE:
<221> NAME/KEY: MISC_FEATURE
<222> LOCATION: (10)..(10)
<223> OTHER INFORMATION: Xaa can be Val or Cml;
<220> FEATURE:
<221> NAME/KEY: MISC_FEATURE
<222> LOCATION: (13)..(13)
<223> OTHER INFORMATION: Xaa can be Met or Nle
<220> FEATURE:
```

```
<221> NAME/KEY: MISC_FEATURE
<222> LOCATION: (14)..(14)
<223> OTHER INFORMATION: Xaa can be Ala or Aib
<220> FEATURE:
<221> NAME/KEY: MISC_FEATURE
<222> LOCATION: (15)..(15)
<223> OTHER INFORMATION: Xaa can be Arg or Lys
<220> FEATURE:
<221> NAME/KEY: MISC_FEATURE
<222> LOCATION: (16)..(16)
<223> OTHER INFORMATION: Xaa can be Ala, Aib or Cml
<220> FEATURE:
<221> NAME/KEY: MISC_FEATURE
<222> LOCATION: (19)..(19)
<223> OTHER INFORMATION: Xaa is Cml
<220> FEATURE:
<221> NAME/KEY: MISC_FEATURE
<222> LOCATION: (20)..(20)
<223> OTHER INFORMATION: Xaa can be Ala or Aib
<220> FEATURE:
<221> NAME/KEY: MISC_FEATURE
<222> LOCATION: (21)..(21)
<223> OTHER INFORMATION: Xaa can be Gln or Aib
<220> FEATURE:
<221> NAME/KEY: MISC_FEATURE
<222> LOCATION: (23)..(23)
<223> OTHER INFORMATION: Xaa can be Ala or Aib
<220> FEATURE:
<221> NAME/KEY: MISC_FEATURE
<222> LOCATION: (24)..(24)
<223> OTHER INFORMATION: Xaa can be His, Aib, DHis, imBzl DHis, DArg,
      DAsn, DTyr, DPal, DNal, DTrp or another basic and/or aromatic D
      isomer amino acid
<220> FEATURE:
<221> NAME/KEY: MISC_FEATURE
<222> LOCATION: (25)..(25)
<223> OTHER INFORMATION: Xaa can be Lys or Orn
<220> FEATURE:
<221> NAME/KEY: MISC_FEATURE
<222> LOCATION: (26)..(26)
<223> OTHER INFORMATION: Xaa can be Asn or Aib
<220> FEATURE:
<221> NAME/KEY: MISC_FEATURE
<222> LOCATION: (28)..(28)
<223> OTHER INFORMATION: Xaa can be Lys or Cml
<220> FEATURE:
<221> NAME/KEY: MISC_FEATURE
<222> LOCATION: (29)..(29)
<223> OTHER INFORMATION: Xaa can be Leu or Cml
<220> FEATURE:
<221> NAME/KEY: MISC_FEATURE
<222> LOCATION: (30)..(30)
<223> OTHER INFORMATION: Xaa can be Met, Nle or Cml
<220> FEATURE:
<221> NAME/KEY: MISC_FEATURE
<222> LOCATION: (31)..(31)
<223> OTHER INFORMATION: Xaa can be Glu or Aib
<220> FEATURE:
<221> NAME/KEY: MISC_FEATURE
<222> LOCATION: (32)..(32)
<223> OTHER INFORMATION: Xaa can be Ile, Cml or Aib
<220> FEATURE:
<221> NAME/KEY: MISC_FEATURE
<222> LOCATION: (33)..(33)
<223> OTHER INFORMATION: Xaa can be Leu, Cml or Aib

<400> SEQUENCE: 10

Asp Xaa Thr Xaa His Xaa Xaa Arg Xaa Xaa Leu Glu Xaa Xaa Xaa Xaa
1               5                   10                  15

Glu Gln Xaa Xaa Xaa Glu Xaa Xaa Xaa Xaa Arg Xaa Xaa Xaa Xaa Xaa
            20                  25                  30

Xaa

<210> SEQ ID NO 11
<211> LENGTH: 33
```

```
<212> TYPE: PRT
<213> ORGANISM: Artificial sequence
<220> FEATURE:
<223> OTHER INFORMATION: Cyclic corticotrophin releasing factor
      antagonist peptide
<220> FEATURE:
<221> NAME/KEY: MISC_FEATURE
<222> LOCATION: (4)..(4)
<223> OTHER INFORMATION: Xaa is DPhe
<220> FEATURE:
<221> NAME/KEY: MISC_FEATURE
<222> LOCATION: (6)..(6)
<223> OTHER INFORMATION: Xaa can be Leu or Cml
<220> FEATURE:
<221> NAME/KEY: MISC_FEATURE
<222> LOCATION: (10)..(10)
<223> OTHER INFORMATION: Xaa can be Val, Cml or Nle
<220> FEATURE:
<221> NAME/KEY: MISC_FEATURE
<222> LOCATION: (12)..(12)
<223> OTHER INFORMATION: Xaa can be Glu or DGlu
<220> FEATURE:
<221> NAME/KEY: MISC_FEATURE
<222> LOCATION: (13)..(13)
<223> OTHER INFORMATION: Xaa is Nle
<220> FEATURE:
<221> NAME/KEY: MISC_FEATURE
<222> LOCATION: (14)..(14)
<223> OTHER INFORMATION: Xaa can be Ala or Aib
<220> FEATURE:
<221> NAME/KEY: MISC_FEATURE
<222> LOCATION: (16)..(16)
<223> OTHER INFORMATION: Xaa can be Ala or Aib
<220> FEATURE:
<221> NAME/KEY: MISC_FEATURE
<222> LOCATION: (17)..(17)
<223> OTHER INFORMATION: Xaa can be Asp or Glu
<220> FEATURE:
<221> NAME/KEY: MISC_FEATURE
<222> LOCATION: (19)..(19)
<223> OTHER INFORMATION: Xaa can be Cml
<220> FEATURE:
<221> NAME/KEY: MISC_FEATURE
<222> LOCATION: (20)..(20)
<223> OTHER INFORMATION: Xaa can be Ala or Aib
<220> FEATURE:
<221> NAME/KEY: MISC_FEATURE
<222> LOCATION: (23)..(23)
<223> OTHER INFORMATION: Xaa can be Ala or Aib
<220> FEATURE:
<221> NAME/KEY: MISC_FEATURE
<222> LOCATION: (24)..(24)
<223> OTHER INFORMATION: Xaa can be His, Aib, DHis, DArg, DNal, DGlu,
      DAla, DPal, DTrp, DAph, DOrn, D Dbu or D Dpr
<220> FEATURE:
<221> NAME/KEY: MISC_FEATURE
<222> LOCATION: (25)..(25)
<223> OTHER INFORMATION: Xaa can be Lys or Orn
<220> FEATURE:
<221> NAME/KEY: MISC_FEATURE
<222> LOCATION: (26)..(26)
<223> OTHER INFORMATION: Xaa can be Asn or Aib
<220> FEATURE:
<221> NAME/KEY: MISC_FEATURE
<222> LOCATION: (28)..(28)
<223> OTHER INFORMATION: Xaa can be Lys or Cml
<220> FEATURE:
<221> NAME/KEY: MISC_FEATURE
<222> LOCATION: (29)..(29)
<223> OTHER INFORMATION: Xaa can be Leu or Cml
<220> FEATURE:
<221> NAME/KEY: MISC_FEATURE
<222> LOCATION: (30)..(30)
<223> OTHER INFORMATION: Xaa is Nle
<220> FEATURE:
<221> NAME/KEY: MISC_FEATURE
<222> LOCATION: (31)..(31)
<223> OTHER INFORMATION: Xaa can be Glu or Asp
<220> FEATURE:
```

```
<221> NAME/KEY: MISC_FEATURE
<222> LOCATION: (32)..(32)
<223> OTHER INFORMATION: Xaa can be Ile, Cml or Aib
<220> FEATURE:
<221> NAME/KEY: MISC_FEATURE
<222> LOCATION: (33)..(33)
<223> OTHER INFORMATION: Xaa can be Ile, Aib, Cml or Ala

<400> SEQUENCE: 11

Asp Leu Thr Xaa His Xaa Leu Arg Glu Xaa Leu Xaa Xaa Xaa Arg Xaa
1               5                   10                  15

Xaa Gln Xaa Xaa Gln Glu Xaa Xaa Xaa Arg Xaa Xaa Xaa Xaa
            20                  25                  30

Xaa

<210> SEQ ID NO 12
<211> LENGTH: 33
<212> TYPE: PRT
<213> ORGANISM: Artificial sequence
<220> FEATURE:
<223> OTHER INFORMATION: Cyclic corticotrophin releasing factor
      antagonist peptide
<220> FEATURE:
<221> NAME/KEY: MISC_FEATURE
<222> LOCATION: (2)..(2)
<223> OTHER INFORMATION: Xaa can be Leu or Cml
<220> FEATURE:
<221> NAME/KEY: MISC_FEATURE
<222> LOCATION: (4)..(4)
<223> OTHER INFORMATION: Xaa can be DPhe or D2Nal
<220> FEATURE:
<221> NAME/KEY: MISC_FEATURE
<222> LOCATION: (6)..(7)
<223> OTHER INFORMATION: Xaa can be Leu or Cml
<220> FEATURE:
<221> NAME/KEY: MISC_FEATURE
<222> LOCATION: (9)..(9)
<223> OTHER INFORMATION: Xaa can be Glu or Cml
<220> FEATURE:
<221> NAME/KEY: MISC_FEATURE
<222> LOCATION: (10)..(10)
<223> OTHER INFORMATION: Xaa can be Val or Cml
<220> FEATURE:
<221> NAME/KEY: MISC_FEATURE
<222> LOCATION: (13)..(13)
<223> OTHER INFORMATION: Xaa can be Met or Nle
<220> FEATURE:
<221> NAME/KEY: MISC_FEATURE
<222> LOCATION: (16)..(16)
<223> OTHER INFORMATION: Xaa can be Ala or Cml
<220> FEATURE:
<221> NAME/KEY: MISC_FEATURE
<222> LOCATION: (19)..(19)
<223> OTHER INFORMATION: Xaa is Cml
<220> FEATURE:
<221> NAME/KEY: MISC_FEATURE
<222> LOCATION: (24)..(24)
<223> OTHER INFORMATION: Xaa can be His, Aib, DHis, imBzl DHis, DArg,
      DAsn, DTyr, DPal, DNal, DTrp or another basic and/or aromatic D
      isomer amino acid
<220> FEATURE:
<221> NAME/KEY: MISC_FEATURE
<222> LOCATION: (25)..(25)
<223> OTHER INFORMATION: Xaa can be Lys or Orn
<220> FEATURE:
<221> NAME/KEY: MISC_FEATURE
<222> LOCATION: (28)..(28)
<223> OTHER INFORMATION: Xaa can be Lys or Cml
<220> FEATURE:
<221> NAME/KEY: MISC_FEATURE
<222> LOCATION: (29)..(29)
<223> OTHER INFORMATION: Xaa can be Leu or Cml
<220> FEATURE:
<221> NAME/KEY: MISC_FEATURE
<222> LOCATION: (30)..(30)
```

<223> OTHER INFORMATION: Xaa can be Met, Nle or Cml
<220> FEATURE:
<221> NAME/KEY: MISC_FEATURE
<222> LOCATION: (32)..(33)
<223> OTHER INFORMATION: Xaa can be Ile or Cml

<400> SEQUENCE: 12

Asp Xaa Thr Xaa His Xaa Xaa Arg Xaa Xaa Leu Glu Xaa Ala Arg Xaa
1               5                   10                  15

Glu Gln Xaa Ala Gln Glu Ala Xaa Xaa Asn Arg Xaa Xaa Xaa Glu Xaa
            20                  25                  30

Xaa

<210> SEQ ID NO 13
<211> LENGTH: 33
<212> TYPE: PRT
<213> ORGANISM: Artificial sequence
<220> FEATURE:
<223> OTHER INFORMATION: Cyclic corticotrophin releasing factor
      antagonist peptide
<220> FEATURE:
<221> NAME/KEY: MISC_FEATURE
<222> LOCATION: (4)..(4)
<223> OTHER INFORMATION: Xaa can be DPhe, DLeu, D2Nal or DTyr
<220> FEATURE:
<221> NAME/KEY: MISC_FEATURE
<222> LOCATION: (5)..(5)
<223> OTHER INFORMATION: Xaa can be His, Tyr or Glu
<220> FEATURE:
<221> NAME/KEY: MISC_FEATURE
<222> LOCATION: (6)..(7)
<223> OTHER INFORMATION: Xaa can be Leu or Cml
<220> FEATURE:
<221> NAME/KEY: MISC_FEATURE
<222> LOCATION: (9)..(9)
<223> OTHER INFORMATION: Xaa can be Glu or Cml
<220> FEATURE:
<221> NAME/KEY: MISC_FEATURE
<222> LOCATION: (9)..(9)
<223> OTHER INFORMATION: Xaa can be Glu or Cml
<220> FEATURE:
<221> NAME/KEY: MISC_FEATURE
<222> LOCATION: (10)..(10)
<223> OTHER INFORMATION: Xaa can be Val, Cml, Nle or Met
<220> FEATURE:
<221> NAME/KEY: MISC_FEATURE
<222> LOCATION: (12)..(12)
<223> OTHER INFORMATION: Xaa can be Glu or DGlu
<220> FEATURE:
<221> NAME/KEY: MISC_FEATURE
<222> LOCATION: (13)..(13)
<223> OTHER INFORMATION: Xaa is Nle
<220> FEATURE:
<221> NAME/KEY: MISC_FEATURE
<222> LOCATION: (14)..(14)
<223> OTHER INFORMATION: Xaa can be Ala, DAla, Aib, Thr, Asp or Glu
<220> FEATURE:
<221> NAME/KEY: MISC_FEATURE
<222> LOCATION: (15)..(15)
<223> OTHER INFORMATION: Xaa can be Arg or Lys
<220> FEATURE:
<221> NAME/KEY: MISC_FEATURE
<222> LOCATION: (16)..(16)
<223> OTHER INFORMATION: Xaa can be Ala, Aib or Cml
<220> FEATURE:
<221> NAME/KEY: MISC_FEATURE
<222> LOCATION: (17)..(17)
<223> OTHER INFORMATION: Xaa can be Asp or Glu
<220> FEATURE:
<221> NAME/KEY: MISC_FEATURE
<222> LOCATION: (18)..(18)
<223> OTHER INFORMATION: Xaa can be Gln, Asn or Lys
<220> FEATURE:
<221> NAME/KEY: MISC_FEATURE
<222> LOCATION: (19)..(19)

```
<223> OTHER INFORMATION: Xaa is Cml
<220> FEATURE:
<221> NAME/KEY: MISC_FEATURE
<222> LOCATION: (20)..(20)
<223> OTHER INFORMATION: Xaa can be Ala or Aib
<220> FEATURE:
<221> NAME/KEY: MISC_FEATURE
<222> LOCATION: (21)..(21)
<223> OTHER INFORMATION: Xaa can be Gln, Aib or Glu
<220> FEATURE:
<221> NAME/KEY: MISC_FEATURE
<222> LOCATION: (23)..(23)
<223> OTHER INFORMATION: Xaa can be Ala or Aib;
<220> FEATURE:
<221> NAME/KEY: MISC_FEATURE
<222> LOCATION: (24)..(24)
<223> OTHER INFORMATION: Xaa can be His, DHis, Aib, DArg, D2Nal, D3Pal,
      DTrp, imBzl DHis, Gly, Tyr, DTyr, Leu, DLeu, Ala or DAla
<220> FEATURE:
<221> NAME/KEY: MISC_FEATURE
<222> LOCATION: (25)..(25)
<223> OTHER INFORMATION: Xaa can be Lys or Orn
<220> FEATURE:
<221> NAME/KEY: MISC_FEATURE
<222> LOCATION: (26)..(26)
<223> OTHER INFORMATION: Xaa can be Asn or Aib
<220> FEATURE:
<221> NAME/KEY: MISC_FEATURE
<222> LOCATION: (28)..(28)
<223> OTHER INFORMATION: Xaa can be Lys, Orn, Arg, Har, Cml or Leu
<220> FEATURE:
<221> NAME/KEY: MISC_FEATURE
<222> LOCATION: (29)..(29)
<223> OTHER INFORMATION: Xaa can be Cml, Leu or Tyr
<220> FEATURE:
<221> NAME/KEY: MISC_FEATURE
<222> LOCATION: (30)..(30)
<223> OTHER INFORMATION: Xaa is Nle
<220> FEATURE:
<221> NAME/KEY: MISC_FEATURE
<222> LOCATION: (31)..(31)
<223> OTHER INFORMATION: Xaa can be Glu, Aib or Asp
<220> FEATURE:
<221> NAME/KEY: MISC_FEATURE
<222> LOCATION: (32)..(32)
<223> OTHER INFORMATION: Xaa can be Ile, Cml, Aib, Thr, Glu, Asn or Gln
<220> FEATURE:
<221> NAME/KEY: MISC_FEATURE
<222> LOCATION: (33)..(33)
<223> OTHER INFORMATION: Xaa can be Ala, Aib, Ile, Cml, Val or Phe

<400> SEQUENCE: 13

Asp Leu Thr Xaa Xaa Xaa Xaa Arg Xaa Xaa Leu Xaa Xaa Xaa Xaa Xaa
1               5                   10                  15

Xaa Xaa Xaa Xaa Xaa Glu Xaa Xaa Xaa Xaa Arg Xaa Xaa Xaa Xaa Xaa
            20                  25                  30

Xaa

<210> SEQ ID NO 14
<211> LENGTH: 33
<212> TYPE: PRT
<213> ORGANISM: Artificial sequence
<220> FEATURE:
<223> OTHER INFORMATION: Cyclic corticotrophin releasing factor
      antagonist peptide
<220> FEATURE:
<221> NAME/KEY: MISC_FEATURE
<222> LOCATION: (2)..(2)
<223> OTHER INFORMATION: Xaa can be Leu or Cml
<220> FEATURE:
<221> NAME/KEY: MISC_FEATURE
<222> LOCATION: (4)..(4)
<223> OTHER INFORMATION: Xaa can be DPhe or D2Nal
<220> FEATURE:
<221> NAME/KEY: MISC_FEATURE
```

```
<222> LOCATION: (6)..(7)
<223> OTHER INFORMATION: Xaa can be Leu or Cml
<220> FEATURE:
<221> NAME/KEY: MISC_FEATURE
<222> LOCATION: (9)..(9)
<223> OTHER INFORMATION: Xaa can be Glu or Cml
<220> FEATURE:
<221> NAME/KEY: MISC_FEATURE
<222> LOCATION: (10)..(10)
<223> OTHER INFORMATION: Xaa can be Val or Cml
<220> FEATURE:
<221> NAME/KEY: MISC_FEATURE
<222> LOCATION: (13)..(13)
<223> OTHER INFORMATION: Xaa can be Met or Nle
<220> FEATURE:
<221> NAME/KEY: MISC_FEATURE
<222> LOCATION: (16)..(16)
<223> OTHER INFORMATION: Xaa can be Ala or Cml
<220> FEATURE:
<221> NAME/KEY: MISC_FEATURE
<222> LOCATION: (19)..(19)
<223> OTHER INFORMATION: Xaa is Cml
<220> FEATURE:
<221> NAME/KEY: MISC_FEATURE
<222> LOCATION: (24)..(24)
<223> OTHER INFORMATION: Xaa can be His, DHis, imBzl DHis, DArg, DAsn,
      DTyr, DPal, DNal, DTrp or another basic and/or aromatic D isomer
      amino acid
<220> FEATURE:
<221> NAME/KEY: MISC_FEATURE
<222> LOCATION: (25)..(25)
<223> OTHER INFORMATION: Xaa can be Lys or Orn
<220> FEATURE:
<221> NAME/KEY: MISC_FEATURE
<222> LOCATION: (28)..(28)
<223> OTHER INFORMATION: Xaa can be Lys or Cml
<220> FEATURE:
<221> NAME/KEY: MISC_FEATURE
<222> LOCATION: (29)..(29)
<223> OTHER INFORMATION: Xaa can be Leu or Cml
<220> FEATURE:
<221> NAME/KEY: MISC_FEATURE
<222> LOCATION: (30)..(30)
<223> OTHER INFORMATION: Xaa can be Met, Nle or Cml
<220> FEATURE:
<221> NAME/KEY: MISC_FEATURE
<222> LOCATION: (32)..(33)
<223> OTHER INFORMATION: Xaa can be Ile or Cml

<400> SEQUENCE: 14

Asp Xaa Thr Xaa His Xaa Xaa Arg Xaa Xaa Leu Glu Xaa Ala Arg Xaa
1               5                   10                  15

Glu Gln Xaa Ala Gln Glu Ala Xaa Xaa Asn Arg Xaa Xaa Xaa Glu Xaa
            20                  25                  30

Xaa

<210> SEQ ID NO 15
<211> LENGTH: 33
<212> TYPE: PRT
<213> ORGANISM: Artificial sequence
<220> FEATURE:
<223> OTHER INFORMATION: Cyclic corticotrophin releasing factor
      antagonist peptide
<220> FEATURE:
<221> NAME/KEY: MISC_FEATURE
<222> LOCATION: (4)..(4)
<223> OTHER INFORMATION: Xaa can be DPhe or D2Nal
<220> FEATURE:
<221> NAME/KEY: MISC_FEATURE
<222> LOCATION: (13)..(13)
<223> OTHER INFORMATION: Xaa is Nle
<220> FEATURE:
<221> NAME/KEY: MISC_FEATURE
<222> LOCATION: (15)..(15)
<223> OTHER INFORMATION: Xaa can be Arg or Lys
```

```
<220> FEATURE:
<221> NAME/KEY: MISC_FEATURE
<222> LOCATION: (19)..(19)
<223> OTHER INFORMATION: Xaa is Cml
<220> FEATURE:
<221> NAME/KEY: MISC_FEATURE
<222> LOCATION: (25)..(25)
<223> OTHER INFORMATION: Xaa can be His, DHis, imBzl DHis, DArg, DTyr,
     DNal, DPal, DTrp, DAsn, DLys, D Dpr(Nic), DAph, DPhe, DCpa,
     DAgl(Nic), DOrn, D Dbu, D Dpr or DOrn(Nic)
<220> FEATURE:
<221> NAME/KEY: MISC_FEATURE
<222> LOCATION: (30)..(30)
<223> OTHER INFORMATION: Xaa is Nle

<400> SEQUENCE: 15

Asp Leu Thr Xaa His Leu Leu Arg Glu Val Leu Glu Xaa Ala Xaa Ala
1               5                   10                  15

Glu Asn Xaa Ala Asn Glu Ala His Xaa Arg Asn Lys Leu Xaa Glu Ile
            20                  25                  30

Ile
```